US011839624B2

(12) United States Patent
Ryu et al.

(10) Patent No.: US 11,839,624 B2
(45) Date of Patent: *Dec. 12, 2023

(54) MICELLAR NANOPARTICLES AND USES THEREOF

(71) Applicant: BIORCHESTRA CO., LTD., Daejeon (KR)

(72) Inventors: Jin-Hyeob Ryu, Daejeon (KR); Yu Na Lim, Daejeon (KR); Hyun Su Min, Daejeon (KR); Han Seok Koh, Daejeon (KR); Dae Hoon Kim, Daejeon (KR); Hyun-Jeong Cho, Daejeon (KR)

(73) Assignee: BIORCHESTRA CO., LTD., Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/502,923

(22) Filed: Oct. 15, 2021

(65) Prior Publication Data

US 2022/0105123 A1 Apr. 7, 2022

Related U.S. Application Data

(63) Continuation of application No. PCT/IB2020/056093, filed on Jun. 26, 2020.

(60) Provisional application No. 63/043,693, filed on Jun. 24, 2020, provisional application No. 62/867,097, filed on Jun. 26, 2019.

(51) Int. Cl.
| | |
|---|---|
| *C12N 15/11* | (2006.01) |
| *A61K 31/712* | (2006.01) |
| *A61P 35/00* | (2006.01) |
| *A61K 31/7125* | (2006.01) |
| *C12N 15/113* | (2010.01) |
| *A61K 47/69* | (2017.01) |
| *A61K 47/64* | (2017.01) |
| *A61K 47/54* | (2017.01) |
| *A61K 47/60* | (2017.01) |
| *A61P 25/28* | (2006.01) |
| *A61K 9/107* | (2006.01) |
| *C12N 15/88* | (2006.01) |

(52) U.S. Cl.
CPC .......... *A61K 31/712* (2013.01); *A61K 9/1075* (2013.01); *A61K 31/7125* (2013.01); *A61K 47/542* (2017.08); *A61K 47/60* (2017.08); *A61K 47/6455* (2017.08); *A61K 47/6907* (2017.08); *A61P 25/28* (2018.01); *A61P 35/00* (2018.01); *C12N 15/113* (2013.01); *C12N 15/88* (2013.01)

(58) Field of Classification Search
CPC . A61K 31/712; A61K 31/7125; C12N 15/113
See application file for complete search history.

(56) References Cited

U.S. PATENT DOCUMENTS

| | | | |
|---|---|---|---|
| 3,817,837 A | 6/1974 | Rubenstein et al. | |
| 4,683,195 A | 7/1987 | Mullis et al. | |
| 7,375,078 B2 | 5/2008 | Feng | |
| 8,163,708 B2 | 4/2012 | Elmen et al. | |
| 8,404,649 B2 | 3/2013 | Curtis et al. | |
| 8,580,756 B2 | 11/2013 | Hansen et al. | |
| 9,034,837 B2 | 5/2015 | Hildebrandt-Eriksen et al. | |
| 2007/0213292 A1 | 9/2007 | Stoffel et al. | |
| 2009/0156459 A1 | 6/2009 | Castillo et al. | |
| 2010/0178243 A1 | 7/2010 | Haas et al. | |
| 2012/0005765 A1* | 1/2012 | Kumar ........... | C12Y 102/01036 435/7.1 |
| 2014/0371292 A1 | 12/2014 | Besheer et al. | |
| 2015/0157721 A1* | 6/2015 | Wu ........................ | A61K 47/26 514/777 |
| 2018/0201928 A1 | 7/2018 | Obad et al. | |
| 2018/0280516 A1 | 10/2018 | Castillo et al. | |
| 2018/0334674 A1* | 11/2018 | Kondo ................ | A61K 9/1075 |
| 2019/0350870 A1 | 11/2019 | Farokhzad et al. | |

(Continued)

FOREIGN PATENT DOCUMENTS

| | | |
|---|---|---|
| CN | 111632153 A | 9/2020 |
| CN | 111819217 A | 10/2020 |

(Continued)

OTHER PUBLICATIONS

Lu et al, Folate-Conjugated Micelles and Their Folate Receptor-Mediated Endocytosis, Macromol. Biosci. 2009, 9: 1059-1068 (Year: 2009).*

Freeman et al., Metronidazole, Drugs, 1997, 54: 679-708 (Year: 1997).*

Jia et al., High Doses of Nicotinamide Prevent Oxidative Mitochondrial Dysfunction in a Cellular Model and Improve Motor Deficit in a *Drosophila* Model of Parkinson's disease, Journal of Neuroscience Research, 2008, 86: 2083-2090 (Year: 2008).*

(Continued)

*Primary Examiner* — Ekaterina Poliakova-Georgantas
(74) *Attorney, Agent, or Firm* — Sterne, Kessler, Goldstein & Fox P.L.L.C.

(57) ABSTRACT

The present disclosure includes cationic carrier units comprising (i) a water soluble polymer, (ii) a positively charged carrier, and (iii) an adjuvant moiety, wherein when the cationic carrier unit is mixed with an anionic payload (e.g., an antisense oligonucleotide) that electrostatically interacts with the cationic carrier unit, the resulting composition self-organizes into a micelle encapsulating the anionic payload in its core. The cationic carrier units can also comprise a tissue specific targeting moiety, which would be displayed on the surface of the micelle. The disclosure also includes micelles comprising the cationic carrier units of the disclosure, methods of manufacture of cationic carrier units and micelles, pharmaceutical compositions comprising the micelles, and also methods of treating diseases or conditions comprising administering the micelles to a subject in need thereof.

23 Claims, 30 Drawing Sheets

Specification includes a Sequence Listing.

(56) References Cited

U.S. PATENT DOCUMENTS

| | | | |
|---|---|---|---|
| 2020/0095605 A1 | 3/2020 | Watson et al. | |
| 2020/0281908 A1* | 9/2020 | Goncharova | A61P 25/28 |

FOREIGN PATENT DOCUMENTS

| | | |
|---|---|---|
| WO | WO-0244321 A2 | 6/2002 |
| WO | WO-2005013901 A2 | 2/2005 |
| WO | WO-2005023986 A2 | 3/2005 |
| WO | WO-2006093526 A2 | 9/2006 |
| WO | WO-2006112872 A2 | 10/2006 |
| WO | WO-2007021896 A2 | 2/2007 |
| WO | WO-2007027775 A2 | 3/2007 |
| WO | WO-2007027894 A2 | 3/2007 |
| WO | WO-2007090073 A2 | 8/2007 |
| WO | WO-2007112753 A2 | 10/2007 |
| WO | WO-2007112754 A2 | 10/2007 |
| WO | WO-2008046911 A2 | 4/2008 |
| WO | WO-2008074328 A2 | 6/2008 |
| WO | WO-2008091703 A2 | 7/2008 |
| WO | WO-2009020771 A2 | 2/2009 |
| WO | WO-2017212007 A1 | 12/2017 |
| WO | WO-2019204799 A1 | 10/2019 |
| WO | WO-2022144811 A1 | 7/2022 |
| WO | WO-2022144812 A1 | 7/2022 |

OTHER PUBLICATIONS

Harada et al., Physicochemical properties and nuclease resistance of antisense oligodeoxynucleotides entrapped in the core of polyion complex micelles composed of poly(ethylene glycol)-poly(L-Lysine) block copolymers, European Journal of Pharmaceutical Sciences, 2001, 13: 35-42 (Year: 2001).*

Chai, T.J., et al., "GPR109A and Vascular Inflammation," Current Atherosclerosis Reports 15(5):325, Springer, United States (May 2013).

Chien, H.C., et al., "Reevaluating the Substrate Specificity of the L-Type Amino Acid Transporter (LAT1)," Journal of Medicinal Chemistry 61(16):7358-7373, Author manuscript, American Chemical Society, United States (Aug. 2018).

Daneman, R. and Prat, A., "The Blood-brain Barrier," Cold Spring Harbor Perspectives in Biology 7(1):a020412, Cold Spring Harbor Laboratory Press, United States (Jan. 2015).

Dheur, S., et al., "Polyethylenimine but Not Cationic Lipid Improves Antisense Activity of 3'- capped Phosphodiester Oligonucleotides," Antisense & Nucleic Acid Drug Development 9(6):515-525, Mary Ann Liebert, United States (Dec. 1999).

Freshney, R.I., (ed), "Culture of Animal Cells, A Manual of Basic Technique," Chapters 18, 19 and 20, Second Edition, pp. 227-260, Alan R. Liss, Inc., United States (1987).

Geary, R.S., et al., "Pharmacokinetic Properties of 2'-O-(2-Methoxyethyl)-Modified Oligonucleotide Analogs in Rats," The Journal of Pharmacology and Experimental Therapeutics 296(3): 890-897, American Society for Pharmacology and Experimental Therapeutics, United States (Mar. 2001).

Geier, E.G., et al., "Structure-based Ligand Discovery for the Large-neutral Amino Acid Transporter 1, LAT-1," Proceedings of the National Academy of Sciences of the United States of America 110(14):5480-5485, National Academy of Sciences, United States (Apr. 2013).

Graff, E.C., et al., "Anti-inflammatory Effects of the Hydroxycarboxylic Acid Receptor 2," Metabolism 65(2):102-113, Elsevier, Netherlands (Feb. 2016).

Griffiths-Jones, S., et al., "miRBase: MicroRNA Sequences, Targets and Gene Nomenclature," Nucleic Acids Research 34(Database issue): D140-D144, Oxford University Press, England (Jan. 2006).

Griffiths-Jones, S., et al., "miRBase: Tools for MicroRNA Genomics," Nucleic Acids Research 36(Database issue): D154-D158, Oxford University Press, England (Jan. 2008).

Griffiths-Jones, S., "The microRNA Registry," Nucleic Acids Research 32(Database issue): D109-D111, Oxford University Press, England (Jan. 2004).

International Search Report and Written Opinion for International Application No. PCT/IB2020/056093, ISA/KR, Republic of Korea, dated Oct. 5, 2020, 13 pages.

Johansen, A., et al., "The Importance of Small Polar Radiometabolites in Molecular Neuroimaging: A Pet Study With [$^{11}$C]Cimbi-36 Labeled in Two Positions," Journal of Cerebral Blood Flow and Metabolism 38(4):659-668, SAGE Publications, United States (Apr. 2018).

Lieber, M., et al., "Establishment of a Continuous Tumor-cell Line (PANC-1) From a Human Carcinoma of the Exocrine Pancreas," International Journal of Cancer 15(5):741-747, Wiley-Liss, United States (May 1975).

Offermanns, S. and Schwaninger, M., "Nutritional or Pharmacological Activation of $HCA_2$ Ameliorates Neuroinflammation," Trends in Molecular Medicine 21(4):245-255, Elsevier Science Ltd, England (Apr. 2015).

Oudshoorn, M.H.M., et al., "Synthesis and Characterization of Hyperbranched Polyglycerol Hydrogels," Biomaterials 27(32):5471-5479, Elsevier Science, Netherlands (Nov. 2006).

Ooya, T., et al., "Effects of Ethylene Glycol-based Graft, Star-shaped, and Dendritic Polymers on Solubilization and Controlled Release of Paclitaxel," Journal of controlled release : official journal of the Controlled Release Society 93(2):121-127, Elsevier Science Publishers, Netherlands (Dec. 2003).

Senti G., et al., "Intralymphatic Allergen Administration Renders Specific Immunotherapy Faster and Safer: a Randomized Controlled Trial," PNAS 105(46):17908-17912, National Academy of Sciences, United States (Apr. 2008).

Singh, N. and Ecker, G.F., "Insights into the Structure, Function, and Ligand Discovery of the Large Neutral Amino Acid Transporter 1, LAT1," International Journal of Molecular Sciences 19(5):1278, MDPI, Switzerland (Apr. 2018).

Sutera, F.M., et al., "Small Endogenous Molecules as Moiety to Improve Targeting of CNS Drugs," Expert Opinion on Drug Delivery 14(1):93-107, Informa Healthcare, England (Jan. 2017).

Wakade, C. and Chong, R., "A Novel Treatment Target for Parkinson's Disease," Journal of the Neurological Sciences 347(1-2):34-38, Elsevier, Netherlands (Dec. 2014).

Wilms, D., et al., "Hyperbranched Polyglycerols: From the Controlled Synthesis of Biocompatible Polyether Polyols to Multipurpose Applications," Accounts of Chemical Research 43(1):129-141, American Chemical Society, United States (Jan. 2010).

International Search Report and Written Opinion for International Application No. PCT/IB2021/062447, dated Apr. 11, 2022, 10 pages.

International Search Report and Written Opinion for International Application No. PCT/IB2021/062446, dated Apr. 11, 2022, 10 pages.

Deng, J., et al., "Self-Assembled Cationic Micelles Based on PEG-PLL-PLLeu Hybrid Polypeptides as Highly Effective Gene Vectors," BioMacromolecules 13(11): 3795-3804, American Chemical Society, United States (Sep. 2012).

Koo, A.N., et al., "Disulfide-cross-linked PEG-poly(amino acid)s copolymer micelles for glutathione-mediated intracellular drug delivery," Chem Commun 48: 6570-6572, Royal Society of Chemistry, United Kingdom (Nov. 2008).

Koo, A.N., et al., "Tumor accumulation and antitumor efficacy of docetaxel-loaded core-shell-corona micelles with shell-specific redox-responsive cross-links," Biomaterials 33(5): 1489-1499, Elsevier, Netherlands (Feb. 2012).

Maekawa-Matsuura, M., et al., "LAT1-Targeting Thermoreresponsive Liposomes for Effective Cellular Uptake by Cancer Cells," ACS Omega 4(4): 6443-6451, American Chemical Society, United States (Apr. 2019).

Puris, E., et al., "L-Type amino acid transporter 1 as a target for drug delivery," Pharm Res. 37(5): 88, 17 pages, Springer Publishing, United Kingdom (May 2020).

(56) References Cited

OTHER PUBLICATIONS

Lin, X., et al., "Oil-in-ionic liquid nanoemulsion-based adjuvant simultaneously enhances the stability and immune responses of inactivated foot-and-mouth disease virus," *International Journal of Pharmaceutics* 625:122083, 14 pages, Elsevier, Netherlands (Sep. 2022).

Supplementary European Search Report for European Patent Application 20831649.7-1111/3990028 PCT/IB2020056093, European Patent Office, The Hague, 10 pages, dated Jul. 10, 2023.

* cited by examiner

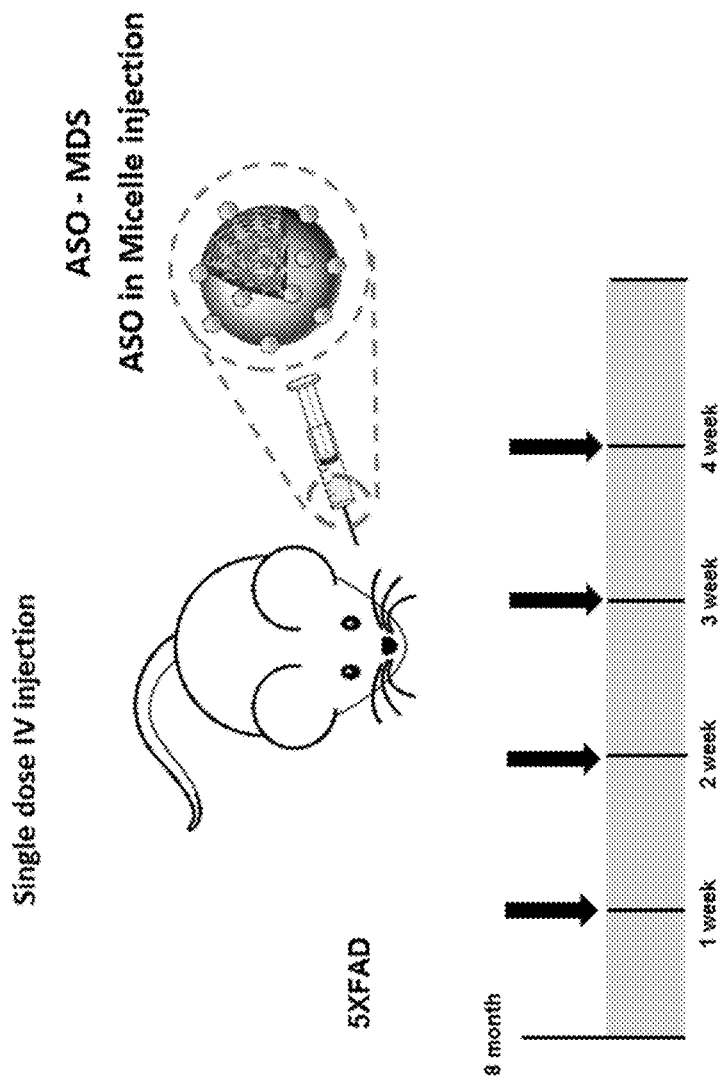

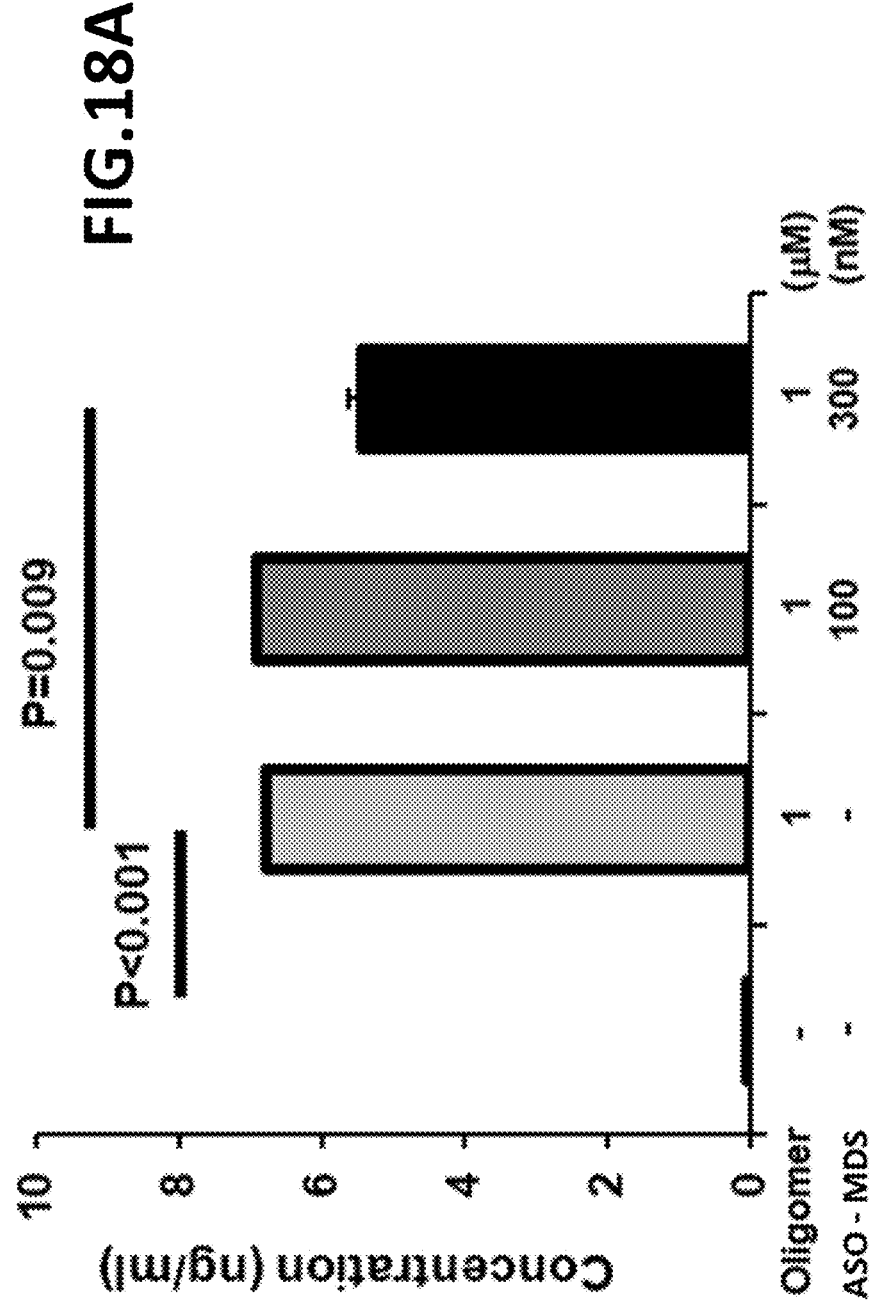

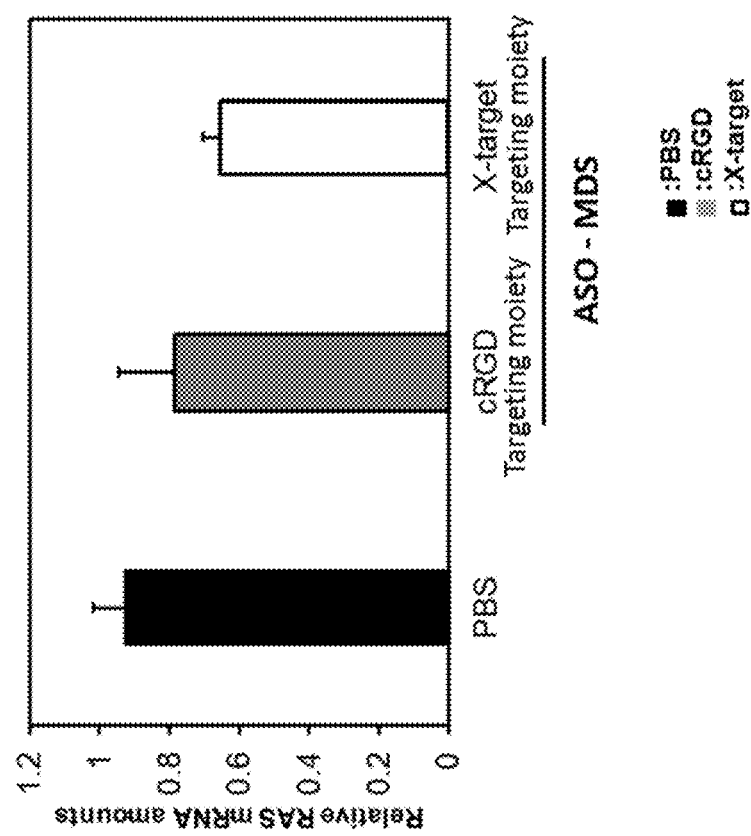

```
                         SEQUENCE LISTING

<160> NUMBER OF SEQ ID NOS: 22

<210> SEQ ID NO 1
<211> LENGTH: 2
<212> TYPE: PRT
<213> ORGANISM: Artificial Sequence
<220> FEATURE:
<223> OTHER INFORMATION: poly-G linker
<220> FEATURE:
<221> NAME/KEY: misc_feature
<222> LOCATION: (1)..(1)
<223> OTHER INFORMATION: Wherein Gly can be repeated 1 to 4 times
<220> FEATURE:
<221> NAME/KEY: misc_feature
<222> LOCATION: (2)..(2)
<223> OTHER INFORMATION: Wherein Ser can be present or absent
<220> FEATURE:
<221> NAME/KEY: misc_feature
<222> LOCATION: (1)..(2)
<223> OTHER INFORMATION: Wherein the entire unit can be repeated 1 to 50
      times

<400> SEQUENCE: 1

Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: peptide linker

<400> SEQUENCE: 2

Gly Gly Gly Gly
1

<210> SEQ ID NO 3
<211> LENGTH: 2
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)..(2)
<223> OTHER INFORMATION: Wherein the entire until can be repeated 1 to
      100 times

<400> SEQUENCE: 3

Gly Ala
1
```

```
<210> SEQ ID NO 4
<211> LENGTH: 3
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)..(3)
<223> OTHER INFORMATION: Wherein the entire unit can be repeated 1 to
      100 times

<400> SEQUENCE: 4

Gly Gly Ser
1

<210> SEQ ID NO 5
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)..(4)
<223> OTHER INFORMATION: Wherein the entire unit can be repeated 1 to
      100 times

<400> SEQUENCE: 5

Gly Gly Gly Ser
1

<210> SEQ ID NO 6
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)..(3)
<223> OTHER INFORMATION: Wherein the subsequence can be repeated 1 to
      100 times
<220> FEATURE:
<221> NAME/KEY: misc_feature
<222> LOCATION: (4)..(8)
<223> OTHER INFORMATION: Wherein the subsequence can be repeated 1 to
      100 times

<400> SEQUENCE: 6

Gly Gly Ser Gly Gly Gly Gly Ser
1               5

<210> SEQ ID NO 7
<211> LENGTH: 7
<212> TYPE: PRT
<213> ORGANISM: Artificial Sequence
<220> FEATURE:
<223> OTHER INFORMATION: peptide linker

<400> SEQUENCE: 7

Ser Gly Gly Ser Gly Gly Ser
1               5

<210> SEQ ID NO 8
<211> LENGTH: 15
<212> TYPE: PRT
<213> ORGANISM: Artificial Sequence
<220> FEATURE:
<223> OTHER INFORMATION: peptide linker
```

```
<400> SEQUENCE: 8

Gly Gly Ser Gly Gly Ser Gly Gly Ser Gly Gly Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: peptide linker

<400> SEQUENCE: 9

Gly Gly Ser Gly Gly Ser Gly Gly Gly Gly Ser Gly Gly Gly Gly Ser
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: peptide linker

<400> SEQUENCE: 10

Gly Gly Ser Gly Gly Ser Gly Gly Ser Gly Gly Ser Gly Gly Ser Gly
1               5                   10                  15

Gly Ser

<210> SEQ ID NO 11
<211> LENGTH: 15
<212> TYPE: PRT
<213> ORGANISM: Artificial Sequence
<220> FEATURE:
<223> OTHER INFORMATION: peptide linker

<400> SEQUENCE: 11

Gly Gly Gly Gly Ser Gly Gly Gly Ser Gly Gly Gly Gly Ser
1               5                   10                  15

<210> SEQ ID NO 12
<211> LENGTH: 4
<212> TYPE: PRT
<213> ORGANISM: Artificial Sequence
<220> FEATURE:
<223> OTHER INFORMATION: Poly-G linker sequence
<220> FEATURE:
<221> NAME/KEY: misc_feature
<222> LOCATION: (1)..(4)
<223> OTHER INFORMATION: wherein the unit can be repeated 1 to 100 times

<400> SEQUENCE: 12

Gly Gly Gly Gly
1

<210> SEQ ID NO 13
<211> LENGTH: 22
<212> TYPE: RNA
<213> ORGANISM: Artificial Sequence
<220> FEATURE:
<223> OTHER INFORMATION: has-miR-204-5p

<400> SEQUENCE: 13
uucccuuugu cauccuaugc cu                                              22

<210> SEQ ID NO 14
<211> LENGTH: 22
<212> TYPE: RNA
```

```
<213> ORGANISM: Artificial Sequence
<220> FEATURE:
<223> OTHER INFORMATION: hsa-miR-132-3p

<400> SEQUENCE: 14
uaacagucua cagccauggu cg                                              22

<210> SEQ ID NO 15
<211> LENGTH: 22
<212> TYPE: RNA
<213> ORGANISM: Artificial Sequence
<220> FEATURE:
<223> OTHER INFORMATION: antiMIR nucleotide sequence

<400> SEQUENCE: 15
aggcauagga ugacaaaggg aa                                              22

<210> SEQ ID NO 16
<211> LENGTH: 22
<212> TYPE: RNA
<213> ORGANISM: Artificial Sequence
<220> FEATURE:
<223> OTHER INFORMATION: hsa-miR-485-3p

<400> SEQUENCE: 16
cgaccauggc uguagacugu ua                                              22

<210> SEQ ID NO 17
<211> LENGTH: 22
<212> TYPE: RNA
<213> ORGANISM: Artificial Sequence
<220> FEATURE:
<223> OTHER INFORMATION: antiMIR nucleotide sequence

<400> SEQUENCE: 17
gucauacacg gcucuccucu cu                                              22

<210> SEQ ID NO 18
<211> LENGTH: 22
<212> TYPE: RNA
<213> ORGANISM: Artificial Sequence
<220> FEATURE:
<223> OTHER INFORMATION: antiMIR nucleotide sequence

<400> SEQUENCE: 18
agagaggaga gccguguaug ac                                              22

<210> SEQ ID NO 19
<211> LENGTH: 7
<212> TYPE: RNA
<213> ORGANISM: Artificial Sequence
<220> FEATURE:
<223> OTHER INFORMATION: has-miR-485-3p

<400> SEQUENCE: 19 ucauaca                                                                7

<210> SEQ ID NO 20
<211> LENGTH: 7
<212> TYPE: RNA
<213> ORGANISM: Artificial Sequence
<220> FEATURE:
<223> OTHER INFORMATION: antiMIR nucleotide sequence

<400> SEQUENCE: 20 uguauga                                                                7
```

```
<210> SEQ ID NO 21
<211> LENGTH: 7
<212> TYPE: RNA
<213> ORGANISM: Artificial Sequence
<220> FEATURE:
<223> OTHER INFORMATION: has-miR-204-5p

<400> SEQUENCE: 21 ucccuuu                                                                 7

<210> SEQ ID NO 22
<211> LENGTH: 7
<212> TYPE: DNA
<213> ORGANISM: Artificial Sequence
<220> FEATURE:
<223> OTHER INFORMATION: antiMIR nucleotide sequence

<400> SEQUENCE: 22 aaaggga                                                                 7
```

MICELLAR NANOPARTICLES AND USES THEREOF

CROSS-REFERENCE TO RELATED APPLICATIONS

This application is a continuation of International Application No. PCT/IB2020/056093, filed on Jun. 26, 2020, which claims priority to and the benefit of U.S. Provisional Application No. 62/867,097, filed on Jun. 26, 2019, and 63/043,693, filed on Jun. 24, 2020, each of which is incorporated by reference herein in its entirety.

REFERENCE TO SEQUENCE LISTING SUBMITTED ELECTRONICALLY

The content of the electronically submitted sequence listing in ASCII text file (Name 4366_0020003_Seq-listing_ST25; Size: 5,439 bytes; and Date of Creation: Oct. 15, 2021) filed with the application is incorporated herein by reference in its entirety.

FIELD

The present disclosure provides cationic carrier units and micelle systems, which can be used to deliver anionic payloads (e.g., oligonucleotides) across physiological permeation barriers, e.g., the brain blood barrier.

BACKGROUND ART

There are certain barriers present into the body, which restrict the permeability of the drug through the membrane. Thus, only selective substances can pass through this type of membranes. Some important and specialized physiological barrier are the blood brain barrier and the cell membrane. The blood-brain barrier (BBB) is a highly selective semipermeable border that separates the circulating blood from the brain and extracellular fluid in the central nervous system (CNS). The blood-brain barrier is formed by endothelial cells of the capillary wall, astrocyte end-feet ensheathing the capillary, and pericytes embedded in the capillary basement membrane. This system allows the passage of water, some gases, and lipid-soluble molecules by passive diffusion, as well as the selective transport of molecules such as glucose and amino acids that are crucial to neural function.

The blood-brain barrier restricts the passage of pathogens, the diffusion of solutes in the blood, and large or hydrophilic molecules into the cerebrospinal fluid (CSF), while allowing the diffusion of $O_2$, $CO_2$, hydrophobic molecules (e.g., hormones), and small polar molecules (Johansen et al., (2017) Journal of Cerebral Blood Flow and Metabolism. Epub (4): 659-668). The BBB excludes from the brain almost 100% of large-molecule neurotherapeutics and more than 98% of all molecule drugs. Daneman & Prat (2015) "The Blood Brain Barrier" Cold Spring Harbor Perspectives in Biology 7(1):a020412. Overcoming the difficulty of delivering therapeutic agents to specific regions of the brain represents a major challenge to treatment of most brain disorders. Thus, therapeutic molecules that might otherwise be effective in diagnosis and therapy do not cross the BBB in adequate amounts.

Intracellular targeting is also often challenging, because to reach the cytosol, exogenous molecules must first traverse the cell membrane. The cell membrane is selectively permeable to non-polar therapeutic agents, which are lipid soluble and can pass through the cell membrane. On the other hand, highly charged therapeutic agents such as oligonucleotides are effectively excluded by the cell membrane.

Polynucleotides do not readily permeate the cellular membrane due to the charge repulsion between the negatively charged membrane and the high negative charge on the polynucleotide. As a result, polynucleotides have poor bioavailability and uptake into cells, typically less than 1% (Dheur et al, Nucleic Acid Drug Dev., 9:522 (1999); Park et al, J Controlled Release, 93:188 (2003)). Since most polynucleotides are generally above 5,000 Da, they cannot readily diffuse through cellular membranes and uptake into cells is limited primarily to pinocytotic or endocytotic processes. Once inside the cell, polynucleotides can accumulate in lysosomal compartments, limiting their access to the cytoplasm or the nucleus. Parenterally administered polynucleotides are also highly susceptible to rapid nuclease degradation both inside and outside the cytoplasm. Studies show rapid degradation of polynucleotides in blood after i.v. administration, with a half-life of about 30 minutes (Geary et al, J. Pharmacol. Exp. Ther. 296:890-897 (2001)).

Thus, the problems facing the delivery of polynucleotide, e.g., antisense oligonucleotide, can roughly be divided into two parts. First, the therapeutic polynucleotide must be formulated in such a way that it can be delivered to the cytoplasm and second, the polynucleotide must reach the cell nucleus intact and fully functional. Despite the advances in application of oligonucleotides and oligonucleotide analogs as therapeutics, the need exists for delivery systems providing improved pharmacological properties, e.g., serum stability, delivery to the right organ, tissue, or cell, and transmembrane delivery.

Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport. Accordingly, there is a need for delivery systems that can selectively direct charged therapeutic agents (e.g., antisense oligonucleotides such as antimirs) to specific target cells or tissues, and across permeation barriers (e.g., the plasma membrane or the BBB), while improving serum stability and/or resistance to endogenous lytic enzymes (e.g., RNases).

BRIEF SUMMARY

The present disclosure provides a cationic carrier unit comprising

[WP]-L1-[CC]-L2-[AM]     (Schema I)

or

[WP]-L1-[AM]-L2-[CC]     (Schema II)

wherein
WP is a water-soluble biopolymer moiety;
CC is a positively charged carrier moiety;
AM is an adjuvant moiety; and,
L1 and L2 are independently optional linkers, and
wherein when mixed with a nucleic acid at an ionic ratio of about 1:1, the cationic carrier unit forms a micelle.

In some aspects, the water-soluble polymer comprises poly(alkylene glycols), poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyglycerol, polyphosphazene, polyoxazolines ("POZ") poly(N-acryloylmorpholine), or any combinations thereof. In some aspects, the water-soluble polymer comprises polyethylene glycol ("PEG"), polyglycerol, or poly(propylene glycol) ("PPG"). In some aspects, the water-soluble polymer comprises:

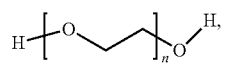

wherein n is 1-1000.

In some aspects, n is at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, at least about 125, at least about 126, at least about 127, at least about 128, at least about 129, at least about 130, at least about 131, at least about 132, at least about 133, at least about 134, at least about 135, at least about 136, at least about 137, at least about 138, at least about 139, at least about 140, or at least about 141. In some aspects, n is about 80 to about 90, about 90 to about 100, about 100 to about 110, about 110 to about 120, about 120 to about 130, about 140 to about 150, or about 150 to about 160.

In some aspects, the water-soluble polymer is linear, branched, or dendritic. In some aspects, the cationic carrier moiety comprises one or more basic amino acids. In some aspects, the cationic carrier moiety comprises at least three, at least four, at least five, at least six, at least seven, at least eight, at least nine, at least ten, at least 11, at least 12, at least 13, at least 14, at last 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, or at least 50 basic amino acids.

In some aspects, the cationic carrier moiety comprises about 30 to about 50 basic amino acids. In some aspects, the basic amino acid comprises arginine, lysine, histidine, or any combination thereof. In some aspects, the cationic carrier moiety comprises about 40 lysine monomers.

In some aspects, the adjuvant moiety is capable of modulating an immune response, an inflammatory response, or a tissue microenvironment. In some aspects, the adjuvant moiety is capable of modulating an immune response. In some aspects, the adjuvant moiety is capable of modulating a tumor microenvironment in a subject with a tumor.

In some aspects, the adjuvant moiety is capable of inhibiting or reducing hypoxia in the tumor microenvironment. In some aspects, the adjuvant moiety comprises an imidazole derivative, an amino acid, a vitamin, or any combination thereof.

In some aspects, the adjuvant moiety comprises:

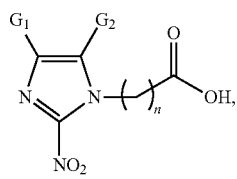

wherein
(i) each of $G_1$ and $G_2$ is independently selected from H, an aromatic ring, or 1-10 alkyl; or,
(ii) $G_1$ and $G_2$ together form an aromatic ring; and, wherein n is 1-10.

In some aspects, the adjuvant moiety comprises nitroimidazole. In some aspects, the adjuvant moiety comprises metronidazole, tinidazole, nimorazole, dimetridazole, pretomanid, ornidazole, megazol, azanidazole, benznidazole, or any combination thereof. In some aspects, the adjuvant moiety comprises an amino acid. In some aspects, the adjuvant moiety comprises

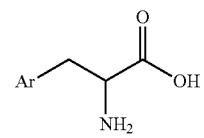

wherein Ar is

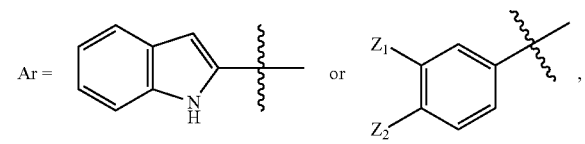

and
wherein each of $Z_1$ and $Z_2$ are independently selected from H and OH.

In some aspects, the adjuvant moiety is capable of inhibiting or reducing an inflammatory response. In some aspects, the adjuvant moiety is a vitamin. In some aspects, the vitamin comprises a cyclic ring or cyclic hetero atom ring and a carboxyl group or hydroxyl group.

In some aspects, the vitamin comprises:

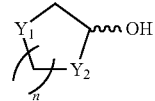

wherein each of $Y_1$ and $Y_2$ are independently selected from C, N, O, and S, and wherein n is 1 or 2.

In some aspects, the vitamin is selected from the group consisting of vitamin A, vitamin B1, vitamin B2, vitamin B3, vitamin B6, vitamin B7, vitamin B9, vitamin B12, vitamin C, vitamin D2, vitamin D3, vitamin E, vitamin M, vitamin H, and any combination thereof. In some aspects, the vitamin is vitamin B3.

In some aspects, the adjuvant moiety comprises at least about two, at least about three, at least about four, at least about five, at least about six, at least about seven, at least about eight, at least about nine, at least about ten, at least about 11, at least about 12, at least about 13, at least about 14, at least about 15, at least about 16, at least about 17, at least about 18, at least about 19, or at least about 20 vitamin B3 units. In some aspects, the adjuvant moiety comprises at least about 25, at least about 30, at least about 35, at least about 40, at least about 45, or at least about 50 vitamin B3 units. In some aspects, the adjuvant moiety comprises about 10 vitamin B3 units. In some aspects, the adjuvant moiety comprises about 20 vitamin B3 units. In some aspects, the adjuvant moiety comprises about 30 vitamin B3 units. In some aspects, the adjuvant moiety comprises about 40 vitamin B3 units.

In some aspects, the cationic carrier unit comprises about a water-soluble biopolymer moiety with about 120 to about 130 PEG units, a cationic carrier moiety comprising a poly-lysine with about 30 to about 40 lysine units, and an adjuvant moiety with about 5 to about 10 vitamin B3 units. In some aspects, the cationic carrier unit further comprises an anionic payload, which interacts with the cationic carrier unit via an ionic bond.

In some aspects, the cationic carrier unit comprises about a water-soluble biopolymer moiety with about 120 to about 130 PEG units, a cationic carrier moiety comprising a poly-lysine with about 70 to about 90 lysine units, e.g., about 80 lysine units, and an adjuvant moiety with about 20 to about 40 vitamin B3 units, e.g., about 30 vitamin B3 units. In some aspects, the cationic carrier unit further comprises an anionic payload, which interacts with the cationic carrier unit via an ionic bond.

The present disclosure also provides a micelle comprising the cationic carrier unit disclosed herein and an anionic payload, wherein the cationic carrier moiety of the cationic carrier complex and the anionic payload are associated with each other. In some aspects, the association is a covalent bond. In other aspects, the association is a non-covalent bond. In some aspects, the association is an ionic bond.

In some aspects, the positive charge of the cationic carrier moiety of the cationic carrier unit is sufficient to form a micelle when mixed with an anionic payload in a solution, wherein the overall ionic ratio of the positive charges of the cationic carrier moiety of the cationic carrier unit and the negative charges of the anionic payload in the solution is about 1:1. In some aspects, the cationic carrier unit is capable of protecting the anionic payload from degradation by a DNase and/or an RNase. In some aspects, the anionic payload is not conjugated to the cationic carrier unit by a covalent bond and/or the anionic payload interacts with the cationic carrier moiety of the cationic carrier unit only via an ionic interaction.

In some aspects, the half-life of the anionic payload is extended compared to the half-life of a free anionic payload not incorporated into a micelle. In some aspects, the positive charges of the cationic carrier moiety of the cationic carrier unit and the negative charges of the anionic payload in the micelle are at an ionic ratio of about 3:1, about 2.9:1, about 2.8:1, about 2.7:1, about 2.6:1, about 2.5:1, about 2.4:1, about 2.3:1, about 2.2:1, about 2:1, about 2:1, about 1.9:1, about 1.8:1, about 1.7:1, about 1.6:1, about 1.5:1, about 1.4:1, about 1.3:1, about 1.2:1, about 1.1:1, about 1:1, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8. about 1:2.9, or about 1:3. In some aspects, the positive charges of the cationic carrier moiety of the cationic carrier unit and the negative charges of the anionic payload in the micelle are at an ionic ratio of about 3:1 to about 1:3. In some aspects, the positive charges of the cationic carrier moiety of the cationic carrier unit and the negative charges of the anionic payload in the micelle are at a charge ratio of 1:1. In some aspects, the diameter of the micelle is between about 1 nm and 100 nm, between about 10 nm and about 100 nm, between about 10 nm and about 90 nm, between about 10 nm and about 80 nm, between about 10 nm and about 70 nm, between about 20 nm and about 100 nm, between about 20 nm and about 90 nm, between about 20 nm and about 80 nm, between about 20 nm and about 70 nm, between about 30 nm and about 100 nm, between about 30 nm and about 90 nm, between about 30 nm and about 80 nm, between about 30 nm and about 70 nm, between about 40 nm and about 100 nm, between about 40 nm and about 90 nm, between about 40 nm and about 80 nm, or between about 40 nm and about 70 nm.

In some aspects, the anionic payload comprises a nucleic acid. In some aspects, the nucleic acid comprises mRNA, miRNA, miRNA sponge, tough decoy miRNA, antimir, small RNA, rRNA, siRNA, shRNA, gDNA, cDNA, pDNA, PNA, BNA, antisense oligonucleotide (ASO), aptamer, cyclic dinucleotide, or any combination thereof. In some aspects, the nucleic acid comprises at least one nucleoside analog. In some aspects, the nucleoside analog comprises Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-0-methoxyethyl nucleic acid (2'-MOE), or any combination thereof.

In some aspects, the nucleic acid comprises a nucleotide sequence having 5 to 30 nucleotides in length. In some aspects, the nucleotide sequence is 7, 8, 9, 10, 11, 12, 13, 14, 15, 16, 17, 18, 19, 20, 21, 22, 23, 24, 25, or 26 nucleotides in length. In some aspects, the nucleotide sequence has a backbone, which comprises a phosphodiester linkage, a phosphotriester linkage, a methylphosphonate linkage, a phosphoramidate linkage, a phosphorothioate linkage, and combinations thereof. In some aspects, the cationic carrier unit further comprises a targeting moiety, which is linked to the water soluble polymer optionally via a linker.

In some aspects, the targeting moiety is capable of targeting a tissue. In some aspects, the tissue is liver, brain, kidney, lung, ovary, pancreas, thyroid, breast, stomach, or any combination thereof. In some aspects, the tissue is cancer tissue. In some aspects, the tissue is liver. In some aspects, the liver targeting moiety comprises cholesterol. In some aspects, the tissue is pancreas. In some aspects, the pancreas targeting moiety comprises a ligand binding to integrin receptors.

In some aspects, the targeting moiety targets the central nervous system. In some aspects, the brain targeting moiety is capable of being transported by large neutral amino acid transporter 1 (LAT1). In some aspects, the brain targeting moiety is an amino acid. In some aspects, the brain targeting moiety comprises a branched-chain or aromatic amino acid. In some aspects, the amino acid is valine, leucine, and/or isoleucine. In some aspects, the amino acid is tryptophan and/or tyrosine.

The present disclosure also provides a composition comprising the cationic carrier unit disclosed herein and a negatively charged molecule. Also provided is a pharmaceutical composition comprising a cationic carrier unit, composition, or micelle disclosed herein, and a pharmaceutically acceptable carrier.

The present disclosure also provides a method of preparing the cationic carrier unit disclosed herein comprising synthesizing the cationic carrier unit. In some aspects, the method of preparing a micelle disclosed herein comprises mixing the cationic carrier unit with the negatively charged molecule at an ionic ratio of 1:1 in solution. In some aspects, the method further comprises purifying the micelle.

The present disclosure also provides a method of treating a disease or condition in a subject in need thereof comprising administering a micelle of the present disclosure to the subject. In some aspects, the anionic payload in the core of the micelle exhibits a longer half-life than a corresponding anionic payload not integrated into a micelle. In some aspects, the subject is a mammal.

The present disclosure also provides a method of treating cancer in a subject in need thereof comprising administering a therapeutically effective amount of a micelle disclosed herein to the subject. In some aspects, the cancer is glioma, breast cancer, pancreatic cancer, liver cancer, skin cancer, or cervical cancer. In some aspects, the pancreatic cancer is pancreatic adenocarcinoma.

The present disclosure also provides a method to reduce inflammation in a subject suffering from a neurodegenerative disease comprising administering a therapeutically effective amount of a micelle disclosed herein to the subject.

The present disclosure also provides a method to recover and/or induce neurogenesis in a subject suffering from a neurodegenerative disease comprising administering a therapeutically effective amount of a micelle disclosed herein to the subject.

The present disclosure also provides a method to improve cognitive function in a subject suffering from a neurodegenerative disease comprising administering a therapeutically effective amount of a micelle disclosed herein to the subject.

In some aspects, the neurodegenerative disease is Alzheimer's disease.

The present disclosure also provides a method to reduce amyloid plaque burden in a subject suffering from Alzheimer's disease comprising administering a therapeutically effective amount of a micelle disclosed herein to the subject.

In some aspects, the micelle comprises a cationic carrier unit targeting LAT1 and a payload comprising an antisense oligonucleotide targeting miRNA-485-3p, e.g., an antisense oligonucleotide of SEQ ID NO: 18, or a fragment, variant, or derivative thereof. In some aspects, the fragment comprises 14, 15, 16, 17, 18, 19, 20, or 21 consecutive nucleotides of SEQ ID NO: 18. In some aspects, the variant has at least 70% sequence identity to SEQ ID NO: 18. In some aspects, the derivative comprises at least one sugar modification and/or at least one backbone modification.

BRIEF DESCRIPTION OF THE DRAWINGS

FIG. 17 shows a schematic representation of the experimental procedure. ASO-MDS micelles, i.e., micelles of the present disclosure comprising a LAT1 targeting moiety and antimir against miRNA 485-3p payload, were injected weekly for 4 weeks in 8 month old 5×FAD transgenic mice. ASO-MDS comprises (i) antimirs against miR485-3p and (ii) 100 cationic carrier units, in which each of the 50 cationic carrier units is linked to phenyl alanine (targeting moiety), and each of the 50 cationic carrier unit is not linked to any targeting moiety. Each of the cationic carrier units in ASO-MDS comprises $(PEG)_{5000}$ fused to 47 lysines, wherein each of 10 lysines are linked to nicotinamide, i.e., total 10 nicotinamides in a cationic carrier unit.

FIG. 18A shows the enhancement of phagocytosis of Aβ in mouse primary glial cells after ASO-MDS treatment.

FIG. 26A shows the timeline of the K-Ras gene silencing efficacy.

FIG. 26B shows a bar graph of the relative K-Ras mRNA after the K-Ras gene silencing treatment in FIG. 26A. For both FIGS. 26A and 26B, a oligonucleotide that is capable of inhibiting K-Ras was loaded in the micellar delivery system of the present disclosure. In order to target different tissues, the micellar delivery system of the present disclosure was fused to a cyclic RGD peptide (targeting α(v)β(3) integrin) or an X (target).

DETAILED DESCRIPTION

Figure 1:
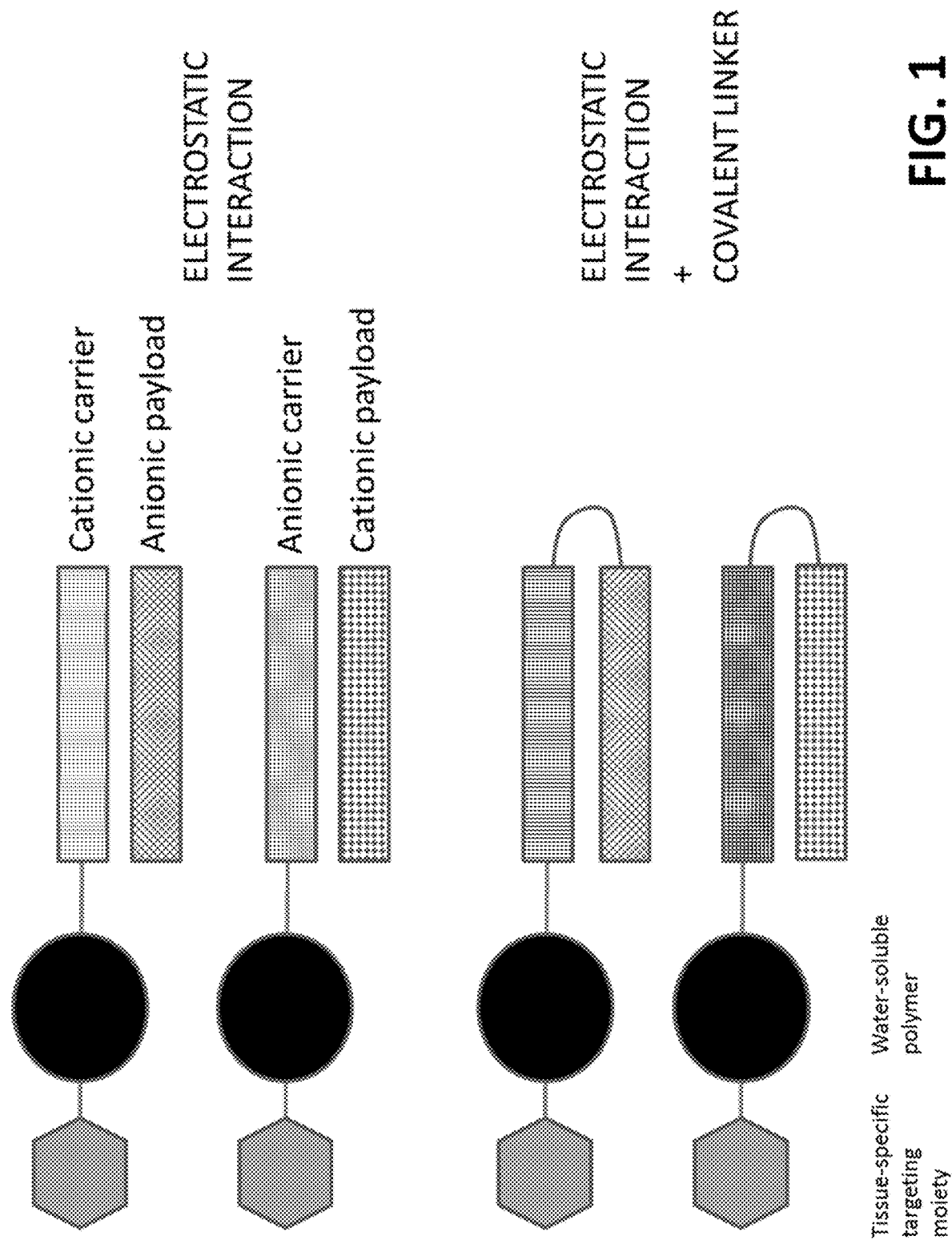
FIG. 1 shows exemplary architectures of carrier units of the present disclosure. The exemplary carrier units comprise an optional tissue-specific targeting moiety, water soluble polymer, and cationic or anionic carrier unit (which can, respectively, interact with anionic or cationic payloads). In some aspects, the cationic/anionic carrier and anionic/cationic payload are not tethered and interact electrostatically. In some aspects, the cationic/anionic carrier and anionic/cationic payload are tethered and interact electrostatically. For simplicity, the adjuvant moiety that can be between the water-soluble polymer and cationic/anionic carrier, or terminally after the cationic/anionic carrier, is not depicted in the drawing.

The present disclosure is directed to carrier units comprising a water-soluble biopolymer moiety (e.g., PEG) and a charged moiety (e.g., a polylysine). Upon electrostatic interaction between the charged moiety and a charged payload (e.g., an oligonucleotide) with an opposite charge and similar or identical charge load (i.e., the number of charges on the charged moiety of the carrier unit and on the charged payload is similar or identical), the charges in the charged moiety of the carrier unit and the charges in the charged payload neutralize each other yielding a carrier unit:payload complex. Carrier unit:payload complexes can self-associate to yield micelles in which the payload is located in the core of the micelle and the water-soluble biopolymer moiety is facing the solvent. In some aspects, the carrier unit comprises a cationic charged moiety, which can interact with anionic payloads. Conversely, the carrier unit can comprise an anionic charged moiety, which can interact with cationic payloads. Non-limiting examples of various aspects are shown in the present disclosure.

Before the present disclosure is described in greater detail, it is to be understood that this disclosure is not limited to the particular compositions or process steps described, as such can, of course, vary. As will be apparent to those of skill in the art upon reading this disclosure, each of the individual aspects described and illustrated herein has discrete components and features which can be readily separated from or combined with the features of any of the other several aspects without departing from the scope or spirit of the present disclosure. Any recited method can be carried out in the order of events recited or in any other order which is logically possible.

The headings provided herein are not limitations of the various aspects of the disclosure, which can be defined by reference to the specification as a whole. It is also to be understood that the terminology used herein is for the purpose of describing particular aspects only, and is not intended to be limiting, since the scope of the present disclosure will be limited only by the appended claims.

Accordingly, the terms defined immediately below are more fully defined by reference to the specification in its entirety.

I. Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation.

Nucleotides are referred to herein by their commonly known one-letter symbols recommended by the IUPAC-IUB Biochemical Nomenclature Commission. Accordingly, 'a' represents adenine, 'c' represents cytosine, 'g' represents guanine, 't' represents thymine, and 'u' represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The terms "administration," "administering," and grammatical variants thereof refer to introducing a composition, such as a micelle of the present disclosure, into a subject via a pharmaceutically acceptable route. The introduction of a composition, such as a micelle of the present disclosure, into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some aspects, two or more sequences are said to be "completely conserved" or "identical" if they are 100% identical to one another. In some aspects, two or more sequences are said to be "highly conserved" if they are at least 70% identical, at least 80% identical, at least 90% identical, or at least 95% identical to one another. In some aspects, two or more sequences are said to be "highly conserved" if they are about 70% identical, about 80% identical, about 90% identical, about 95% identical, about 98% identical, or about 99% identical to one another. In some aspects, two or more sequences are said to be "conserved" if they are at least 30% identical, at least 40% identical, at least 50% identical, at least 60% identical, at least 70% identical, at least 80% identical, at least 90% identical, or at least 95% identical to one another. In some aspects, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

The term "derived from," as used herein, refers to a component that is isolated from or made using a specified molecule or organism, or information (e.g., amino acid or nucleic acid sequence) from the specified molecule or organism. For example, a nucleic acid sequence that is derived from a second nucleic acid sequence can include a nucleotide sequence that is identical or substantially similar to the nucleotide sequence of the second nucleic acid sequence. In the case of nucleotides or polypeptides, the derived species can be obtained by, for example, naturally occurring mutagenesis, artificial directed mutagenesis or artificial random mutagenesis. The mutagenesis used to derive nucleotides or polypeptides can be intentionally directed or intentionally random, or a mixture of each. The mutagenesis of a nucleotide or polypeptide to create a different nucleotide or polypeptide derived from the first can be a random event (e.g., caused by polymerase infidelity) and the identification of the derived nucleotide or polypeptide can be made by appropriate screening methods, e.g., as discussed herein. Mutagenesis of a polypeptide typically entails manipulation of the polynucleotide that encodes the polypeptide. In some aspects, a nucleotide or amino acid sequence that is derived from a second nucleotide or amino acid sequence has a sequence identity of at least about 50%, at least about 51%, at least about 52%, at least about 53%, at least about 54%, at least about 55%, at least about 56%, at least about 57%, at least about 58%, at least about 59%, at least about 65%, at least about 66%, at least about 62%, at least about 63%, at least about 64%, at least about 65%, at least about 66%, at least about 67%, at least about 68%, at least about 69%, at least about 75%, at least about 76%, at least about 72%, at least about 73%, at least about 74%, at least about 75%, at least about 76%, at least about 77%, at least about 78%, at least about 79%, at least about 85%, at least about 86%, at least about 82%, at least about 83%, at least about 84%, at least about 85%, at least about 86%, at least about 87%, at least about 88%, at least about 89%, at least about 95%, at least about 96%, at least about 92%, at least about 93%, at least about 94%, at least about 95%, at least about 96%, at least about 97%, at least about 98%, at least about 99%, or about 100% to the second nucleotide or amino acid sequence, respectively, wherein the first nucleotide or amino acid sequence retains the biological activity of the second nucleotide or amino acid sequence.

The terms "complementary" and "complementarity" refer to two or more oligomers (i.e., each comprising a nucleobase sequence), or between an oligomer and a target gene, that are related with one another by Watson-Crick base-pairing rules. For example, the nucleobase sequence "T-G-A (5'→3')," is complementary to the nucleobase sequence "A-C-T (3'→5')." Complementarity may be "partial," in which less than all of the nucleobases of a given nucleobase sequence are matched to the other nucleobase sequence according to base pairing rules. For example, in some aspects, complementarity between a given nucleobase sequence and the other nucleobase sequence may be about 70%, about 75%, about 80%, about 85%, about 90% or about 95%. Or, there may be "complete" or "perfect" (100%) complementarity between a given nucleobase sequence and the other nucleobase sequence to continue the example. The degree of complementarity between nucleobase sequences has significant effects on the efficiency and strength of hybridization between the sequences.

The term "downstream" refers to a nucleotide sequence that is located 3' to a reference nucleotide sequence. In certain aspects, downstream nucleotide sequences relate to sequences that follow the starting point of transcription. For example, the translation initiation codon of a gene is located downstream of the start site of transcription.

The terms "excipient" and "carrier" are used interchangeably and refer to an inert substance added to a pharmaceutical composition to further facilitate administration of a compound.

As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some aspects, polymeric molecules are considered to be "homologous" to one another if at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of the monomers in the molecule are identical (exactly the same monomer) or are similar (conservative substitutions). The term "homologous" necessarily refers to a comparison between at least two sequences (polynucleotide or polypeptide sequences).

As used herein, the term "identity" refers to the overall monomer conservation between polymeric molecules, e.g., between polypeptide molecules or polynucleotide molecules (e.g. DNA molecules and/or RNA molecules). The term "identical" without any additional qualifiers, e.g., protein A is identical to protein B, implies the sequences are 100% identical (100% sequence identity). Describing two sequences as, e.g., "70% identical," is equivalent to describing them as having, e.g., "70% sequence identity."

Calculation of the percent identity of two polypeptide or polynucleotide sequences, for example, can be performed by aligning the two sequences for optimal comparison purposes (e.g., gaps can be introduced in one or both of a first and a second polypeptide or polynucleotide sequences for optimal alignment and non-identical sequences can be disregarded for comparison purposes). In certain aspects, the length of a sequence aligned for comparison purposes is at least about 30%, at least about 40%, at least about 50%, at least about 60%, at least about 70%, at least about 80%, at least about 90%, at least about 95%, or about 100% of the length of the reference sequence. The amino acids at corresponding amino acid positions, or bases in the case of polynucleotides, are then compared.

When a position in the first sequence is occupied by the same amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity (% ID) or of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

As used herein, the terms "isolated," "purified," "extracted," and grammatical variants thereof are used interchangeably and refer to the state of a preparation of desired composition of the present disclosure, that has undergone one or more processes of purification. In some aspects, isolating or purifying as used herein is the process of removing, partially removing (e.g., a fraction) of a composition of the present disclosure from a sample containing contaminants. In some aspects, an isolated composition has no detectable undesired activity or, alternatively, the level or amount of the undesired activity is at or below an acceptable level or amount. In other aspects, an isolated composition has an amount and/or concentration of desired composition of the present disclosure, at or above an acceptable amount and/or concentration and/or activity. In other aspects, the isolated composition is enriched as compared to the starting material from which the composition is obtained. This enrichment can be by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%, at least about 99.9999%, or greater than 99.9999% as compared to the starting material. In some aspects, isolated preparations are substantially free of residual biological products. In some aspects, the isolated preparations are 100% free, at least about 99% free, at least about 98% free, at least about 97% free, at least about 96% free, at least about 95% free, at least about 94% free, at least about 93% free, at least about 92% free, at least about 91% free, or at least about 90% free of any contaminating biological matter. Residual biological products can include abiotic materials (including chemicals) or unwanted nucleic acids, proteins, lipids, or metabolites.

The term "linked" as used herein refers to a first amino acid sequence or polynucleotide sequence covalently or non-covalently joined to a second amino acid sequence or polynucleotide sequence, respectively. The first amino acid or polynucleotide sequence can be directly joined or juxtaposed to the second amino acid or polynucleotide sequence or alternatively an intervening sequence can covalently join the first sequence to the second sequence. The term "linked" means not only a fusion of a first polynucleotide sequence to a second polynucleotide sequence at the 5'-end or the 3'-end, but also includes insertion of the whole first polynucleotide sequence (or the second polynucleotide sequence) into any two nucleotides in the second polynucleotide sequence (or the first polynucleotide sequence, respectively). The first polynucleotide sequence can be linked to a second polynucleotide sequence by a phosphodiester bond or a linker. The linker can be, e.g., a polynucleotide.

The terms "miRNA" or "miR" or "microRNA" are used interchangeably and refer to a microRNA molecule found in eukaryotes that is involved in RNA-based gene regulation. The term will be used to refer to the single-stranded RNA molecule processed from a precursor. Names of miRNAs and their sequences related to the present disclosure are provided herein. MicroRNAs recognize and bind to target mRNAs through imperfect base pairing leading to destabilization or translational inhibition of the target mRNA and thereby downregulate target gene expression. Conversely, targeting miRNAs via molecules comprising a miRNA binding site (generally a molecule comprising a sequence complementary to the seed region of the miRNA) can reduce or inhibit the miRNA-induced translational inhibition leading to an upregulation of the target gene.

The terms "mismatch" or "mismatches" refer to one or more nucleobases (whether contiguous or separate) in an oligomer nucleobase sequence that are not matched to a target pre-mRNA according to base pairing rules. While perfect complementarity is often desired, some aspects can include one or more but preferably 6, 5, 4, 3, 2, or 1 mismatches with respect to the target pre-mRNA. Variations at any location within the oligomer are included. In certain aspects, antisense oligomers of the disclosure include variations in nucleobase sequence near the termini, variations in the interior, and if present are typically within about 6, 5, 4, 3, 2, or 1 subunits of the 5' and/or 3' terminus. In certain aspects, one, two, or three nucleobases can be removed and still provide on-target binding.

As used herein, the terms "modulate," "modify," and grammatical variants thereof, generally refer when applied to a specific concentration, level, expression, function or behavior, to the ability to alter, by increasing or decreasing, e.g., directly or indirectly promoting/stimulating/up-regulating or interfering with/inhibiting/down-regulating the specific concentration, level, expression, function or behavior, such as, e.g., to act as an antagonist or agonist. In some instances, a modulator can increase and/or decrease a certain concentration, level, activity or function relative to a control, or relative to the average level of activity that would generally be expected or relative to a control level of activity.

"Nucleic acid," "nucleic acid molecule," "nucleotide sequence," "polynucleotide," and grammatical variants thereof are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Single stranded nucleic acid sequences refer to single-stranded DNA (ssDNA) or single-stranded RNA (ssRNA). Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the disclosure comprises one or more nucleic acids as described herein.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The terms "pharmaceutically-acceptable carrier," "pharmaceutically-acceptable excipient," and grammatical variations thereof, encompass any of the agents approved by a regulatory agency of the U.S. Federal government or listed in the U.S. Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "pharmaceutical composition" refers to one or more of the compounds described herein, such as, e.g., a micelle of the present disclosure, mixed or intermingled with, or suspended in one or more other chemical components, such as pharmaceutically-acceptable carriers and excipients. One purpose of a pharmaceutical composition is to facilitate administration of preparations of micelles to a subject.

The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA.

In some aspects of the present disclosure a polynucleotide can be, e.g., an oligonucleotide, such as an antisense oligonucleotide. In some aspects, the oligonucleotide is an RNA. In some aspects, the RNA is a synthetic RNA. In some aspects, the synthetic RNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine).

The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art. The term "polypeptide," as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multichain polypeptides. Most commonly, disulfide linkages are found in multichain polypeptides. The term polypeptide can also apply to amino acid polymers in which one or more amino acid residues are an artificial chemical analogue of a corresponding naturally occurring amino acid. In some aspects, a "peptide" can be less than or equal to 50 amino acids long, e.g., about 5, 10, 15, 20, 25, 30, 35, 40, 45, or 50 amino acids long.

The terms "prevent," "preventing," and variants thereof as used herein, refer partially or completely delaying onset of an disease, disorder and/or condition; partially or completely delaying onset of one or more symptoms, features, or clinical manifestations of a particular disease, disorder, and/or condition; partially or completely delaying onset of one or more symptoms, features, or manifestations of a particular disease, disorder, and/or condition; partially or completely delaying progression from a particular disease, disorder and/or condition; and/or decreasing the risk of developing pathology associated with the disease, disorder, and/or condition. In some aspects, preventing an outcome is achieved through prophylactic treatment.

As used herein, "prophylactic" refers to a therapeutic or course of action used to prevent the onset of a disease or condition, or to prevent or delay a symptom associated with a disease or condition.

As used herein, a "prophylaxis" refers to a measure taken to maintain health and prevent or delay the onset of a bleeding episode, or to prevent or delay symptoms associated with a disease or condition.

As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art. It is understood that percentage of similarity is contingent on the comparison scale used, i.e., whether the amino acids are compared, e.g., according to their evolutionary proximity, charge, volume, flexibility, polarity, hydrophobicity, aromaticity, isoelectric point, antigenicity, or combinations thereof.

The terms "subject," "patient," "individual," and "host," and variants thereof are used interchangeably herein and refer to any mammalian subject, including without limitation, humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired, particularly humans. The methods described herein are applicable to both human therapy and veterinary applications.

As used herein, the phrase "subject in need thereof" includes subjects, such as mammalian subjects, that would benefit from administration of a micelle of the disclosure, e.g., to improve hemostasis.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

As used herein the term "therapeutically effective amount" is the amount of reagent or pharmaceutical compound comprising a micelle of the present disclosure that is sufficient to a produce a desired therapeutic effect, pharmacologic and/or physiologic effect on a subject in need thereof. A therapeutically effective amount can be a "prophylactically effective amount" as prophylaxis can be considered therapy.

The terms "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

The term "upstream" refers to a nucleotide sequence that is located 5' to a reference nucleotide sequence.

II. Carrier Units

The present disclosure provides carrier units that can self-assemble into micelles or be incorporated into micelles. Carrier units of the present disclosure comprise a water-soluble biopolymer moiety (e.g., PEG) and a charged carrier moiety. In some aspects, the charged carrier moiety is cationic (e.g., a polylysine), whereas in other aspects the charged carrier moiety is anionic (e.g., a polyglutamic acid) as exemplified in FIG. 1.

Carrier units of the present disclosure can be used to deliver charged payloads (e.g., therapeutic or diagnostic agents). Carrier units with a cationic charged carrier moiety can be used for the delivery of anionic payloads, e.g., polynucleotides. Carrier units with an anionic charged carrier moiety can be used for the delivery of cationic payloads, e.g., positively charged small molecule drugs. See FIG. 1.

Figure 2:
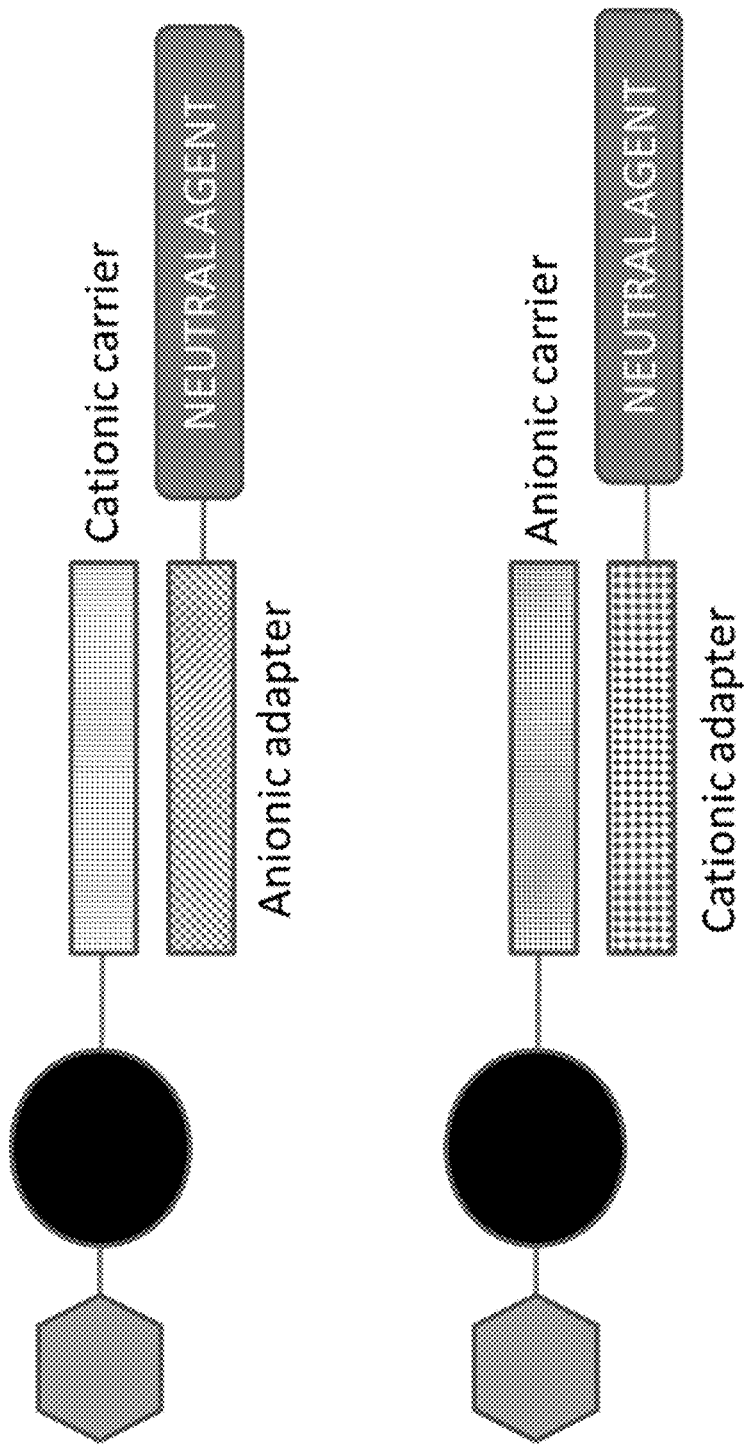
FIG. 2 shows an alternative method for loading neutral payload using the carrier units of the present disclosure in which the neutral payload (e.g., a hydrophobic therapeutic agent) is covalently attached to an adapter, which in turn can interact electrostatically with the cationic or anionic carrier moiety of the carrier unit.

Neutral or hydrophobic payloads can also be delivered using the carrier units of the present disclosure by using an adapter (e.g., a cationic or an anionic adapter as depicted in FIG. 2). Adapters bind covalently, e.g., to a hydrophobic payload and provide such payload with the appropriate charge load to interact with the charged carrier moiety of a carrier unit of the present disclosure. Thus, in some aspects, the payload of the present disclosure can comprise a charged moiety (the "adapter" moiety) that can interact with the charged carrier moiety of a carrier unit of the present disclosure (e.g., via electrostatic interaction), and a biologically active moiety (e.g., a therapeutic moiety). In some aspects, the adapter moiety and the biologically active moiety are connected directly, whereas in some other aspects they can be connected via a linker.

Upon electrostatic interaction between
(i) a charged carrier moiety; and,
(ii) a charged payload (e.g., a nucleotide sequence, e.g., an oligonucleotide, an siRNA, an shRNA, etc.) or a charged portion thereof (e.g., an adapter moiety), wherein
   a. the charged carrier moiety and the charged payload or charged portion thereof have different net charges (i.e., one is cationic and the other is anionic); and
   b. the net charge loads are similar or identical (i.e., the number of charges on the charged moiety of the carrier unit and on the charged payload or charged portion thereof is similar or identical),
the charges in the charged moiety and the charges in the charged payload or adapter neutralize each other yielding a carrier unit:payload complex.

The resulting carrier unit:payload complex is amphipathic, having a hydrophilic "head" comprising the water-soluble biopolymer moiety and a hydrophobic "tail" comprising the charged carrier moiety electrostatically bound to the payload.

Carrier unit:payload complexes can self-associate, alone or in combination with other amphipathic molecules, to yield micelles in which the payload is located in the core of the micelle and the water-soluble biopolymer moiety is facing the solvent. The term "micelles of the present disclosure" encompasses not only classic micelles but also small particles, small micelles, micelles, rod-like structures, or polymersomes. Given that polymersomes comprise a luminal space, it is to be understood that all the disclosures related to the "core" of classic micelles are equally applicable to the luminal space in polymersomes comprising carrier units of the present disclosure. Thus, in some aspects, the micelles of the present disclosure can comprise payload molecules attached to carrier units of the present disclosure and payload molecules in the luminal space of the micelle (e.g, the lumen of a polymersome). In some aspects, the payload attached to the carrier units and the payload in the luminal space are the same. In some aspects, the payload attached to the carrier units and the payload in the luminal space are different.

The carrier units of the present disclosure can also comprise a targeting moiety covalently linked to the water-soluble biopolymer moiety via one or more optional linkers. Once a micelle is formed, the targeting moiety is located on the surface of the micelle and can deliver the micelle to a specific target tissue, to a specific cell type, and/or facilitate transport across a physiological barrier (e.g., cell plasma membrane or BBB). In some aspects, the micelles of the present disclosure can comprises more than one type of targeting moiety.

The carrier units of the present disclosure can also comprise an adjuvant moiety covalently linked to the charged carrier moiety. The adjuvant moiety can serve a dual purpose: it can provide charges for the electrostatic interaction with the payload and/or can have, e.g., a therapeutic, a co-therapeutic effect, or positively affect the homeostasis of the target cell or target tissue.

As shown in schematic form in FIG. 1, in some aspects, the payload is not covalently linked to the carrier unit. However, in other aspects, the payload can be covalently linked to the carrier unit, e.g., a linker such as cleavable linker.

Non-limiting examples of various aspects are shown in the present disclosure. The disclosure refers in particular to the use of cationic carrier units, e.g., to deliver anionic payloads such as nucleic acids. However, it would be apparent to a person of ordinary skill in the art that the disclosures can be equally applied to the delivery of cationic payloads or to the delivery of neutral payloads by reversing the charges of the carrier moiety and payload (i.e., using an anionic carrier moiety in the carrier unit to deliver a cationic payload), or by using a neutral payload linked to a cationic or anionic adapter that would electrostatically interact with an anionic or cationic carrier moiety, respectively.

Accordingly, in one aspect, the present disclosure provides cationic carrier units of Schema I or Schema II

[WP]-L1-[CC]-L2-[AM]  (Schema I)

[WP]-L1-[AM]-L2-[CC]  (Schema II)

wherein
   WP is a water-soluble biopolymer moiety (e.g., PEG);
   CC is a cationic carrier moiety, e.g., a polylysine;

AM is an adjuvant moiety, e.g., vitamin, e.g., vitamin B3; and,

L1 and L2 are independently optional linkers.

The present disclosure also provides anionic carrier units of Schema III or Schema IV

[WP]-L1-[AC]-L2-[AM]   (Schema III)

[WP]-L1-[AM]-L2-[AC]   (Schema IV)

wherein
WP is a water-soluble biopolymer moiety (e.g., PEG);
AC is an anionic carrier moiety;
AM is an adjuvant moiety; and,
L1 and L2 are independently optional linkers.

The present disclosure also provides cationic and anionic carrier units of Schemas V to VIII

[WP]-L1-[AC]-L2-[AM]-L3-[P]   (Schema V)

[WP]-L1-[AM]-L2-[AC]-L3-[P]   (Schema VI)

[WP]-L1-[AC]-L2-[AM]-L3-[P]   (Schema VII)

[WP]-L1-[AM]-L2-[AC]-L3-[P]   (Schema VIII)

wherein
WP is a water-soluble biopolymer moiety (e.g., PEG);
AC is a anionic carrier moiety;
CC is a cationic carrier moiety;
AM is an adjuvant moiety;
L1 and L2 are independently optional linkers;
L3 is an optional linker that can be cleavable; and,
P is a payload.

In some aspects of the constructs of Schema I to VIII shown above, the [WP] component can be connected to at least one targeting moiety, i.e., [T]$_n$-[WP]- . . . wherein n is an integer, e.g., 1, 2 or 3.

Figure 3:
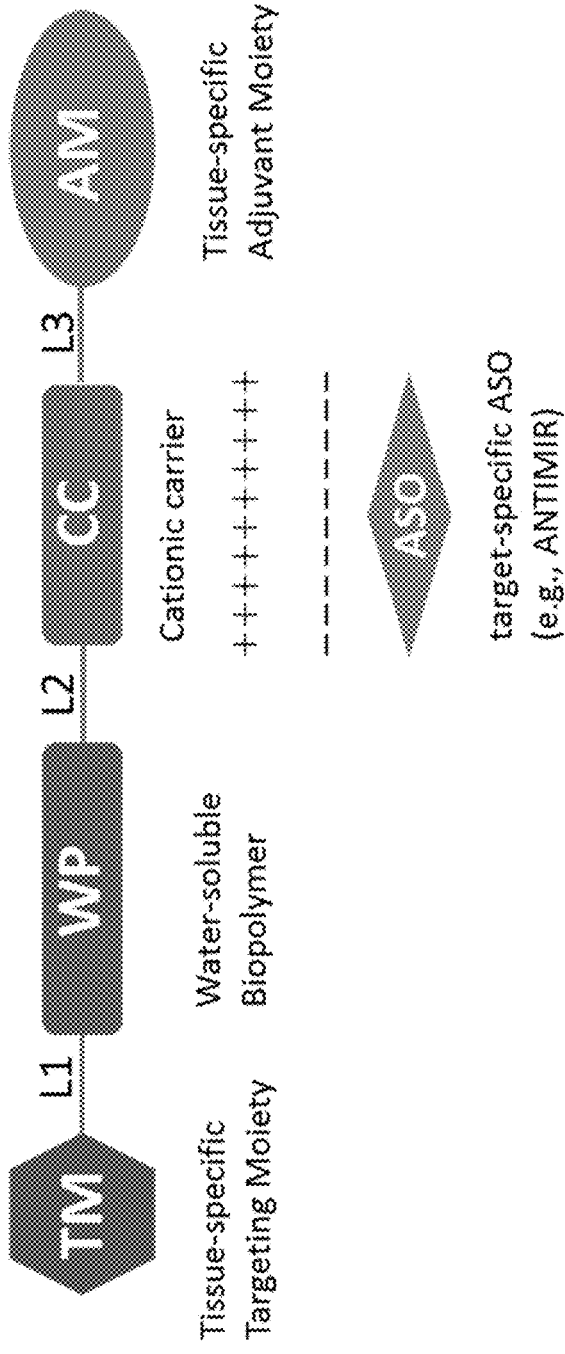
FIG. 3 shows an exemplary architecture of a carrier unit of the present disclosure. The example presented includes a cationic carrier moiety, which can interact electrostatically with anionic payloads, e.g., nucleic acids such as antisense oligonucleotides targeting a gene, e.g., miRNA (antimirs). In some aspects, AM can be located between WP and CC. The CC and AM components are portrayed in a linear arrangement for simplicity. However, as exemplified in FIG. 4, CC and AM can be arranged in a scaffold fashion.
Figure 4:
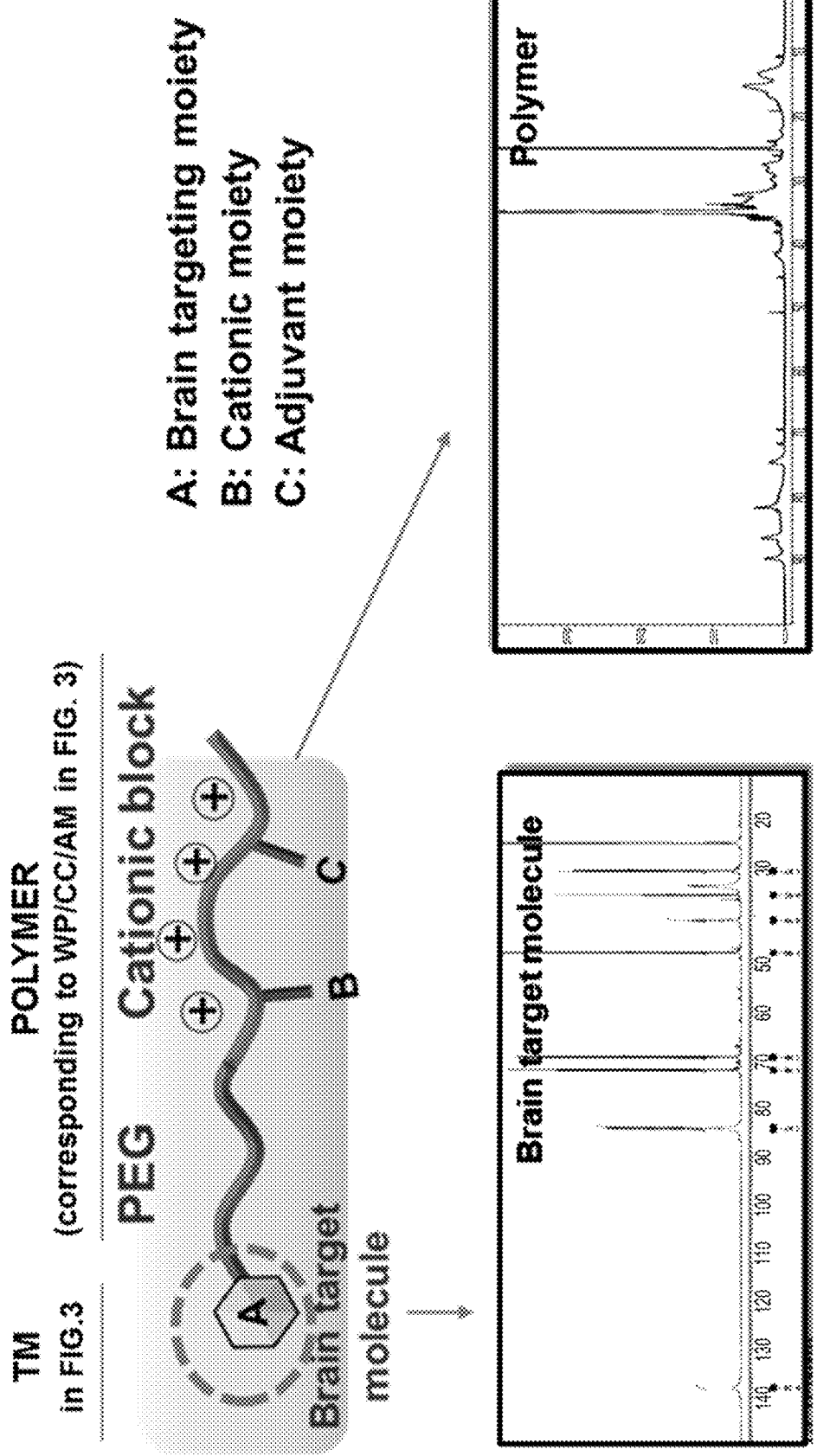
FIG. 4 shows $^1$H-NMR characteristics of a carrier unit comprising a brain targeting moiety, which can form micellar structures after binding to an anionic payload. The $^1$H-NMR chart corresponding to the brain-targeting moiety (labeled "brain target molecule") shows that that the brain-targeting moiety (an amino acid moiety containing a ring structure that binds to the LAT1 target on the brain endothelium) was successfully synthesized. A second $^1$H-NMR chart (labeled "polymer") shows that the cationic PEG block copolymer (comprising also the cationic carrier moiety and adjuvant moiety) was also synthesized.
Figure 5:
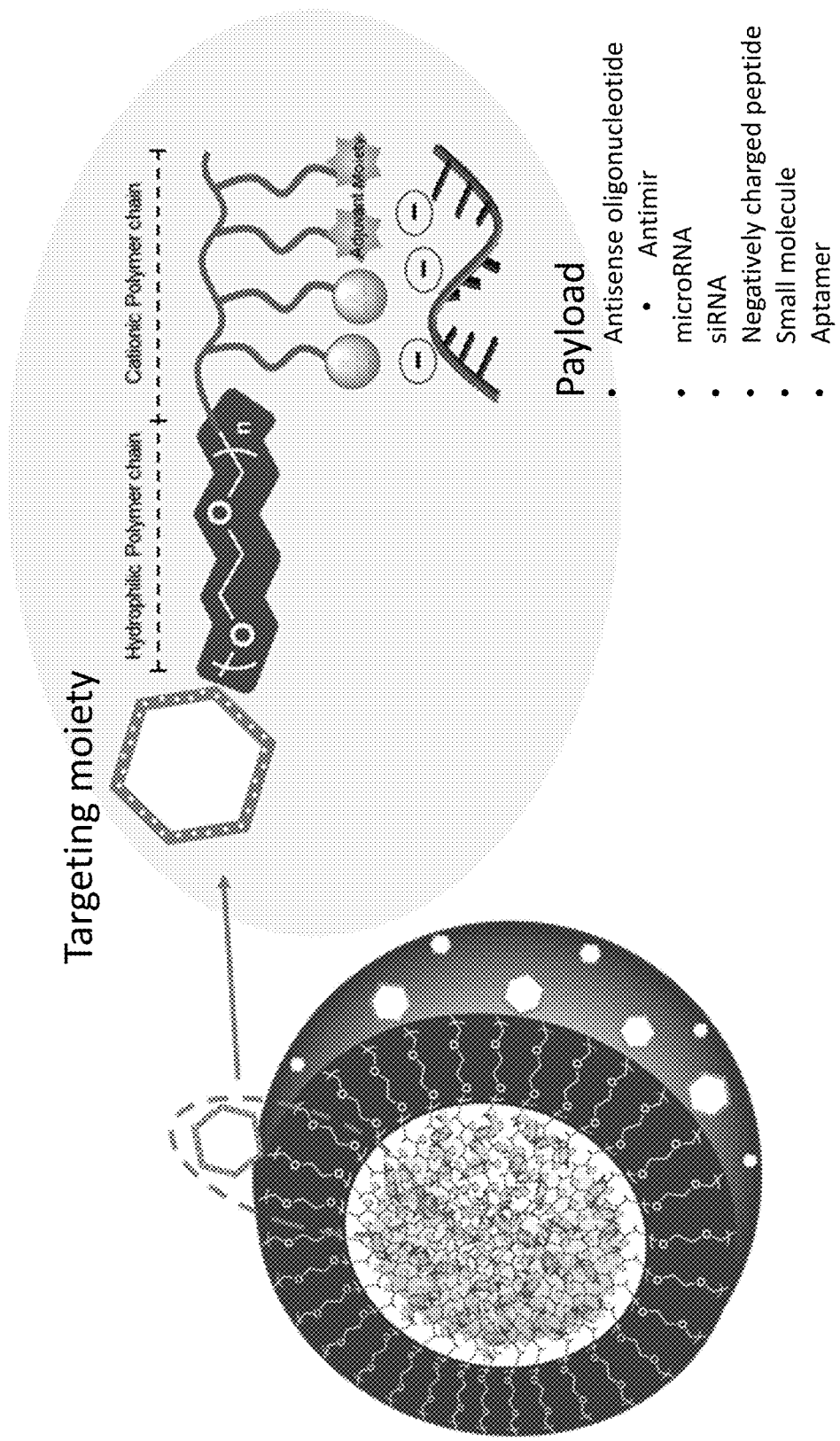
FIG. 5 is a schematic representation showing how carrier units of the present disclosure are inserted in a micelle, in which the tissue specific targeting moiety would decorate the external surface of the micelle, and the nucleic acid payload would be located, e.g., at the core of the micelle (Polyion complex antisense oligonucleotide).

FIG. 3 presents a schematic representation of a cationic carrier unit of the present disclosure. For simplicity, the unit in FIG. 3 has been represented linearly. However, in some aspects, the carrier units can comprises the CC and AM moieties organized in a branched scaffold arrangement (see FIG. 4 and FIG. 5), for example, with a polymeric CC moiety comprising positively charged units and AM attached at one or more points along the CC moiety. In other aspects, CC and AM can be attached to a scaffolding moiety, as shown in FIG. 5.

In some aspects, the carrier units of the present disclosure comprises:

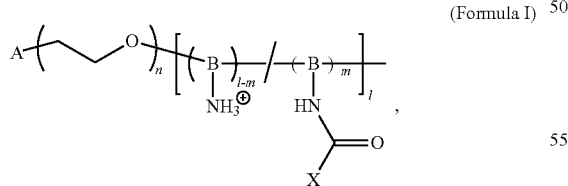
(Formula I)

A is a targeting moiety, e.g., a molecule targeting a LAT1 transporter,
B are cationic polymer blocks in a cationic carrier moiety, wherein,
(i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

(ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and, (iii) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

and wherein X is an adjuvant moiety, for example, a vitamin, e.g.

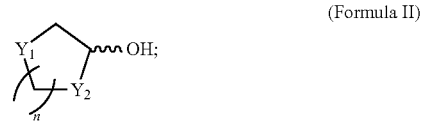
(Formula II)

wherein Y1 is C, N, O, or S, and Y2 is C, N O, or S, and n is 1 or 2. In some aspects, X can be —SH (e.g., sulfanyl group, alkanethiols or alkyl thiols). In some aspects, the micelle of the present disclosure comprises one type of cationic carrier units conjugated to a vitamin, e.g., vitamin B3, and another type of cationic carrier units conjugated to a sulfanyl group (e.g., alkanethiols or alkyl thiols). In some aspects, the micelle of the present disclosure comprises a first type of cationic carrier units conjugated to a vitamin, e.g., vitamin B3, a second type of cationic carrier units conjugated to a sulfanyl group (e.g., alkanethiols or alkyl thiols); and a third type of cationic carrier units that are a free base.

When cationic carrier units of the present disclosure are mixed with an anionic payload (e.g., a nucleic acid) at an ionic ratio of about 1:about 1, i.e., the number of negative charges in the anionic payload and the number of positive charges in the cationic carrier moiety are about the same, the neutralization of negative charges in the anionic payload by positive charges in the cationic carrier moiety mainly via electrostatic interaction leads to the formation of a cationic carrier unit:anionic payload complex having an unaltered hydrophilic portion (comprising the WP moiety) and a substantially more hydrophobic portion (resulting from the association between the cationic carrier moiety plus adjuvant moiety and the anionic payload).

In some aspects, the adjuvant moiety can contribute its own positive charges to the positive charges of the cationic carrier moiety, which would interact with the negative charges of the anionic payload. It is to be understood that references to the interactions (e.g., electrostatic interactions) between a cationic carrier moiety and an anionic payload also encompass interactions between the charges of a cationic carrier moiety plus adjuvant moiety and the charges of an anionic payload.

The increase in the hydrophobicity of the cationic carrier moiety of the cationic carrier unit due to the neutralization of its positive charges via electrostatic interaction with the negative charges of the anionic payload results in an amphipathic complex. Such amphipathic complexes can self-organize, alone or combination with other amphipathic components, into micelles. The resulting micelles comprise the WP moieties facing the solvent (i.e., the WP moieties are facing the external surface of the micelle), whereas the CC and AM moieties as well as the associate payload (e.g., a nucleotide sequence, e.g., an oligonucleotide, an siRNA, an shRNA, an "antimir", or any combination thereof) are in the core of the micelle.

In some specific aspects, the cationic carrier unit comprises:
(a) a WP moiety, wherein the water-soluble biopolymer is a polyethylene glycol (PEG) of formula III (see below), wherein n is between about 120 to about PEG 130 (e.g., PEG is a PEG5000 or a PEG6000);
(b) a CC moiety, wherein the cationic carrier moiety comprises, e.g., about 30 to about 40 lysines (e.g., a linear poly(L-lysine)n wherein n is between about 30 and about 40), a polyethyleneimine (PEI), or chitosan; and,
(c) an AM moiety, wherein the adjuvant moiety has about 5 to about 10 vitamin B3 units (e.g., about 5 to about 10 concatenated vitamin B3 units).

In some specific aspects, the cationic carrier unit comprises:
(a) a WP moiety, wherein the water-soluble biopolymer is a polyethylene glycol (PEG) of formula III (see below), wherein n is between about 120 to about PEG 130 (e.g., PEG is a PEG5000 or a PEG6000);
(b) a CC moiety, wherein the cationic carrier moiety comprises, e.g., about 60 to about 100 lysines (e.g., a linear poly(L-lysine)n wherein n is between about 60 and about 100), e.g., about 70 to 90 lysines, about 80 lysines, a polyethyleneimine (PEI), or chitosan; and,
(c) an AM moiety, wherein the adjuvant moiety has about 10 to about 50 vitamin B3 units (e.g., about 10 to about 50 concatenated vitamin B3 units, about 20 to 40 units, e.g., about 30 units).

In some aspects, the cationic carrier unit further comprises at least one targeting moiety attached to the WP moiety of the cationic carrier unit. In some aspects, the number and/or density of targeting moieties displayed on the surface of the micelle can be modulated by using a specific ratio of cationic carrier units having targeting moieties to cationic carrier units not having targeting moieties. In some aspects, the ratio of cationic carrier units having a targeting moiety to cationic carrier units not having a targeting moiety is at least about 1:5, at least about 1:10, at least about 1:20, at least about 1:30, at least about 1:40, at least about 1:50, at least about 1:60, at least about 1:70, at least about 1:80, at least about 1:90, at least about 1:100, at least about 1:120, at least about 1:140, at least about 1:160, at least about 1:180, at least about 1:200, at least about 1:250, at least about 1:300, at least about 1:350, at least about 1:400, at least about 1:450, at least about 1:500, at least about 1:600, at least about 1:700, at least about 1:800, at least about 1:900, or at least about 1:1000.

In some aspects, the cationic carrier unit comprises
(i) a targeting moiety (A) which targets the transporter LAT1 (e.g., phenylalanine),
(ii) a water soluble polymer which is PEG,
(iii) a cationic carrier moiety comprising cationic polymer blocks which are lysine, and
(iv) two or more adjuvant moieties which are vitamin B3.

In some aspects, the cationic carrier unit comprises
(i) a targeting moiety (A) which targets the transporter LAT1 (e.g., phenylalanine),
(ii) a water soluble polymer which is PEG, wherein n=100-200, e.g., 100-150, e.g., 120-130,
(iii) a cationic carrier moiety comprising cationic polymer blocks, e.g., polylysine, and
(iv) two or more adjuvant moieties, e.g., vitamin B3.

In some aspects, the cationic carrier unit comprises
(i) a targeting moiety (A) which targets the transporter LAT1 (e.g., phenylalanine),
(ii) a water soluble polymer which is PEG, wherein n=100-200, e.g., 100-150, e.g., 120-130,
(iii) a cationic carrier moiety comprising cationic polymer blocks, e.g., 10-100 lysines, e.g., 10-50 lysines, e.g., 30-40 lysines, e.g., 70-80 lysines, and
(iv) two or more adjuvant moieties, e.g., vitamin B3, e.g., 25-30 vitamin B3.

In some aspects, the cationic carrier unit comprises
(i) a targeting moiety (A) which targets the transporter LAT1 (e.g., phenylalanine),
(ii) a water soluble polymer which is PEG, wherein n=100-200, e.g., 100-150, e.g., 120-130,
(iii) a cationic carrier moiety comprising cationic polymer blocks, e.g., 10-100 lysines, e.g., 10-50 lysines, e.g., 30-40 lysines, e.g., 70-80 lysines, and
(iv) two or more adjuvant moieties, e.g., 5-50 vitamin B3, e.g., 5-30 vitamin B3, e.g., 5-20 vitamin B3, e.g., 5-15 vitamin B3, e.g., 5-10 vitamin B3, e.g., 25-30 vitamin B3.

As exemplified in (Schema I), the CC moiety can be a polymer comprising a number of B units (wherein each B unit could be, e.g., lysine) and the AM moiety can be a non-discrete molecular entity comprising a number of X units (e.g., vitamin units) covalently attached to side chain attachment points on the CC moiety. Thus, in a specific aspect, the cationic carrier unit comprises
(i) a targeting moiety (A) which targets the transporter LAT1 (e.g., phenylalanine),
(ii) a water soluble polymer which is PEG, wherein n=120-130,
(iii) a cationic carrier moiety comprising 30-40, 40-50, 50-60, or 70-80 B cationic polymer blocks which are lysine, and
(iv) 5-10, 10-20, 20-25, or 25-30 X adjuvant moieties which are vitamin B3.

In some aspects, the cationic carrier unit of the present disclosure interacts with an antisense oligonucleotide payload targeting miR-485-3p, e.g., AGAGAGGAGAGCCGUGUAUGAC (SEQ ID NO: 18). In some aspects, the carrier unit complexed the payload forms a micelle.

In some aspects, the vitamin B3 unit are introduced into the side chains of the CC moiety, e.g., by a coupling reaction between $NH_2$ groups in the lysines and COOH groups of vitamin B3, in the presence of suitable conjugation reagents, for example, 1-ethyl-3-(3-dimethylaminopropyl)-carbodiimide (EDC) and N-hydroxy succinimide (NHS).

The present disclosure provides composition comprising a carrier unit (e.g., a cationic carrier unit) of the present disclosure. In other aspects, the present disclosure provides complexes comprising a carrier unit (e.g., a cationic carrier unit unit) of the present disclosure non-covalently attached to a payload (e.g., an anionic payload such a nucleotide sequence, e.g., an oligonucleotide, an siRNA, an shRNA, an "antimir", or any combination thereof), wherein the carrier unit and the payload interact electrostatically. In other aspects, the present disclosure provides conjugates comprising a carrier unit (e.g., a cationic carrier unit unit) of the present disclosure covalently attached to a payload (e.g., an anionic payload such a nucleotide sequence, e.g., an oligonucleotide, an siRNA, an shRNA, an "antimir", or any combination thereof), wherein the carrier unit and the payload interact electrostatically. In some aspects, the carrier unit and the payload can be linked via a cleavable linker. In some aspects, the carrier unit and the payload, in addition to interacting electrostatically, can interact covalently (e.g., after electrostatic interaction the carrier unit and the payload can be "locked" via a disulfide bond or a cleavable bond).

In some specific aspects, the cationic carrier unit comprises a water-soluble polymer comprising a PEG with about 120 to about 130 units, a cationic carrier moiety comprising a polylysine with about 30 to about lysine units, and an adjuvant moiety comprising about 5 to about 10 vitamin B3 units.

In some aspects, the cationic carrier unit is associated with a negatively charged payload (e.g., a nucleotide sequence, e.g., an oligonucleotide (e.g., an antisense oligonucleotide), an siRNA, an shRNA, an "antimir", or any combination thereof), which interacts with the cationic carrier unit via at least one ionic bond (i.e., via electrostatic interaction) with the cationic carrier moiety of the cationic carrier unit.

Figure 6:
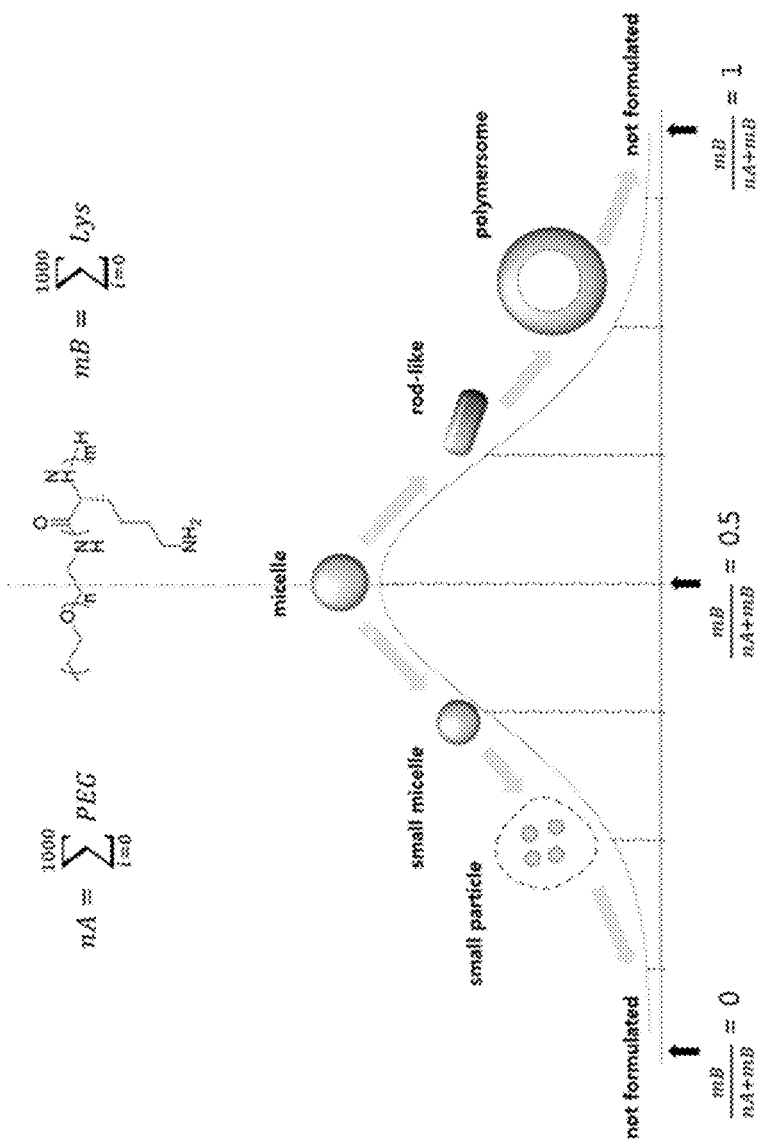
FIG. 6 shows how the shape and size, and therefore loading capacity, of the micelles of the present disclosure can be modified by altering the ratio between water-soluble biopolymer (e.g., PEG) and cationic carrier (e.g., poly lysine). Depending on the ratio, the carrier units can organize as small particles, small micelles, micelles, rod-like structures, or polymersomes. It is to be understood that the term "micelles of the present disclosure" encompasses not only classic micelles but also small particles, small micelles, micelles, rod-like structures, or polymersomes.

In some aspects, the micelle of the present disclosure can be constructed based on the formula shown in FIG. 6. In some aspects, the mB/(nA+mB) of the micelle is higher than 0 and lower than 1, e.g., between about 0.25 and about 1, between about 0.3 and about 1, between about 0.4 and about 1, between about 0.5 and about 1, between about 0.25 and about 0.9, between about 0.3 and about 0.9, between about 0.4 and about 0.9, between about 0.5 and about 0.9, between about 0.25 and about 0.8, between about 0.3 and about 0.8, between about 0.4 and about 0.8, between about 0.5 and about 0.8, between about 0.25 and about 0.75, between about 0.3 and about 0.75, between about 0.4 and about 0.75, between about 0.5 and about 0.75, between about 0.25 and about 0.7, between about 0.3 and about 0.7, between about 0.4 and about 0.7, between about 0.5 and about 0.7, between about 0.25 and about 0.6, between about 0.3 and about 0.6, between about 0.4 and about 0.6, between about 0.5 and about 0.6, between about 0.45 and about 0.55, between about 0.4 and about 0.65, or between about 0.5 and about 0.65,
wherein nA is $$\sum_{i=0}^{1000} PEG$$

and mB is $$\sum_{i=0}^{1000} Lys.$$

In some aspects, the mB/(nA+mB) of the micelle is between about 0.4 and about 0.6, between about 0.5 and about 0.6, or between about 0.4 and about 0.5,
wherein nA is $$\sum_{i=0}^{1000} PEG$$

and mB is $$\sum_{i=0}^{1000} Lys.$$

In some aspects, the mB/(nA+mB) of the micelle is about 0.5,
wherein nA is $$\sum_{i=0}^{1000} PEG$$

and mB is $$\sum_{i=0}^{1000} Lys.$$

The specific components of the cationic carrier units of the present disclosure are disclosed in detail below.

a. Water-Soluble Biopolymer

In some aspects, the cationic carrier units of the present disclosure comprise at least one water-soluble biopolymer. The term "water-soluble biopolymer" as used herein refers to a biocompatible, biologically inert, non-immunogenic, non-toxic, and hydrophilic polymer, e.g., PEG.

In some aspects, the water-soluble polymer comprises poly(alkylene glycols), poly(oxyethylated polyol), poly (olefinic alcohol), poly(vinylpyrrolidone), poly(hydroxyalkylmethacrylamide), poly(hydroxyalkylmethacrylate), poly (saccharides), poly(α-hydroxy acid), poly(vinyl alcohol), polyglycerol, polyphosphazene, polyoxazolines ("POZ") poly(N-acryloylmorpholine), or any combinations thereof. In some aspects, the water-soluble biopolymer is linear, branched, or dendritic.

In some aspects, the water-soluble biopolymer comprises polyethylene glycol ("PEG"), polyglycerol ("PG"), or poly (propylene glycol) ("PPG"). PPG is less toxic than PEG, so many biological products are now produced in PPG instead of PEG.

In some aspects, the water-soluble biopolymer comprises a PEG characterized by a formula $R^3$—(O—$CH_2$—$CH_2$)$_n$— or $R^3$—(O—$CH_2$—$CH_2$)$_n$—O— with $R^3$ being hydrogen, methyl or ethyl and n having a value from 2 to 200. In some aspects, the PEG has the formula (Formula III)

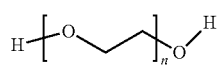

wherein n is 1 to 1000.

In some aspects, the n of the PEG has a value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 189, 181, 182, 183, 184, 185, 186, 187, 188, 189, 190, 191, 192, 193, 194, 195, 196, 197, 198, 199, or 200.

In some aspects, n is at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 310, at least about 320, at least about 330, at least about 340, at least about 350, at least about 360, at least about 370, at least about 380, at least about 390, at least about 400, at least about 410, at least about 420, at least about 430, at least about 440, at least about 450, at least about 460, at least about 470, at least about 480, at least about 490, at least about 500, at least about 510, at least about 520, at least about 530, at least about 540, at least about 550, at least about 560, at least about 670, at least about 580, at least about 590, at least about 600, at least about 610, at least about 620, at least about 630, at least about 640, at least about 650, at least about 660, at least about 670, at least about 680, at least about 690, at least about 700, at least about 710, at least about 720, at least about 730, at least about 740, at least about 750, at least about 760, at least about 770, at least about 780, at least about 790, at least about 800, at least about 810, at least about 820, at least about 830, at least about 840, at least about 850, at least about 860, at least about 870, at least about 880, at least about 890, at least about 900, at least about 910, at least about 920, at least about 930, at least about 940, at least about 950, at least about 960, at least about 970, at least about 980, at least about 990, or about 1000.

In some aspects, n is between about 50 and about 100, between about 100 and about 150, between about 150 and about 200, between about 200 and about 250, between about 250 and about 300, between about 300 and about 350, between about 350 and about 400, between about 400 and about 450, between about 450 and about 500, between about 500 and about 550, between about 550 and about 600, between about 600 and about 650, between about 650 and about 700, between about 700 and about 750, between about 750 and about 800, between about 800 and about 850, between about 850 and about 900, between about 900 and about 950, or between about 950 and about 1000.

In some aspects, n is at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least 110, at least about 111, at least about 112, at least about 113, at least about 114, at least about 115, at least about 116, at least about 117, at least about 118, at least about 119, at least about 120, at least about 121, at least about 122, at least about 123, at least about 124, at least about 125, at least about 126, at least about 127, at least about 128, at least about 129, at least about 130, at least about 131, at least about 132, at least about 133, at least about 134, at least about 135, at least about 136, at least about 137, at least about 138, at least about 139, at least about 140, at least about 141, at least about 142, at least about 143, at least about 144, at least about 145, at least about 146, at least about 147, at least about 148, at least about 149, at least about 150, at least about 151, at least about 152, at least about 153, at least about 154, at least about 155, at least about 156, at least about 157, at least about 158, at least about 159, or at least about 160.

In some aspects, n is about 80 to about 90, about 90 to about 100, about 100 to about 110, about 110 to about 120, about 120 to about 130, about 130 to about 140, about 140 to about 150, about 150 to about 160, about 85 to about 95, about 95 to about 105, about 105 to about 115, about 115 to about 125, about 125 to about 135, about 135 to about 145, about 145 to about 155, about 155 to about 165, about 80 to about 100, about 100 to about 120, about 120 to about 140, about 140 to about 160, about 85 to about 105, about 105 to about 125, about 125 to about 145, or about 145 to about 165.

In some aspects, n is about 100 to about 150. In some aspects, n is about 100 to about 140. In some aspects, n is about 100 to about 130. In some aspects, n is about 110 to about 150. In some aspects, n is about 110 to about 140. In some aspects, n is about 110 to about 130. In some aspects, n is about 110 to about 120. In some aspects, n is about 120 to about 150. In some aspects, n is about 120 to about 140. In some aspects, n is about 120 to about 130. In some aspects, n is about 130 to about 150. In some aspects, n is about 130 to about 140.

Thus, is some aspects, the PEG is a branched PEG. Branched PEGs have three to ten PEG chains emanating from a central core group. In certain aspects, the PEG moiety is a monodisperse polyethylene glycol. In the context of the present disclosure, a monodisperse polyethylene glycol (mdPEG) is a PEG that has a single, defined chain length and molecular weight. mdPEGs are typically generated by separation from the polymerization mixture by chromatography. In certain formulae, a monodisperse PEG moiety is assigned the abbreviation mdPEG.

In some aspects, the PEG is a Star PEG. Star PEGs have 10 to 100 PEG chains emanating from a central core group. In some aspects, the PEG is a Comb PEGs. Comb PEGs have multiple PEG chains normally grafted onto a polymer backbone.

In certain aspects, the PEG has a molar mass between about 1000 g/mol and about 2000 g/mol, between about 2000 g/mol and about 3000 g/mol, between about 3000 g/mol to about 4000 g/mol, between about 4000 g/mol and about 5000 g/mol, between about 5000 g/mol and about 6000 g/mol, between about 6000 g/mol and about 7000 g/mol, or between about 7000 g/mol and about 8000 g/mol.

In some aspects, the PEG is $PEG_{100}$, $PEG_{200}$, $PEG_{300}$, $PEG_{400}$, $PEG_{500}$, $PEG_{600}$, $PEG_{700}$, $PEG_{800}$, $PEG_{900}$, $PEG_{1000}$, $PEG_{1100}$, $PEG_{1200}$, $PEG_{1300}$, $PEG_{1400}$, $PEG_{1500}$, $PEG_{1600}$, $PEG_{1700}$, $PEG_{1800}$, $PEG_{1900}$, $PEG_{2000}$, $PEG_{2100}$, $PEG_{2200}$, $PEG_{2300}$, $PEG_{2400}$, $PEG_{2500}$, $PEG_{1600}$, $PEG_{1700}$, $PEG_{1800}$, $PEG_{1900}$, $PEG_{2000}$, $PEG_{2100}$, $PEG_{2200}$, $PEG_{2300}$, $PEG_{2400}$, $PEG_{2500}$, $PEG_{2600}$, $PEG_{2700}$, $PEG_{2800}$, $PEG_{2900}$, $PEG_{3000}$, $PEG_{3100}$, $PEG_{3200}$, $PEG_{3300}$, $PEG_{3400}$, $PEG_{3500}$, $PEG_{3600}$, $PEG_{3700}$, $PEG_{3800}$, $PEG_{3900}$, $PEG_{4000}$, $PEG_{4100}$, $PEG_{4200}$, $PEG_{4300}$, $PEG_{4400}$, $PEG_{4500}$, $PEG_{4600}$, $PEG_{4700}$, $PEG_{4800}$, $PEG_{4900}$, $PEG_{5000}$, $PEG_{5100}$, $PEG_{5200}$, $PEG_{5300}$, $PEG_{5400}$, $PEG_{5500}$, $PEG_{5600}$, $PEG_{5700}$, $PEG_{5800}$, $PEG_{5900}$, $PEG_{6000}$, $PEG_{6100}$, $PEG_{6200}$, $PEG_{6300}$, $PEG_{6400}$, $PEG_{6500}$, $PEG_{6600}$, $PEG_{6700}$, $PEG_{6800}$, $PEG_{6900}$, $PEG_{7000}$, $PEG_{7100}$, $PEG_{7200}$, $PEG_{7300}$, $PEG_{7400}$, $PEG_{7500}$, $PEG_{7600}$, $PEG_{7700}$, $PEG_{7800}$, $PEG_{7900}$, or $PEG_{8000}$. In some aspects, the PEG is $PEG_{5000}$. In some aspects, the PEG is $PEG_{6000}$. In some aspects, the PEG is $PEG_{4000}$.

In some aspects, the PEG is monodisperse, e.g., $mPEG_{100}$, $mPEG_{200}$, $mPEG_{300}$, $mPEG_{400}$, $mPEG_{500}$, $mPEG_{600}$, $mPEG_{700}$, $mPEG_{800}$, $mPEG_{900}$, $mPEG_{1000}$, $mPEG_{1100}$, $mPEG_{1200}$, $mPEG_{1300}$, $mPEG_{1400}$, $mPEG_{1500}$, $mPEG_{1600}$, $mPEG_{1700}$, $mPEG_{1800}$, $mPEG_{1900}$, $mPEG_{2000}$, $mPEG_{2100}$, $mPEG_{2200}$, $mPEG_{2300}$, $mPEG_{2400}$, $mPEG_{2500}$, $mPEG_{1600}$, $mPEG_{1700}$, $mPEG_{1800}$, $mPEG_{1900}$, $mPEG_{2000}$, $mPEG_{2100}$, $mPEG_{2200}$, $mPEG_{2300}$, $mPEG_{2400}$, $mPEG_{2500}$, $mPEG_{2600}$, $mPEG_{2700}$, $mPEG_{2800}$, $mPEG_{2900}$, $mPEG_{3000}$, $mPEG_{3100}$, $mPEG_{3200}$, $mPEG_{3300}$, $mPEG_{3400}$, $mPEG_{3500}$, $mPEG_{3600}$, $mPEG_{3700}$, $mPEG_{3800}$, $mPEG_{3900}$, $mPEG_{4000}$, $mPEG_{4100}$, $mPEG_{4200}$, $mPEG_{4300}$, $mPEG_{4400}$, $mPEG_{4500}$, $mPEG_{4600}$, $mPEG_{4700}$, $mPEG_{4800}$, $mPEG_{4900}$, $mPEG_{5000}$, $mPEG_{5100}$, $mPEG_{5200}$, $mPEG_{5300}$, $mPEG_{5400}$, $mPEG_{5500}$, $mPEG_{5600}$, $mPEG_{5700}$, $mPEG_{5800}$, $mPEG_{5900}$, $mPEG_{6000}$, $mPEG_{6100}$, $mPEG_{6200}$, $mPEG_{6300}$, $mPEG_{6400}$, $mPEG_{6500}$, $mPEG_{6600}$, $mPEG_{6700}$, $mPEG_{6800}$, $mPEG_{6900}$, $mPEG_{7000}$, $mPEG_{7100}$, $mPEG_{7200}$, $mPEG_{7300}$, $mPEG_{7400}$, $mPEG_{7500}$, $mPEG_{7600}$, $mPEG_{7700}$, $mPEG_{7800}$, $mPEG_{7900}$, or $mPEG_{8000}$. In some aspects, the mPEG is $mPEG_{5000}$. In some aspects, the mPEG is $mPEG_{6000}$. In some aspects, the mPEG is $mPEG_{4000}$.

In some aspects, the water-soluble biopolymer moiety is a polyglycerol (PG) described by the formula $((R_3-O-(CH_2-CHOH-CH_2O)n-)$ with $R_3$ being hydrogen, methyl or ethyl, and n having a value from 3 to 200. In some aspects, the water-soluble biopolymer moiety is a branched polyglycerol described by the formula $(R^3-O-(CH_2-CHOR^5-CH_2-O)_n-)$ with $R^5$ being hydrogen or a linear glycerol chain described by the formula $(R^3-O-(CH_2-CHOH-CH_2-O)_n-)$ and $R^3$ being hydrogen, methyl or ethyl. In some aspects, the water-soluble biopolymer moiety is a hyperbranched polyglycerol described by the formula $(R^3-O-(CH_2-CHOR^5-CH_2-O)_n-)$ with $R^5$ being hydrogen or a glycerol chain described by the formula $(R^3-O-(CH_2-CHOR^6-CH_2-O)_n-)$, with $R^6$ being hydrogen or a glycerol chain described by the formula $(R^3-O-(CH_2-CHOR^7-CH_2-O)_n-)$, with $R^7$ being hydrogen or a linear glycerol chain described by the formula $(R^3-O-(CH_2-CHOH-CH_2-O)_n-)$ and $R^3$ being hydrogen, methyl or ethyl. Hyperbranched glycerol and methods for its synthesis are described in Oudshorn et al. (2006) Biomaterials 27:5471-5479; Wilms et al. (2010 Acc. Chem. Res. 43, 129-41, and references cited therein.

In certain aspects, the PG has a molar mass between about 1000 g/mol and about 2000 g/mol, between about 2000 g/mol and about 3000 g/mol, between about 3000 g/mol to about 4000 g/mol, between about 4000 g/mol and about 5000 g/mol, between about 5000 g/mol and about 6000 g/mol, between about 6000 g/mol and about 7000 g/mol, or between 7000 g/mol and about 8000 g/mol.

In some aspects, the PG is $PG_{100}$, $PG_{200}$, $PG_{300}$, $PG_{400}$, $PG_{500}$, $PG_{600}$, $PG_{700}$, $PG_{800}$, $PG_{900}$, $PG_{1000}$, $PG_{1100}$, $PG_{1200}$, $PG_{1300}$, $PG_{1400}$, $PG_{1500}$, $PG_{1600}$, $PG_{1700}$, $PG_{1800}$, $PG_{1900}$, $PG_{2000}$, $PG_{2100}$, $PG_{2200}$, $PG_{2300}$, $PG_{2400}$, $PG_{2500}$, $PG_{1600}$, $PG_{1700}$, $PG_{1800}$, $PG_{1900}$, $PG_{2000}$, $PG_{2100}$, $PG_{2200}$, $PG_{2300}$, $PG_{2400}$, $PG_{2500}$, $PG_{2600}$, $PG_{2700}$, $PG_{2800}$, $PG_{2900}$, $PG_{3000}$, $PG_{3100}$, $PG_{3200}$, $PG_{3300}$, $PG_{3400}$, $PG_{3500}$, $PG_{3600}$, $PG_{3700}$, $PG_{3800}$, $PG_{3900}$, $PG_{4000}$, $PG_{4100}$, $PG_{4200}$, $PG_{4300}$, $PG_{4400}$, $PG_{4500}$, $PG_{4600}$, $PG_{4700}$, $PG_{4800}$, $PG_{4900}$, $PG_{5000}$, $PG_{5100}$, $PG_{5200}$, $PG_{5300}$, $PG_{5400}$, $PG_{5500}$, $PG_{5600}$, $PG_{5700}$, $PG_{5800}$, $PG_{5900}$, $PG_{6000}$, $PG_{6100}$, $PG_{6200}$, $PG_{6300}$, $PG_{6400}$, $PG_{6500}$, $PG_{6600}$, $PG_{6700}$, $PG_{6800}$, $PG_{6900}$, $PG_{7000}$, $PG_{7100}$, $PG_{7200}$, $PG_{7300}$, $PG_{7400}$, $PG_{7500}$, $PG_{7600}$, $PG_{7700}$, $PG_{7800}$, $PG_{7900}$, or $PG_{8000}$. In some aspects, the PG is $PG_{5000}$. In some aspects, the PG is $PG_{6000}$. In some aspects, the PG is $PG_{4000}$.

In some aspects, the PG is monodisperse, e.g., $mPG_{100}$, $mPG_{200}$, $mPG_{300}$, $mPG_{400}$, $mPG_{500}$, $mPG_{600}$, $mPG_{700}$, $mPG_{800}$, $mPG_{900}$, $mPG_{1000}$, $mPG_{1100}$, $mPG_{1200}$, $mPG_{1300}$, $mPG_{1400}$, $mPG_{1500}$, $mPG_{1600}$, $mPG_{1700}$, $mPG_{1800}$, $mPG_{1900}$, $mPG_{2000}$, $mPG_{2100}$, $mPG_{2200}$, $mPG_{2300}$, $mPG_{2400}$, $mPG_{2500}$, $mPG_{1600}$, $mPG_{1700}$, $mPG_{1800}$, $mPG_{1900}$, $mPG_{2000}$, $mPG_{2100}$, $mPG_{2200}$, $mPG_{2300}$, $mPG_{2400}$, $mPG_{2500}$, $mPG_{2600}$, $mPG_{2700}$, $mPG_{2800}$, $mPG_{2900}$, $mPG_{3000}$, $mPG_{3100}$, $mPG_{3200}$, $mPG_{3300}$, $mPG_{3400}$, $mPG_{3500}$, $mPG_{3600}$, $mPG_{3700}$, $mPG_{3800}$, $mPG_{3900}$, $mPG_{4000}$, $mPG_{4100}$, $mPG_{4200}$, $mPG_{4300}$, $mPG_{4400}$, $mPG_{4500}$, $mPG_{4600}$, $mPG_{4700}$, $mPG_{4800}$, $mPG_{4900}$, $mPG_{5000}$, $mPG_{5100}$, $mPG_{5200}$, $mPG_{5300}$, $mPG_{5400}$, $mPG_{5500}$, $mPG_{5600}$, $mPG_{5700}$, $mPG_{5800}$, $mPG_{5900}$, $mPG_{6000}$, $mPG_{6100}$, $mPG_{6200}$, $mPG_{6300}$, $mPG_{6400}$, $mPG_{6500}$, $mPG_{6600}$, $mPG_{6700}$, $mPG_{6800}$, $mPG_{6900}$, $mPG_{7000}$, $mPG_{7100}$, $mPG_{7200}$, $mPG_{7300}$, $mPG_{7400}$, $mPG_{7500}$, $mPG_{7600}$, $mPG_{7700}$, $mPG_{7800}$, $mPG_{7900}$, or $mPG_{8000}$.

In some aspects, the water-soluble biopolymer comprises poly(propylene glycol) ("PPG"). In some aspects, PPG is characterized by the following formula, with n having a value from 1 to 1000.

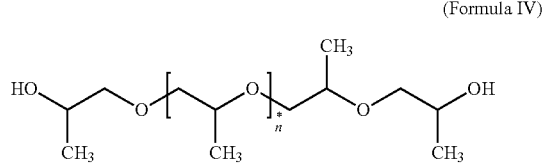

(Formula IV)

In some aspects, the n of the PPG has a value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 189, 181, 182, 183, 184, 185, 186, 187, 188, 189, 190, 191, 192, 193, 194, 195, 196, 197, 198, 199, or 200.

In some aspects, n of the PPG is at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, at least about 200, at least about 210, at least about 220, at least about 230, at least about 240, at least about 250, at least about 260, at least about 270, at least about 280, at least about 290, at least about 300, at least about 310, at least about 320, at least about 330, at least about 340, at least about 350, at least about 360, at least about 370, at least about 380, at least about 390, at least about 400, at least about 410, at least about 420, at least about 430, at least about 440, at least about 450, at least about 460, at least about 470, at least about 480, at least about 490, at least about 500, at least about 510, at least about 520, at least about 530, at least about 540, at least about 550, at least about 560, at least about 670, at least about 580, at least about 590, at least about 600, at least about 610, at least about 620, at least about 630, at least about 640, at least about 650, at least about 660, at least about 670, at least about 680, at least about 690, at least about 700, at least about 710, at least about 720, at least about 730, at least about 740, at least about 750, at least about 760, at least about 770, at least about 780, at least about 790, at least about 800, at least about 810, at least about 820, at least about 830, at least about 840, at least about 850, at least about 860, at least about 870, at least about 880, at least about 890, at least about 900, at least about 910, at least about 920, at least about 930, at least about 940, at least about 950, at least about 960, at least about 970, at least about 980, at least about 990, or about 1000.

In some aspects, the n of the PPG is between about 50 and about 100, between about 100 and about 150, between about 150 and about 200, between about 200 and about 250, between about 250 and about 300, between about 300 and about 350, between about 350 and about 400, between about 400 and about 450, between about 450 and about 500, between about 500 and about 550, between about 550 and about 600, between about 600 and about 650, between about 650 and about 700, between about 700 and about 750, between about 750 and about 800, between about 800 and about 850, between about 850 and about 900, between about 900 and about 950, or between about 950 and about 1000.

In some aspects, the n of the PPG is at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, at least about 125, at least about 126, at least about 127, at least about 128, at least about 129, at least about 130, at least about 131, at least about 132, at least about 133, at least about 134, at least about 135, at least about 136, at least about 137, at least about 138, at least about 139, at least about 140, at least about 141, at least about 142, at least about 143, at least about 144, at least about 145, at least about 146, at least about 147, at least about 148, at least about 149, at least about 150, at least about 151, at least about 152, at least about 153, at least about 154, at least about 155, at least about 156, at least about 157, at least about 158, at least about 159, or at least about 160.

In some aspects, the n of the PPG is about 80 to about 90, about 90 to about 100, about 100 to about 110, about 110 to about 120, about 120 to about 130, about 130 to about 140, about 140 to about 150, about 150 to about 160, about 85 to about 95, about 95 to about 105, about 105 to about 115, about 115 to about 125, about 125 to about 135, about 135 to about 145, about 145 to about 155, about 155 to about 165, about 80 to about 100, about 100 to about 120, about 120 to about 140, about 140 to about 160, about 85 to about 105, about 105 to about 125, about 125 to about 145, or about 145 to about 165.

Thus, is some aspects, the PPG is a branched PPG. Branched PPGs have three to ten PPG chains emanating from a central core group. In certain aspects, the PPG moiety is a monodisperse polyethylene glycol. In the context of the present disclosure, a monodisperse polyethylene glycol (mdPPG) is a PPG that has a single, defined chain length and molecular weight. mdPEGs are typically generated by separation from the polymerization mixture by chromatography. In certain formulae, a monodisperse PPG moiety is assigned the abbreviation mdPPG.

In some aspects, the PPG is a Star PPG. Star PPGs have 10 to 100 PPG chains emanating from a central core group. In some aspects, the PPG is a Comb PPGs. Comb PPGs have multiple PPG chains normally grafted onto a polymer backbone.

In certain aspects, the PPG has a molar mass between about 1000 g/mol and about 2000 g/mol, between about 2000 g/mol and about 3000 g/mol, between about 3000 g/mol to about 4000 g/mol, between about 4000 g/mol and about 5000 g/mol, between about 5000 g/mol and about 6000 g/mol, between about 6000 g/mol and about 7000 g/mol, or between 7000 g/mol and about 8000 g/mol.

In some aspects, the PPG is $PPG_{100}$, $PPG_{200}$, $PPG_{300}$, $PPG_{400}$, $PPG_{500}$, $PPG_{600}$, $PPG_{700}$, $PPG_{800}$, $PPG_{900}$, $PPG_{1000}$, $PPG_{1100}$, $PPG_{1200}$, $PPG_{1300}$, $PPG_{1400}$, $PPG_{1500}$, $PPG_{1600}$, $PPG_{1700}$, $PPG_{1800}$, $PPG_{1900}$, $PPG_{2000}$, $PPG_{2100}$, $PPG_{2200}$, $PPG_{2300}$, $PPG_{2400}$, $PPG_{2500}$, $PPG_{1600}$, $PPG_{1700}$, $PPG_{1800}$, $PPG_{1900}$, $PPG_{2000}$, $PPG_{2100}$, $PPG_{2200}$, $PPG_{2300}$, $PPG_{2400}$, $PPG_{2500}$, $PPG_{2600}$, $PPG_{2700}$, $PPG_{2800}$, $PPG_{2900}$, $PPG_{3000}$, $PPG_{3100}$, $PPG_{3200}$, $PPG_{3300}$, $PPG_{3400}$, $PPG_{3500}$, $PPG_{3600}$, $PPG_{3700}$, $PPG_{3800}$, $PPG_{3900}$, $PPG_{4000}$, $PPG_{4100}$, $PPG_{4200}$, $PPG_{4300}$, $PPG_{4400}$, $PPG_{4500}$, $PPG_{4600}$, $PPG_{4700}$, $PPG_{4800}$, $PPG_{4900}$, $PPG_{5000}$, $PPG_{5100}$, $PPG_{5200}$, $PPG_{5300}$, $PPG_{5400}$, $PPG_{5500}$, $PPG_{5600}$, $PPG_{5700}$, $PPG_{5800}$, $PPG_{5900}$, $PPG_{6000}$, $PPG_{6100}$, $PPG_{6200}$, $PPG_{6300}$, $PPG_{6400}$, $PPG_{6500}$, $PPG_{6600}$, $PPG_{6700}$, $PPG_{6800}$, $PPG_{6900}$, $PPG_{7000}$, $PPG_{7100}$, $PPG_{7200}$, $PPG_{7300}$, $PPG_{7400}$, $PPG_{7500}$, $PPG_{7600}$, $PPG_{7700}$, $PPG_{7800}$, $PPG_{7900}$, or $PPG_{8000}$. In some aspects, the PPG is $PPG_{5000}$. In some aspects, the PPG is $PPG_{6000}$. In some aspects, the PPG is $PPG_{4000}$.

In some aspects, the PPG is monodisperse, e.g., $mPPG_{100}$, $mPPG_{200}$, $mPPG_{300}$, $mPPG_{400}$, $mPPG_{500}$, $mPPG_{600}$, $mPPG_{700}$, $mPPG_{800}$, $mPPG_{900}$, $mPPG_{1000}$, $mPPG_{1100}$, $mPPG_{1200}$, $mPPG_{1300}$, $mPPG_{1400}$, $mPPG_{1500}$, $mPPG_{1600}$, $mPPG_{1700}$, $mPPG_{1800}$, $mPPG_{1900}$, $mPPG_{2000}$, $mPPG_{2100}$, $mPPG_{2200}$, $mPPG_{2300}$, $mPPG_{2400}$, $mPPG_{2500}$, $mPPG_{1600}$, $mPPG_{1700}$, $mPPG_{1800}$, $mPPG_{1900}$, $mPPG_{2000}$, $mPPG_{2100}$, $mPPG_{2200}$, $mPPG_{2300}$, $mPPG_{2400}$, $mPPG_{2500}$, $mPPG_{2600}$, $mPPG_{2700}$, $mPPG_{2800}$, $mPPG_{2900}$, $mPPG_{3000}$, $mPPG_{3100}$, $mPPG_{3200}$, $mPPG_{3300}$, $mPPG_{3400}$, $mPPG_{3500}$, $mPPG_{3600}$, $mPPG_{3700}$, $mPPG_{3800}$, $mPPG_{3900}$, $mPPG_{4000}$, $mPPG_{4100}$, $mPPG_{4200}$, $mPPG_{4300}$, $mPPG_{4400}$, $mPPG_{4500}$, $mPPG_{4600}$, $mPPG_{4700}$, $mPPG_{4800}$, $mPPG_{4900}$, $mPPG_{5000}$, $mPPG_{5100}$, $mPPG_{5200}$, $mPPG_{5300}$, $mPPG_{5400}$, $mPPG_{5500}$, $mPPG_{5600}$, $mPPG_{5700}$, $mPPG_{5800}$, $mPPG_{5900}$, $mPPG_{6000}$, $mPPG_{6100}$, $mPPG_{6200}$, $mPPG_{6300}$, $mPPG_{6400}$, $mPPG_{6500}$, $mPPG_{6600}$, $mPPG_{6700}$, $mPPG_{6800}$, $mPPG_{6900}$, $mPPG_{7000}$, $mPPG_{7100}$, $mPPG_{7200}$, $mPPG_{7300}$, $mPPG_{7400}$, $mPPG_{7500}$, $mPPG_{7600}$, $mPPG_{7700}$, $mPPG_{7800}$, $mPPG_{7900}$, or $mPPG_{8000}$. In some aspects, the mPPG is $mPPG_{5000}$. In some aspects, the mPPG is $mPPG_{6000}$. In some aspects, the mPPG is $mPPG_{4000}$.

b. Cationic carrier

In some aspects, the cationic carrier units of the present disclosure comprise at least one cationic carrier moiety. The term "cationic carrier" refers to a moiety or portion of a cationic carrier unit of the present disclosure comprising a plurality of positive charges that can interact and bind electrostatically an anionic payload (or an anionic carrier attached to a payload). In some aspects, the number of positive charges or positively charged groups on the cationic carrier is similar to the number of negative charges or negatively charged groups on the anionic payload (or an anionic carrier attached to a payload). In some aspects, the cationic carrier comprises a biopolymer, e.g., a peptide (e.g., a polylysine).

In some aspects, the cationic carrier comprises one or more basic amino acids (e.g., lysine, arginine, histidine, or a combination thereof). In some aspects, the cationic carrier comprises at least about three, at least about four, at least about five, at least about six, at least about seven, at least about eight, at least about nine, at least about ten, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80 basic amino acids, e.g., lysines, arginines, or combinations thereof.

In some aspects, the cationic carrier unit comprises at least about 40 basic amino acids, e.g., lysines. In some aspects, the cationic carrier unit comprises at least about 45 basic amino acids, e.g., lysines. In some aspects, the cationic carrier unit comprises at least about 50 basic amino acids, e.g., lysines. In some aspects, the cationic carrier unit comprises at least about 55 basic amino acids, e.g., lysines. In some aspects, the cationic carrier unit comprises at least about 60 basic amino acids, e.g., lysines. In some aspects, the cationic carrier unit comprises at least about 65 basic amino acids, e.g., lysines. In some aspects, the cationic carrier unit comprises at least about 70 basic amino acids, e.g., lysines. In some aspects, the cationic carrier unit comprises at least about 75 basic amino acids, e.g., lysines. In some aspects, the cationic carrier unit comprises at least about 80 basic amino acids, e.g., lysines.

In some aspects, the cationic carrier unit comprises about 30 to about 1000, about 30 to about 900, about 30 to about 800, about 30 to about 700, about 30 to about 600, about 30 to about 500, about 30 to about 400, about 30 to about 300, about 30 to about 200, about 30 to about 100, about 40 to about 1000, about 40 to about 900, about 40 to about 800, about 40 to about 700, about 40 to about 600, about 40 to about 500, about 40 to about 400, about 40 to about 300, about 40 to about 200, or about 40 to about 100 basic amino acids, e.g., lysines.

In some aspects, the cationic carrier unit comprises about 30 to about 100, about 30 to about 90, about 30 to about 80, about 30 to about 70, about 30 to about 60, about 30 to about 50, about 30 to about 40, about 40 to about 100, about 40 to about 90, about 40 to about 80, about 40 to about 70, about 40 to about 60, about 70 to about 80, about 75 to about 85, about 65 to about 75, about 65 to about 80, about 60 to about 85, or about 40 to about 500 basic amino acids, e.g., lysines.

In some aspects, the cationic carrier unit comprises about 100 to about 1000, about 100 to about 900, about 100 to about 800, about 100 to about 700, about 100 to about 600, about 100 to about 500, about 100 to about 400, about 100 to about 300, about 100 to about 200, about 200 to about 1000, about 200 to about 900, about 200 to about 800, about 200 to about 700, about 200 to about 600, about 200 to about 500, about 200 to about 400, about 200 to about 300, about 300 to about 1000, about 300 to about 900, about 300 to about 800, about 300 to about 700, about 300 to about 600, about 300 to about 500, about 300 to about 400, about 400 to about 1000, about 400 to about 900, about 400 to about 800, about 400 to about 700, about 400 to about 600, about 400 to about 500, about 500 to about 1000, about 500 to about 900, about 500 to about 800, about 500 to about 700, about 500 to about 600, about 600 to about 1000, about 600 to about 900, about 600 to about 800, about 600 to about 700, about 700 to about 1000, about 700 to about 900, about 700 to about 800, about 800 to about 1000, about 800 to about 900, or about 900 to about 1000 basic amino acids, e.g., lysines.

In some aspects, the number of basic amino acids, e.g., lysines, arginines, histidines, or combinations thereof, can be adjusted based on the length of the anionic payload. For example, an anionic payload with a longer sequence can be paired with higher number of basic amino acids, e.g., lysines. In some aspects, the number of basic amino acids, e.g., lysines, in the cationic carrier unit can be calculated so that the molar ratio of protonated amine in polymer to phosphate in an anionic payload, e.g., oligonucleotide, e.g., antimir (N/P) is about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3. In some aspects, the number of basic amino acids, e.g., lysines, in the cationic carrier unit is calculated so that the molar ratio of protonated amine in polymer to phosphate in an anionic payload, e.g., oligonucleotide, e.g., antimir (N/P) is about 1.3 to about 1.7, e.g., about 1.5. In some aspects, the number of basic amino acids, e.g., lysines, in the cationic carrier unit is calculated so that the molar ratio of protonated amine in polymer to phosphate in an anionic payload, e.g., oligonucleotide, e.g., antimir (N/P) is about 1.4. In some aspects, the number of basic amino acids, e.g., lysines, in the cationic carrier unit is calculated so that the molar ratio of protonated amine in polymer to phosphate in an anionic payload, e.g., oligonucleotide, e.g., antimir (N/P) is about 1.6. In some aspects, the number of basic amino acids, e.g., lysines, in the cationic carrier unit is calculated so that the molar ratio of protonated amine in polymer to phosphate in an anionic payload, e.g., oligonucleotide, e.g., antimir (N/P) is about 1.3. In some aspects, the number of basic amino acids, e.g., lysines, in the cationic carrier unit is calculated so that the molar ratio of protonated amine in polymer to phosphate in an anionic payload, e.g., oligonucleotide, e.g., antimir (N/P) is about 1.7.

A person of skill in the art would understand that since a role of the cationic carrier moiety is to neutralize negative charges on the payload (e.g., negative changes in the phosphate backbone of an antisense oligonucleotide) via electrostatic interaction, in some aspects (e.g., when the payload is a nucleic acid such as an antimir), the length of the cationic carrier, number of positively charged groups on the cationic carrier, and distribution and orientation of charges present on the cationic carrier will depend on the length and charge distribution on the payload molecule.

In other aspects, e.g., when the payload are multiple small molecules (e.g., anionic small molecule drugs), the length of the cationic carrier and number of positively charged groups on the cationic carrier correlate with the desired payload. For example, the number of small molecule drugs carried by the cationic carrier unit of the present disclosure would depend on the number of charges in the cationic carrier moiety.

In some aspects, the cationic carrier comprises between about 5 and about 10, between about 10 and about 15, between about 15 and about 20, between about 20 and about 25, between about 25 and about 30, between about 30 and about 35, between about 35 and about 40, between about 40 and about 45, between about 45 and about 50, between about 50 and about 55, between about 55 and about 60, between about 60 and about 65, between about and about 70, between about 70 and about 75, or between about 75 and about 80 basic amino acids. In some specific aspects, the positively charged carrier comprises between 30 and about 50 basic amino acids. In some specific aspects, the positively charged carrier comprises between 70 and about 80 basic amino acids.

In some aspects, the basic amino acid comprises arginine, lysine, histidine, or any combination thereof. In some aspects, the basic amino acid is a D-amino acid. In some aspects, the basic amino acid is an L-amino acid. In some aspects, the positively charged carrier comprises D-amino acids and L-amino acids. In some aspects, the basic amino comprises at least one unnatural amino acid or a derivative thereof. In some aspects, the basic amino acid is arginine, lysine, histidine, L-4-aminomethyl-phenylalanine, L-4-guanidine-phenylalanine, L-4-aminomethyl-N-isopropyl-phenylalanine, L-3-pyridyl-alanine, L-trans-4-aminomethylcyclohexyl-alanine, L-4-piperidinyl-alanine, L-4-aminocyclohexyl-alanine, 4-guanidinobutyric acid, L-2-amino-3-guanidinopropionic acid, DL-5-hydroxylysine, pyrrolysine, 5-hydroxy-L-lysine, methyllysine, hypusine, or any combination thereof. In a particular aspect, the positively charged carrier comprises about 40 lysines. In a particular aspect, the positively charged carrier comprises about 50 lysines. In a particular aspect, the positively charged carrier comprises about 60 lysines. In a particular aspect, the positively charged carrier comprises about 70 lysines. In a particular aspect, the positively charged carrier comprises about 80 lysines.

In other aspects, the cationic carrier comprises an alkyl chain, e.g., $C_3$ to $C_{50}$, comprising at least three, at least four, at least five, at least six, at least seven, at least eight, at least nine, at least ten, at least 11, at least 12, at least 13, at least 14, at last 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 67, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, or at least 80 cationic groups (e.g., amino groups). In some aspects, the cationic carrier comprises an alkyl chain, e.g., $C_3$ to $C_{50}$, comprising between about 5 and about 10, between about 10 and about 15, between about 15 and about 20, between about 20 and about 25, between about 25 and about 30, between about 30 and about 35, between about 35 and about 40, between about 40 and about 45, between about 45 and about 50, between about 50 and about 55, between about 55 and about 60, between about 60 and about 65, between about 65 and about 70, between about 70 and about 75, or between about 75 and about 80 cationic groups (e.g., amino groups). In some specific aspects, the cationic carrier comprises an alkyl chain, e.g., $C_3$ to $C_{50}$, comprising between 30 and about 50 cationic groups (e.g., amino groups). In some specific aspects, the cationic carrier comprises an alkyl chain, e.g., $C_3$ to $C_{50}$, comprising between 70 and about 80 cationic groups (e.g., amino groups).

In other aspects, the cationic carrier comprises a polymer or copolymer comprising at least three, at least four, at least five, at least six, at least seven, at least eight, at least nine, at least ten, at least 11, at least 12, at least 13, at least 14, at last 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, or at least 80 cationic groups (e.g., amino groups). In some aspects, the cationic carrier comprises a polymer or copolymer comprising between about 5 and about 10 cationic groups, between about 10 and about 15 cationic groups, between about 15 and about 20 cationic groups, between about 20 and about 25 cationic groups, between about 25 and about 30 cationic groups, between about 30 and about 35 cationic groups, between about 35 and about 40 cationic groups, between about 40 and about 45 cationic groups, between about 45 and about 50 cationic groups, between about 50 and about 55 cationic groups, between about 55 and about 60 cationic groups, between about 60 and about 65 cationic groups, between about 65 and about 70 cationic groups, between about 70 and about 75 cationic groups, or between about 45 and about 50 cationic groups (e.g., amino groups). In some specific aspects, the cationic carrier comprises a polymer or copolymer comprising between 30 and about 50 cationic groups (e.g., amino groups). In some specific aspects, the cationic carrier comprises a polymer or copolymer comprising between 70 and about 80 cationic groups (e.g., amino groups). In some aspects, the polymer or copolymer is an acrylate, a polyalcohol, or a polysaccharide.

In some aspects, the cationic carrier moiety binds to a single payload molecule. In other aspects, a cationic carrier moiety can bind to multiple payload molecules, which may be identical or different.

In some aspects, the positive charges of the cationic carrier moiety and negative charges of a nucleic acid payload are at an ionic ratio of about 3:1, about 2.9:1, about 2.8:1, about 2.7:1, about 2.6:1, about 2.5:1, about 2.4:1, about 2.3:1, about 2.2:1, about 2:1, about 2:1, about 1.9:1, about 1.8:1, about 1.7:1, about 1.6:1, about 1.5:1, about 1.4:1, about 1.3:1, about 1.2:1, about 1.1:1, about 1:1, about 1:1.1, about 1:1.2, about 1:1.3, about 1:1.4, about 1:1.5, about 1:1.6, about 1:1.7, about 1:1.8, about 1:1.9, about 1:2, about 1:2.1, about 1:2.2, about 1:2.3, about 1:2.4, about 1:2.5, about 1:2.6, about 1:2.7, about 1:2.8, about 1:2.9, or about 1:3. In some aspects, the positive charges of the cationic carrier moiety and the negative charged of the nucleic acid payload are at a charge ratio of 1:1. In some aspects, the positive charges of the cationic carrier moiety and the negative charges of the nucleic acid payload are at a charge ratio of 3:2. In some aspects, the positive charges of the cationic carrier moiety and the negative charges of the nucleic acid payload are at a charge ratio of 2:3.

In some aspects, the carrier units of the present disclosure comprise:

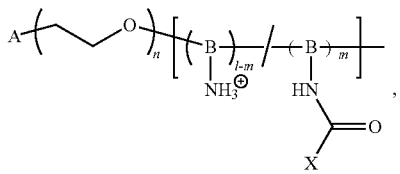

wherein A is tryptophan or phenylalanine, and B is a cationic carrier moiety, e.g., lysine,
wherein,
  (i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;
  (ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and,
  (iii) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;
and wherein X is

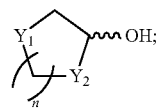

wherein $Y_1$ is C, N, O, or S, and $Y_2$ is C, N O, or S, and n is 1 or 2. In some aspects, X can be —SH (e.g., sulfanyl group, alkanethiols or alkyl thiols). In some aspects, the micelle of the present disclosure comprises one type of cationic carrier units conjugated to a vitamin, e.g., vitamin B3, and another type of cationic carrier units conjugated to a sulfanyl group (e.g., alkanethiols or alkyl thiols). In some aspects, the micelle of the present disclosure comprises a first type of cationic carrier units conjugated to a vitamin, e.g., vitamin B3, a second type of cationic carrier units conjugated to a sulfanyl group (e.g., alkanethiols or alkyl thiols); and a third type of cationic carrier units that are a free base.

In some aspects, the carrier units of the present disclosure comprise:

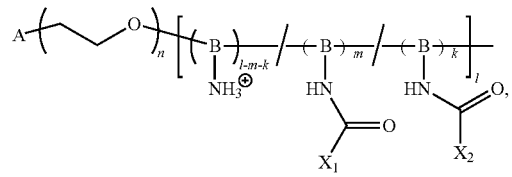

wherein A is tryptophan or phenylalanine, and B is a cationic carrier moiety, e.g., lysine,
wherein,
  (i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;
  (ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150;
  (iii) k is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and, (iii) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

wherein $X_1$ is

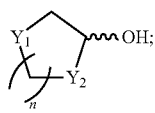

wherein $Y_1$ is C, N, O, or S, and $Y_2$ is C, N O, or S, and n is 1 or 2; and wherein $X_2$ is

wherein p=0 to 5. In some aspects, p is 0. In some aspects, $X_2$ is SH.

In some aspects, the cationic carrier moiety has a free terminus wherein the end group is a reactive group. In some aspects, the cationic carrier moiety has a free terminus (e.g., the C-terminus in a poly-lysine cationic carrier moiety) wherein the end group is an amino (—NH$_2$) group. In some aspects, the cationic carrier moiety has a free terminus wherein the end group is an sulfhydryl group. In some aspects, the reactive group of the cationic carrier moiety is attached to an adjuvant moiety, e.g., a vitamin B3 adjuvant moiety.

c. Adjuvant Moiety

In some aspects, the cationic carrier units of the present disclosure comprise at least one adjuvant moiety. The term "adjuvant moiety", as used herein, refers to a molecular entity that can, e.g., (i) complement the therapeutic or prophylactic activity of the payload, (ii) modulate the therapeutic or prophylactic activity of the payload, (iii) function as a therapeutic and/or prophylactic agent in the target tissue or target cells, (iv) facilitate the transport of the cationic carrier unit across a physiological barrier, e.g., the BBB and/or the plasma membrane, (v) improve the homeostasis of the target tissue or target cell, (vi) contribute positively charges groups to the cationic carried moiety, or (vii) any combination thereof.

In some aspects, the adjuvant moiety is capable of modulating, e.g., an immune response, an inflammatory response, or a tissue microenvironment.

In some aspects, an adjuvant moiety capable of modulating an immune response can comprise, e.g., tyrosine or dopamine. Tyrosine can be transformed into L-DOPA, and then be converted to dopamine via 2-step enzymatic reaction. Normally, dopamine levels are low in the Parkinson's disease patients. Therefore, in some aspects, tyrosine is an adjuvant moiety in cationic carrier units used for the treatment of Parkinson's disease. Tryptophan can be converted to serotonin, a neurotransmitter thought to play a role in appetite, emotions, and motor, cognitive, and autonomic functions. Accordingly, in some aspects, cationic carrier units of the present disclosure used for the treatment of disease or conditions related to low serotonin levels comprise tryptophan as an adjuvant moiety.

In some aspects, an adjuvant moiety can modulate a tumor microenvironment in a subject with a tumor, for example, by inhibiting or reducing hypoxia in the tumor microenvironment.

In some aspects, the adjuvant moiety comprises, e.g., an imidazole derivative, an amino acid, a vitamin, or any combination thereof.

In some aspects, the adjuvant moiety is an imidazole derivative comprising:

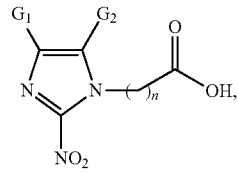

(Formula VI)

wherein each of $G_1$ and $G_2$ is independently H, an aromatic ring, or 1-10 alkyl, or $G_1$ and $G_2$ together form an aromatic ring, and wherein n is 1-10.

In some aspects, the adjuvant moiety comprises nitroimidazole. Nitroimidazoles function as antibiotics. Nitroheterocycles in nitroimidazoles can be reductively activated in hypoxic cells, and then undergo redox recycling or decompose to cytotoxic products. Reduction usually happens only in anaerobic bacteria or in anoxic tissues, therefore, they have relative little effect upon human cells or aerobic bacteria. In some aspects, the adjuvant moiety comprises metronidazole, tinidazole, nimorazole, dimetridazole, pretomanid, ornidazole, megazol, azanidazole, benznidazole, nitroimidazole, or any combination thereof.

In some aspects, the adjuvant moiety comprises an amino acid. In some aspects, the adjuvant moiety comprises

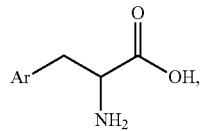

(Formula VII)

wherein Ar is

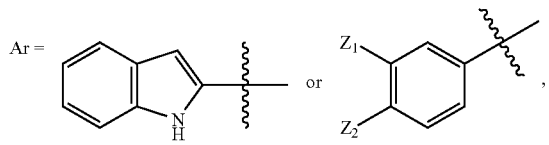

and wherein each of Z1 and Z2 is H or OH.

In some aspects, the adjuvant moiety is capable of inhibiting or reducing an inflammatory response.

In some aspects, the adjuvant moiety is a vitamin. In some aspects, the vitamin comprises a cyclic ring or cyclic hetero atom ring and a carboxyl group or hydroxyl group. In some aspects, the vitamin comprises:

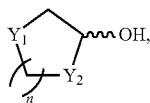 (Formula VIII)

wherein each of Y1 and Y2 is C, N, O, or S, and wherein n is 1 or 2.

In some aspects, the vitamin is selected from the group consisting of vitamin A (retinol), vitamin B1 (Thiamine Chloride), vitamin B2 (Riboflavin), vitamin B3 (Niacinamide), vitamin B6 (Pyridoxal), vitamin B7 (Biotin), vitamin B9 (Folic acid), vitamin B12 (Cobalamin), vitamin C (Ascorbic acid), vitamin D2, vitamin D3, vitamin E (Tocopherol), vitamin M, vitamin H, a derivative thereof, and any combination thereof.

In some aspects, the vitamin is vitamin B3 (also known as niacin or nicotinic acid).

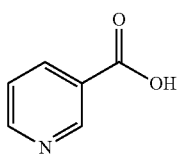 (Formula IX)

In some aspects, the adjuvant moiety comprises at least about two, at least about three, at least about four, at least about five, at least about six, at least about seven, at least about eight, at least about nine, at least about ten, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, or at least about 30 vitamin B3. In some aspects, the adjuvant moiety comprises about 10 vitamin B3. In some aspects, the adjuvant moiety comprises about 7 vitamin B3. In some aspects, the adjuvant moiety comprises about 8 vitamin B3. In some aspects, the adjuvant moiety comprises about 9 vitamin B3. In some aspects, the adjuvant moiety comprises about 10 vitamin B3. In some aspects, the adjuvant moiety comprises about 11 vitamin B3. In some aspects, the adjuvant moiety comprises about 12 vitamin B3. In some aspects, the adjuvant moiety comprises about 13 vitamin B3. In some aspects, the adjuvant moiety comprises about 14 vitamin B3. In some aspects, the adjuvant moiety comprises about 15 vitamin B3. In some aspects, the adjuvant moiety comprises about 20 vitamin B3. In some aspects, the adjuvant moiety comprises about 25 vitamin B3. In some aspects, the adjuvant moiety comprises about 30 vitamin B3.

In some aspects the adjuvant moiety comprises from about 5 to about 10 vitamin B3, about 10 to about 15 vitamin B3, about 15 to about 20 vitamin B3, about 20 to about 25 vitamin B3, about 25 to about 30 vitamin B3, about 30 to about 35 vitamin B3, about 35 to about 40 vitamin B3, about 40 to about 45 vitamin B3, about 45 to about 50 vitamin B3. In some aspects the adjuvant moiety comprises from about 10 to about 20 vitamin B3, about 20 to about 30 vitamin B3, about 30 to about 40 vitamin B3, about 40 to about 50 vitamin B3, about 5 to about 15 vitamin B3, about 15 to about 25 vitamin B3, about 25 to about 35 vitamin B3, about 35 to about 45 vitamin B3, about 45 to about 55 vitamin B3.

Niacin is a precursor of the coenzymes nicotinamide adenine dinucleotide (NAD) and nicotinamide adenine dinucleotide phosphate (NADP) in vivo. NAD converts to NADP by phosphorylation in the presence of the enzyme NAD+kinase. NADP and NAD are coenzymes for many dehydrogenases, participating in many hydrogen transfer processes. NAD is important in catabolism of fat, carbohydrate, protein, and alcohol, as well as cell signaling and DNA repair, and NADP mostly in anabolism reactions such as fatty acid and cholesterol synthesis. High energy requirements (brain) or high turnover rate (gut, skin) organs are usually the most susceptible to their deficiency.

Niacin produces marked anti-inflammatory effects in a variety of tissues—including the brain, gastrointestinal tract, skin, and vascular tissue—through the activation of NIACR1. Niacin has been shown to attenuate neuroinflammation and may have efficacy in treating neuroimmune disorders such as multiple sclerosis and Parkinson's disease. See Offermanns & Schwaninger (2015) Trends in Molecular Medicine 21:245-266; Chai et al (2013) Current Atherosclerosis Reports 15:325; Graff et al. (2016) Metabolism 65:102-13; and Wakade & Chong (2014) Journal of the Neurological Sciences 347:34-8, which are herein incorporated by reference in their entireties.

In some aspects, the carrier units of the present disclosure comprise:

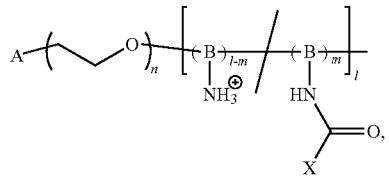

wherein X is vitamin B3;
A is a targeting moiety, and
B is a cationic carrier moiety, e.g., lysine, and
wherein,
(i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;
(ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and,
(iii) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200.

In some aspects, the carrier units of the present disclosure comprise:

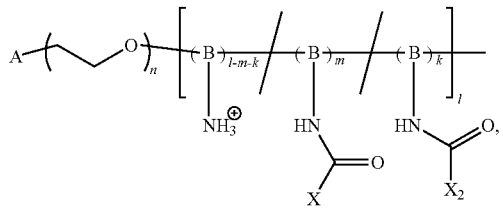

wherein X is vitamin B3;

A is a targeting moiety, and

B is a cationic carrier moiety, e.g., lysine, and wherein, (i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

(ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150;

(iii) k is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and, (iii) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

wherein $X_1$ is

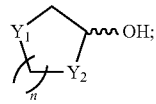

wherein $Y_1$ is C, N, O, or S, and $Y_2$ is C, N O, or S, and n is 1 or 2; and wherein $X_2$ is

wherein p=0 to 5. In some aspects, p is 0. In some aspects, $X_2$ is SH.

d. Targeting Moiety

In some aspects, the cationic carrier unit comprises a targeting moiety, which is linked to the water-soluble polymer optionally via a linker. As used herein, the term "targeting moiety" refers to a biorecognition molecule that binds to a specific biological substance or site. In some aspects, the targeting moiety is specific for a certain target molecule (e.g., a ligand targeting a receptor, or an antibody targeting a surface protein), tissue (e.g., a molecule that would preferentially carry the micelle to a specific organ or tissue, e.g., liver, brain, or endothelium), or facilitate transport through a physiological barrier (e.g., a peptide or other molecule that may facilitate transport across the brain blood barrier or plasma membrane).

For targeting a payload (e.g., a nucleotide molecule, e.g., an antisense oligonucleotide that binds to a microRNA) according to the present disclosure, a targeting moiety can be coupled to a cationic carrier unit, and therefore, to the external surface of a micelle, whereas the micelle has the payload entrapped within its core.

In some aspects, the targeting moiety is a targeting moiety capable of targeting the micelle of the present disclosure to a tissue. In some aspects, the tissue is liver, brain, kidney, lung, ovary, pancreas, thyroid, breast, stomach, or any combination thereof. In some aspects, the tissue is cancer tissue, e.g., liver cancer, brain cancer, kidney cancer, lung cancer, ovary cancer, pancreas cancer, thyroid cancer, breast cancer, stomach cancer, or any combination thereof.

In a specific aspect, the tissue is liver. In a specific aspect, the targeting moiety targeting liver is cholesterol. In other aspects, the targeting moiety targeting liver is a ligand that binds an asialoglycoprotein receptor targeting moiety. In some aspects, the asialoglycoprotein receptor targeting moiety comprises a GalNAc cluster. In some aspects, the GalNAc cluster is a monovalent, divalent, trivalent, or tetravalent GalNAc cluster.

In another aspect, the tissue is pancreas. In some aspects, the targeting moiety targeting pancreas comprises a ligand targeting αvβ3 integrin receptors on pancreatic cells. In some aspects, the targeting moiety comprises an arginylglycylaspartic acid (RGD) peptide sequence (L-Arginyl-Glycyl-L-Aspartic acid; Arg-Gly-Asp).

In some aspects, the tissue is a tissue in the central nervous system, e.g., neural tissue. In some aspects, the targeting moiety targeting the central nervous system is capable being transported by Large-neutral Amino Acid Transporter 1 (LAT1). LAT1 (SLC7A5) is a transporter for both the uptake of large neutral amino acids and a number of pharmaceutical drugs. LAT1 can transport drugs such as L-dopa or gabapentin.

In some aspects, a targeting moiety comprises glucose, e.g., D-glucose, which can bind to Glucose transporter 1 (or GLUT1) and cross BBB. GLUT1, also known as solute carrier family 2, facilitated glucose transporter member 1 (SLC2A1), is a uniporter protein that in humans is encoded by the SLC2A1 gene. GLUT1 facilitates the transport of glucose across the plasma membranes of mammalian cells. This gene encodes a major glucose transporter in the mammalian blood-brain barrier.

In some aspects, a targeting moiety comprises galactose, e.g., D-galactose, which can bind to GLUT1 transporter to cross BBB. In some aspects, a targeting moiety comprises glutamic acid, which can bind to acetylcholinesterase inhibitor (AChEI) and/or EAATs inhibitors and cross BBB. Acetylcholinesterase is the enzyme that is the primary member of the cholinesterase enzyme family. An acetylcholinesterase inhibitor (AChEI) is the inhibitor that inhibits acetylcholinesterase from breaking down acetylcholine into choline and acetate, thereby increasing both the level and duration of action of the neurotransmitter acetylcholine in the central nervous system, autonomic ganglia and neuromuscular junctions, which are rich in acetylcholine receptors. Acetylcholinesterase inhibitors are one of two types of cholinesterase inhibitors; the other being butyryl-cholinesterase inhibitors.

In some aspects, a targeting moiety is GABA, which can bind to GABA receptors to cross BBB. The GABA receptors are a class of receptors that respond to the neurotransmitter gamma-aminobutyric acid (GABA), the chief inhibitory compound in the mature vertebrate central nervous system. There are two classes of GABA receptors: GABAA and GABAB. GABAA receptors are ligand-gated ion channels (also known as ionotropic receptors); whereas GABAB receptors are G protein-coupled receptors, also called metabotropic receptors.

In some aspects, a targeting moiety comprises tyrosine, which can bind to LAT1 and cross BBB. In some aspects, a targeting moiety comprises lysine, which can bind to LAT1 and cross BBB. In some aspects, a targeting moiety comprises glutamine, which can bind to LAT1 and cross BBB. In some aspects, a targeting moiety comprises phenylalanine, which can bind to GABA receptors, LAT1, CNS reverse transcriptase inhibitors, and/or dopamine (DA) receptors and cross BBB. Dopamine receptors are a class of G protein-coupled receptors that are prominent in the vertebrate central nervous system (CNS). Dopamine receptors activate different effectors through not only G-protein coupling, but also signaling through different protein (dopamine receptor-interacting proteins) interactions. The neurotransmitter dopamine is the primary endogenous ligand for dopamine receptors.

Dopamine receptors are implicated in many neurological processes, including motivation, pleasure, cognition, memory, learning, and fine motor control, as well as modulation of neuroendocrine signaling. Abnormal dopamine receptor signaling and dopaminergic nerve function is implicated in several neuropsychiatric disorders. Thus, dopamine receptors are common neurologic drug targets; antipsychotics are often dopamine receptor antagonists while psychostimulants are typically indirect agonists of dopamine receptors.

In some aspects, a targeting moiety comprises valine, which can bind to CNS reverse transcriptase inhibitors and cross BBB. In some aspects, a targeting moiety comprises tryptophan, which can bind to GABA receptors and/or CNS reverse transcriptase inhibitors and cross BBB. In some aspects, a targeting moiety comprises leucine, which can bind to GABA receptors and/or CNS reverse transcriptase inhibitors and cross BBB. In some aspects, a targeting moiety comprises methionine, which can bind to GABA receptors and/or CNS reverse transcriptase inhibitors and cross BBB. In some aspects, a targeting moiety comprises histidine, which can bind to GABA receptors and cross BBB. In some aspects, a targeting moiety comprises isoleucine, which can bind to CNS reverse transcriptase inhibitors and cross BBB. In some aspects, a targeting moiety comprises Glutathione, which can bind to GSH transporter and cross BBB. In some aspects, a targeting moiety comprises Glutathione-Met, which can bind to GSH transporter and cross BBB. In some aspects, a targeting moiety comprises Urea/Thiourea, which can bind to Nitric oxide synthase (NOS) and bind to BBB. In some aspects, a targeting moiety comprises NAD+/NADH, which is capable of crossing BBB by REDOX mechanism. In some aspects, a targeting moiety comprises purine and can cross BBB. Additional examples of targeting moieties for CNS targeting are shown in Sutera et al. (2016): Small endogenous molecules as moiety to improve targeting of CNS drugs, Expert Opinion on Drug Delivery, DOI: 10.1080/17425247.2016.1208651, which is incorporated herein by reference in its entirety.

In some aspects, the tissue targeted by a targeting moiety is a skeletal muscle. In some aspects, the targeting moiety targeting skeletal muscle is capable being transported by Large-neutral Amino Acid Transporter 1 (LAT1).

It is expressed in numerous cell types including T-cells, cancer cells and brain endothelial cells. LAT1 is consistently expressed at high levels in brain microvessel endothelial cells. Being a solute carrier located primarily in the BBB, targeting the micelles of the present disclosure to LAT1 allows delivery through the BBB. In some aspects, the targeting moiety targeting a micelle of the present disclosure to the LAT1 transporter is an amino acid, e.g., a branched-chain or aromatic amino acid. In some aspects, the amino acid is valine, leucine, and/or isoleucine. In some aspects, the amino acid is tryptophan and/or tyrosine. In some aspects, the amino acid is tryptophan. In other aspects, the amino acid is tyrosine.

In some aspects, the targeting moiety is a LAT1 ligand selected from tryptophan, tyrosine, phenylalanine, tryptophan, methionine, thyroxine, melphalan, L-DOPA, gabapentin, 3,5-I-diiodotyrosine, 3-iodo-I-tyrosine, fenclonine, acivicin, leucine, BCH, methionine, histidine, valine, or any combination thereof.

In some aspects, the LAT1 ligand is [1] 1-Phenylalanine, [2] o-Sarcolysin, [3] m-Sarcolysin. [4] Melphalan. [5] 2-Amino-2-norbornanecarboxylic acid (BCH). [6] (±)-2-Amino-1,2,3,4-tetrahydro-2-naphthoic acid, [7] dl-2-NAM-5, [8] dl-2-NAM-6, [9] dl-2-NAM-7, [10] dl-2-NAM-8, [11] dl-dechlorinated-NAM, [12] dl-1-NAM-7, [13] (±)-2-Aminoindane-2 carboxylic acid, [14] (±)-2-Aminobenzo-bicyclo-[2.2.1]heptane-2'-exo-carboxylic acid, [15] (±)-2-amino-(bis-2-chloroethyl)-5-aminoindane-2-carboxylic acid, [16] (±)-2-endo-amino-bis(2-chloroethyl)-7'-amino-benzobicyclo[2.2.1]heptane-2-exo-carboxylic acid, [17] 1-6-diazo-5-oxo-norleucine (l-DON), [18] Acivicin, [19] Azaserine, [20] Buthionine Sulfoximine (BSO), [21] 1-1-naphthylalanine, [22] o-benzyl-l-tyrosine, [23] 1-2-amino-nonanoic acid, [24] l-Tyrosine, [25] α-methyltyrosine, [26] l-DOPA, [27] α-methyldopa, [28] 3-o-methyldopa, [29] Droxidopa, [30] Carbidopa, [31] Dopamine, [32] Tyramine, [33] α-methylphenylalanine, [34] N-methylphenylalanine, [35] Phenylalanine methyl ester, [36] Gabapentin, [37] 3,3'-diiodothyronine, [38] 1-T3, [39] 3',5',3-triiodothyronine (r 1-T3), or [40], 1-T4, or any combination thereof, as shown below.

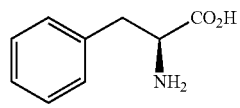
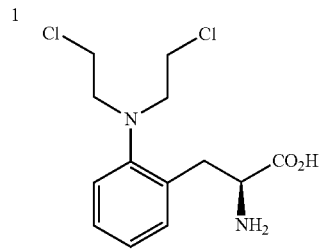
1
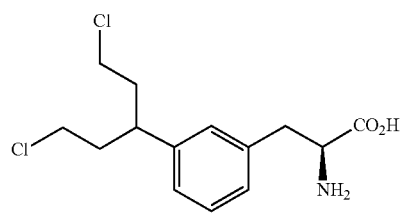
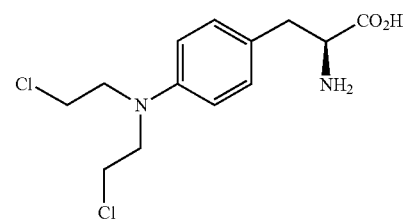
3 4
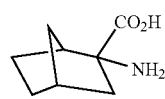
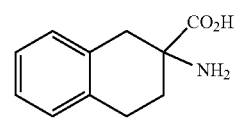
5 6
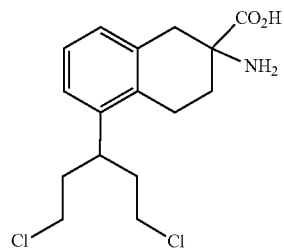
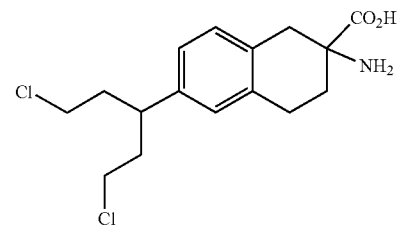
7 8
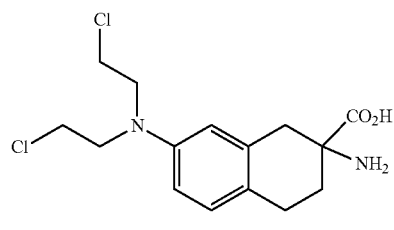
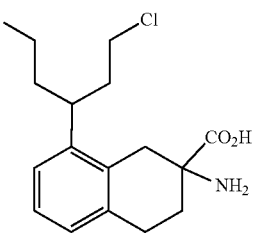
9 10
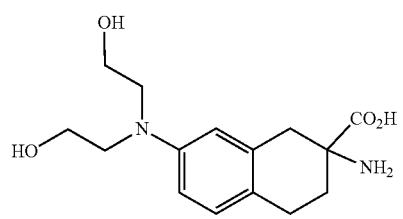
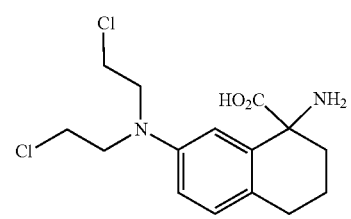
11 12
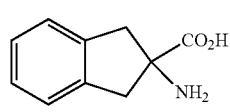
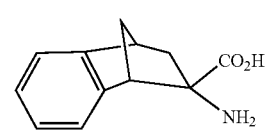
13 14

-continued
| | | |
|---|---|---|
| 15 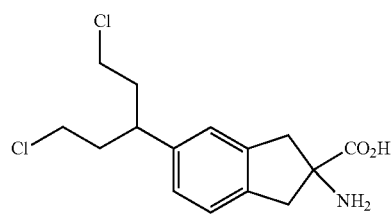 | | 16 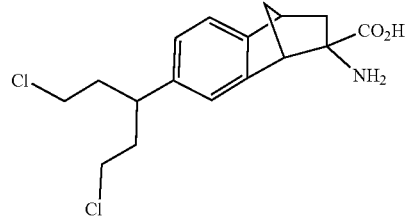 |
| 17 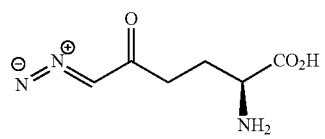 | | 18 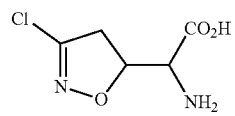 |
| 19 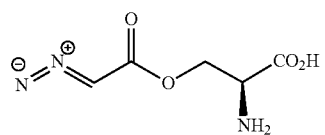 | | 20 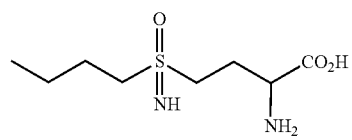 |
| 21 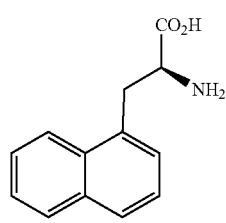 | | 22 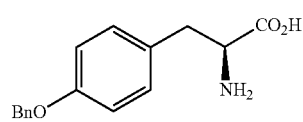 |
| 23 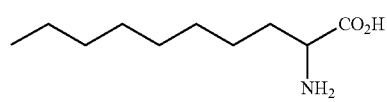 | | 24 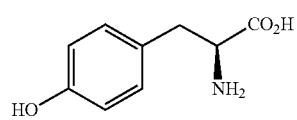 |
| 25 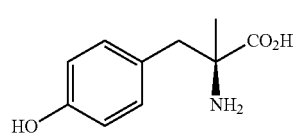 | | 26 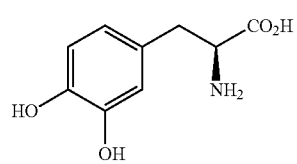 |
| 27 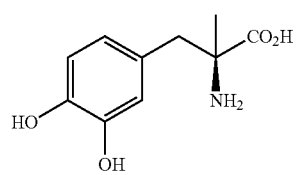 | | 28 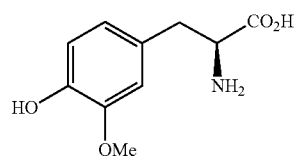 |
| 29 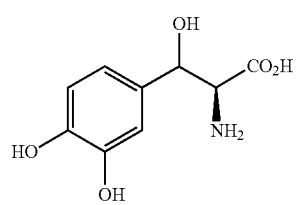 | | 30 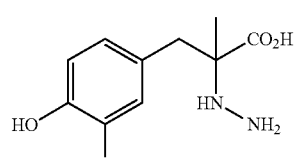 |
| 31 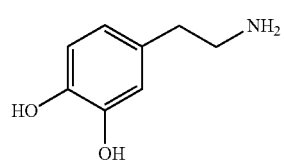 | | 32 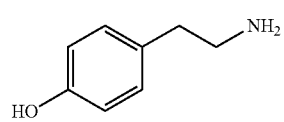 |

-continued
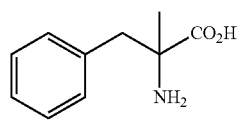
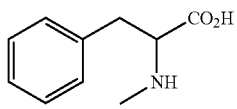
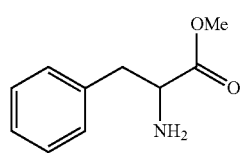
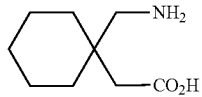
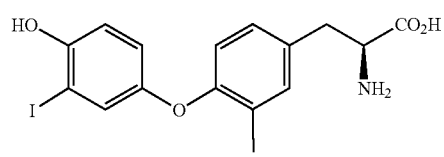
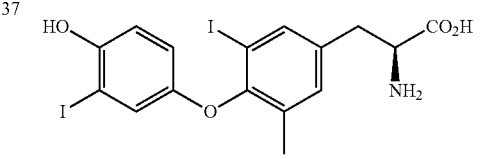
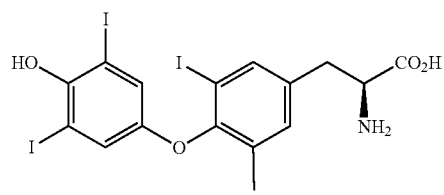
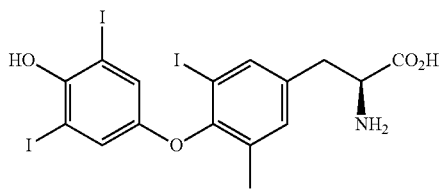
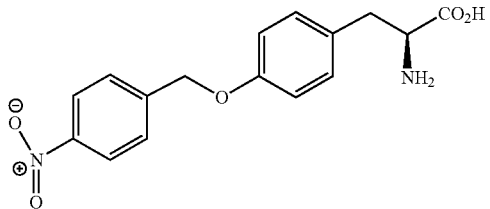
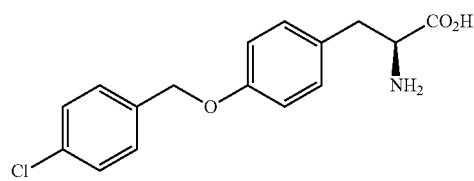
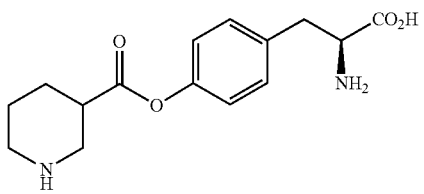
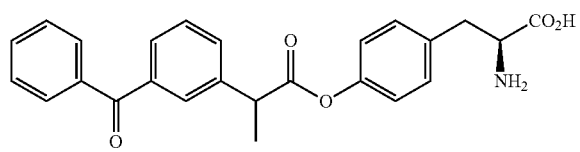
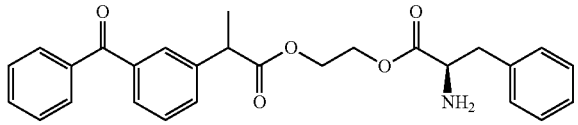
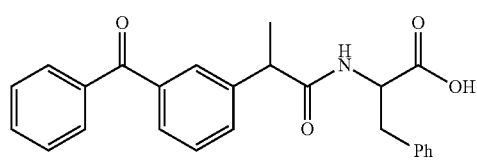
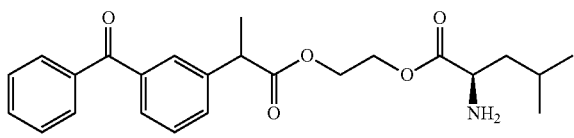
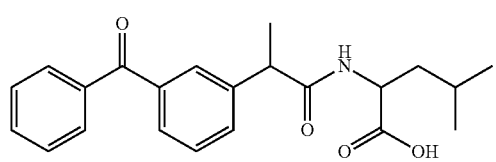
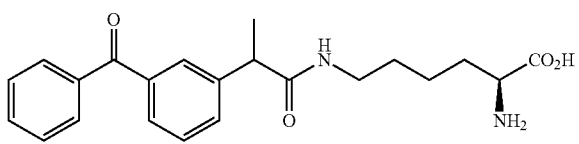

-continued
| 51 | 52 |
|---|---|
| 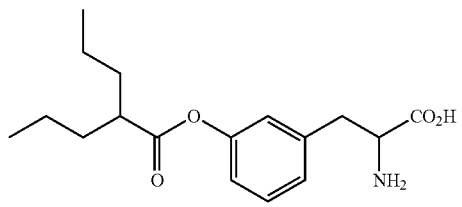 | 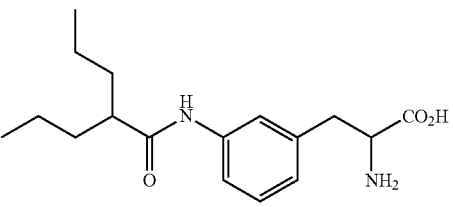 |
| 53 | 54 |
| 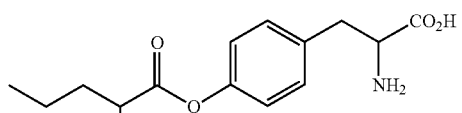 | 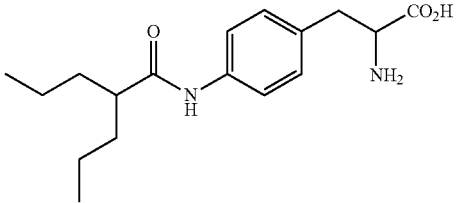 |
| 55 | 56 |
| 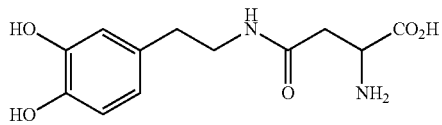 | 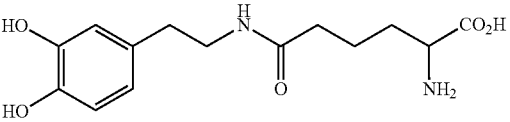 |
| 57 | 58 |
| 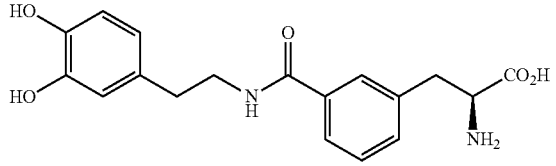 | 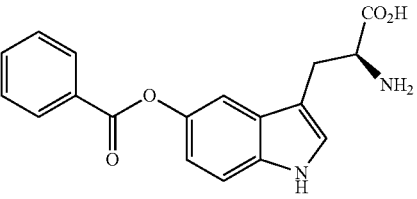 |
| 59 | 60 |
| 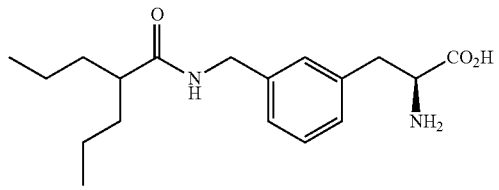 | 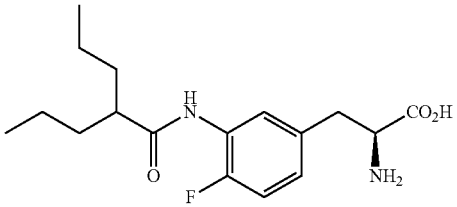 |
| 61 | 62 |
| 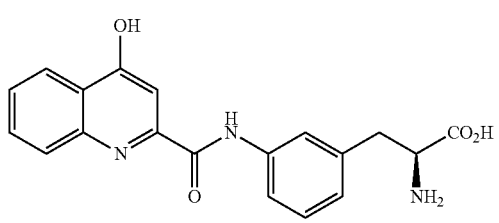 | 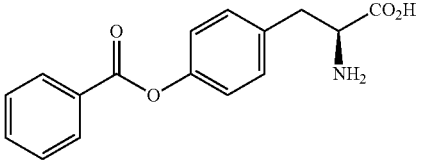 |
| 63 | 64 |
| 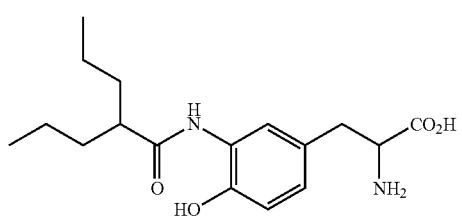 | 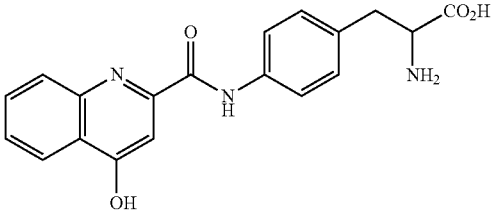 |
| 65 | 66 |
| 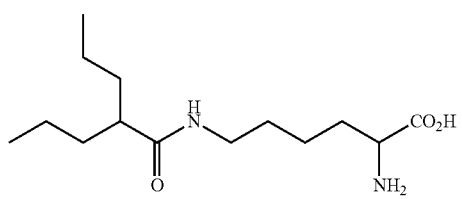 | 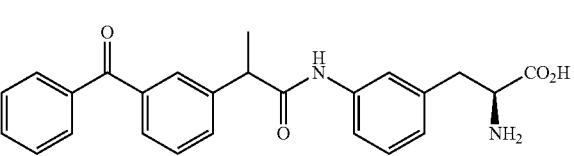 |

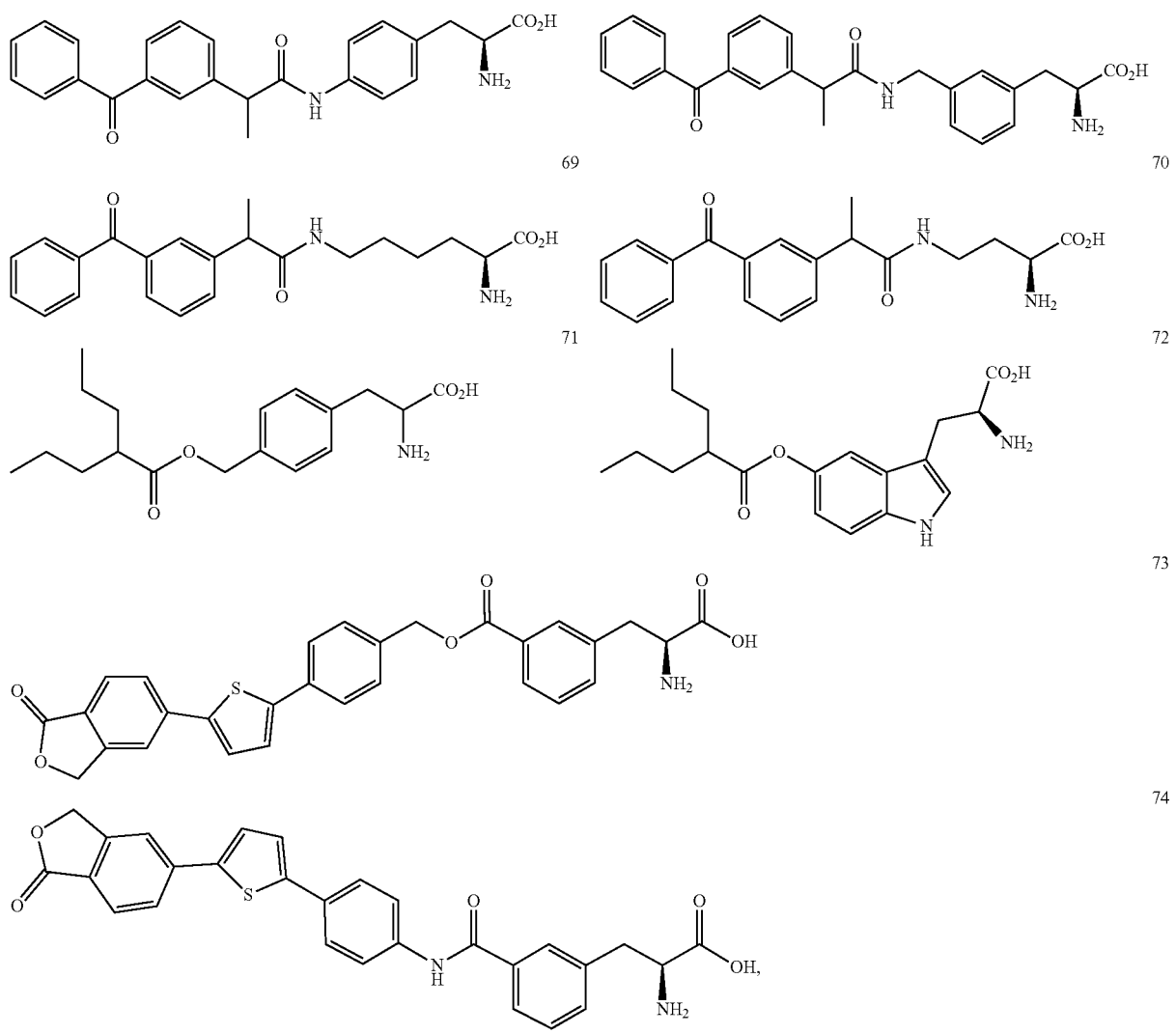
or any combination thereof.
In some aspects, the LAT1 ligand is a LAT1-targeting prodrug shown below.
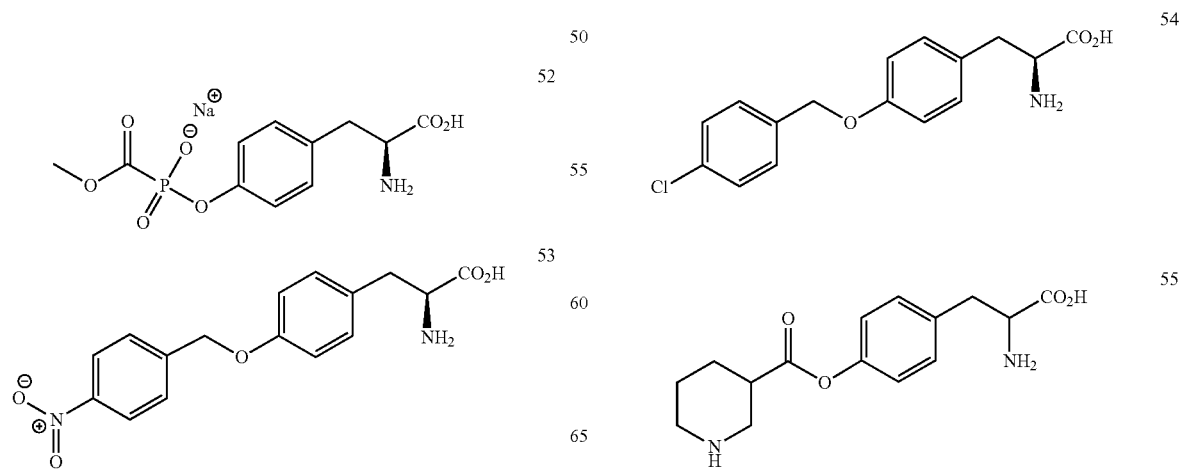

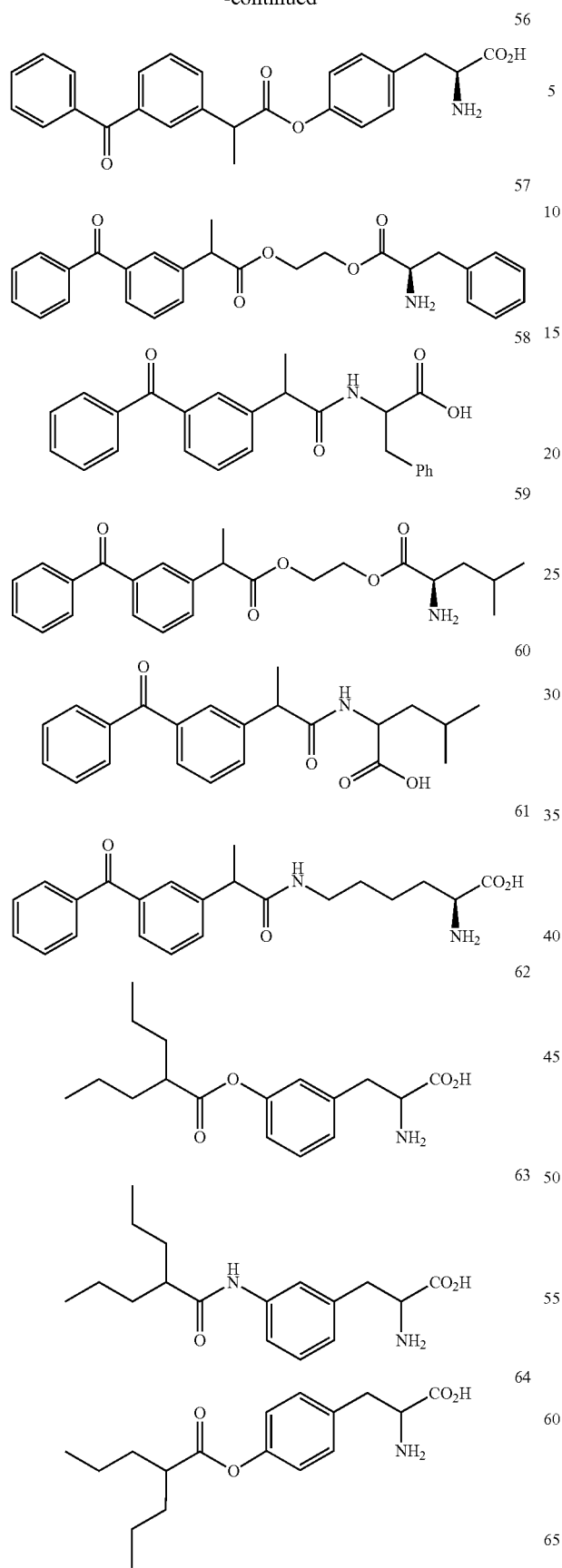
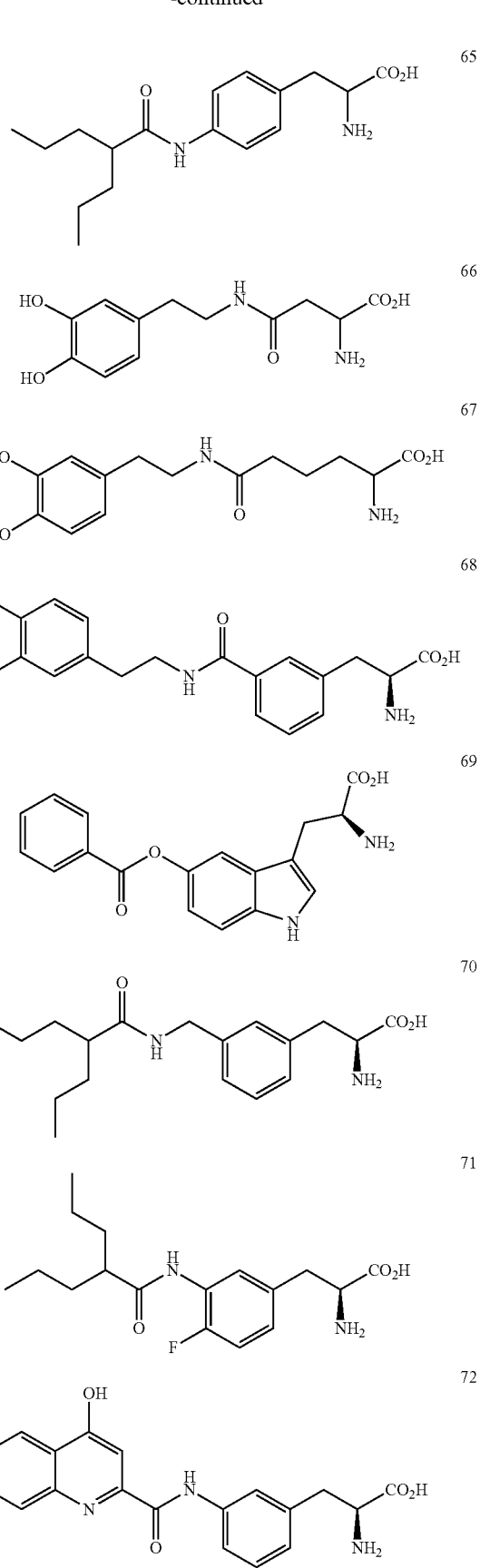

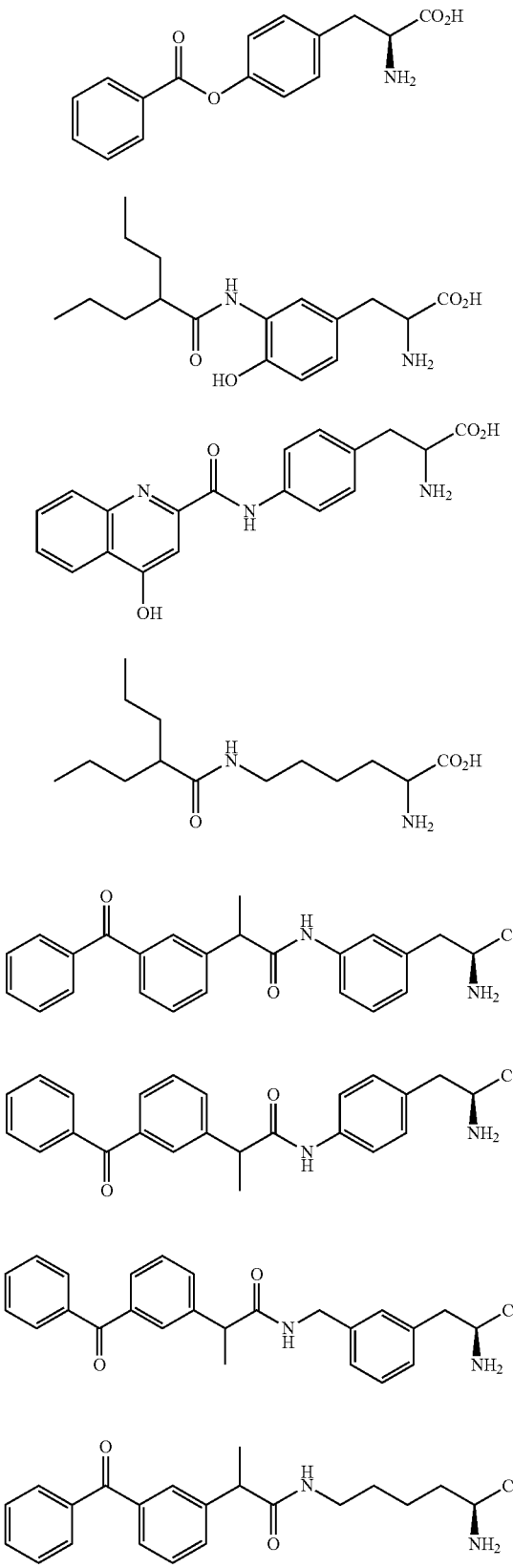

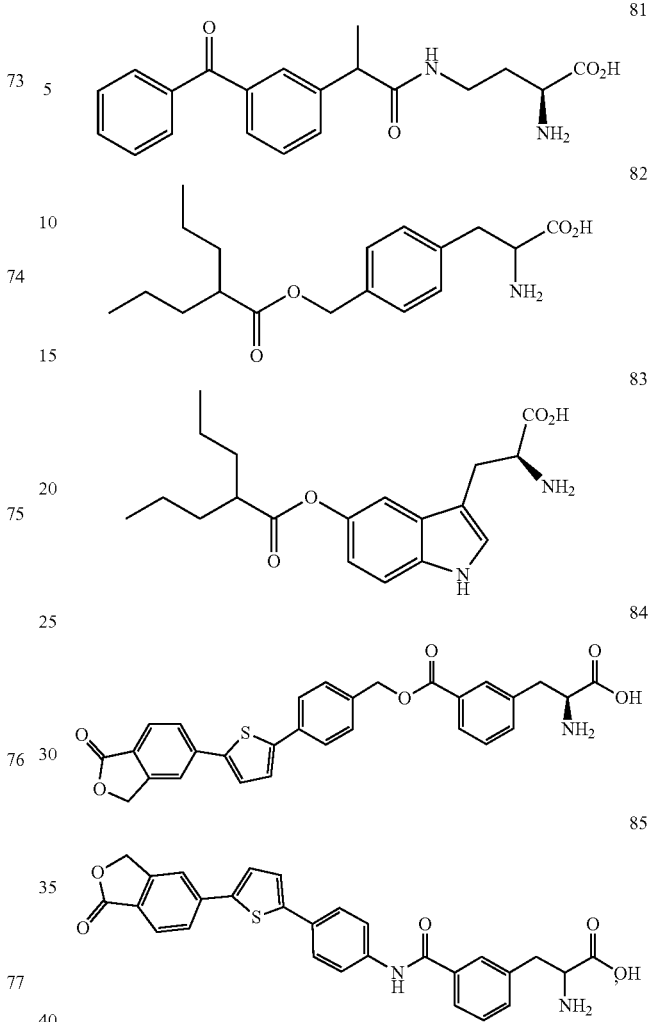

or any combination thereof.

See Singh & Ecker (2018) "Insights into the Structure, Function, and Ligand Discovery of the Large Neutral Amino Acid Transporter 1, LAT1," Int. J. Mol. Sci. 19:1278; Geier et al. (2013) "Structure-based ligand discovery for the Large-neutral Amino Acid Transporter 1, LAT-1," Proc. Natl. Acad. Sci. USA 110:5480-85; and Chien et al. (2018) "Reevaluating the Substrate Specificity of the L-type Amino Acid Transporter (LAT1)," J. Med. Chem. 61:7358-73, which are herein incorporated by reference in their entireties.

In some aspects, the carrier units of the present disclosure comprise:

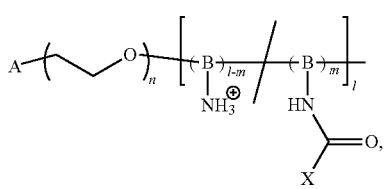

wherein A is tryptophan or phenylalanine, and B is a cationic carrier moiety, e.g., lysine.

wherein,
(i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;
(ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and,
(iii) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

and wherein X is

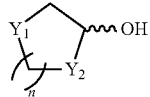

and n is 1 or 2; $Y_1$ is C, N, O, or S, and $Y_2$ is C, N O, or S, and n is 1 or 2, e.g., vitamin B3.

In some aspects, the carrier units of the present disclosure comprise:

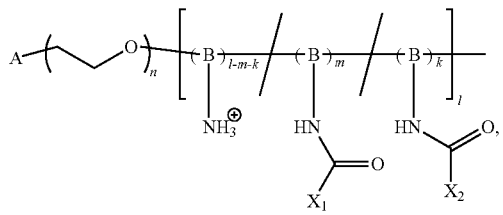

wherein A is tryptophan or phenylalanine, and B is a cationic carrier moiety, e.g., lysine,
wherein,
(i) l is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;
(ii) m is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150;
(iii) k is an integer between 1 to 150, e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150; and,
(iv) n is an integer between about 1 and about 200; e.g., about 2 and about 10, about 10 and about 20, about 20 and about 30, about 30 and about 40, about 40 and about 50, about 50 and about 60, about 60 and about 70, about 70 and about 80, about 80 and about 90, about 90 and about 100, about 100 and about 110, about 110 and about 120, about 120 and about 130, about 130 and about 140, about 140 and about 150, about 150 and about 160, about 160 and about 170, about 170 and about 180, about 180 and about 190, or about 190 and about 200;

wherein $X_1$ is

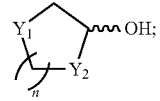

wherein $Y_1$ is C, N, O, or S, and $Y_2$ is C, N O, or S, and n is 1 or 2; and wherein $X_2$ is

wherein p=0 to 5. In some aspects, p is 0. In some aspects, $X_2$ is SH.

Non-limiting examples of targeting moieties are described below.

i. Ligands

A ligand functions as a type of targeting moiety defined as a selectively bindable material that has a selective (or specific), affinity for another substance. The ligand is recognized and bound by a usually, but not necessarily, larger specific binding body or "binding partner," or "receptor." Examples of ligands suitable for targeting are antigens, haptens, biotin, biotin derivatives, lectins, galactosamine and fucosylamine moieties, receptors, substrates, coenzymes and cofactors among others.

When applied to the micelles of the present disclosure a ligand includes an antigen or hapten that is capable of being bound by, or to, its corresponding antibody or fraction thereof. Also included are viral antigens or hemagglutinins and neuraminidases and nucleocapsids including those from any DNA and RNA viruses, AIDS, HIV and hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picornaviruses, poxviruses, reoviruses, rhabdoviruses, rhinoviruses, togaviruses and viroids; any bacterial antigens including those of gram-negative and gram-positive bacteria, *Acinetobacter, Achromobacter, Bacteroides, Clostridium, Chlamydia*, enterobacteria, *Haemophilus, Lactobacillus, Neisseria*, Staphyloccus, or Streptoccocus; any fungal antigens including those of *Aspergillus, Candida*, Coccidiodes, mycoses, phycomycetes, and yeasts; any *mycoplasma* antigens; any rickettsial antigens; any protozoan antigens; any parasite antigens; any human antigens including those of blood cells, virus infected cells, genetic markers, heart diseases, oncoproteins, plasma proteins, complement factors, rheumatoid factors. Included are cancer and tumor antigens such as alpha-fetoproteins, prostate specific antigen (PSA) and CEA, cancer markers and oncoproteins, among others.

Other substances that can function as ligands for targeting a micelle of the present disclosure are certain vitamins (i.e. folic acid, Bua), steroids, prostaglandins, carbohydrates, lipids, antibiotics, drugs, digoxins, pesticides, narcotics, neuro-transmitters, and substances used or modified such that they function as ligands.

In some aspects, the targeting moiety comprises a protein or protein fragment (e.g., hormones, toxins), and synthetic or natural polypeptides with cell affinity. Ligands also include various substances with selective affinity for ligators that are produced through recombinant DNA, genetic and molecular engineering. Except when stated otherwise, the ligands of the instant disclosure also include ligands as defined in U.S. Pat. No. 3,817,837, which is herein incorporated by reference in its entirety.

ii. Ligators

A ligator functions as a type of targeting moiety defined for this disclosure as a specific binding body or "partner" or "receptor," that is usually, but not necessarily, larger than the ligand it can bind to. For the purposes of this disclosure, it can be a specific substance or material or chemical or "reactant" that is capable of selective affinity binding with a specific ligand. A ligator can be a protein such as an antibody, a nonprotein binding body, or a "specific reactor."

When applied to this disclosure, a ligator includes an antibody, which is defined to include all classes of antibodies, monoclonal antibodies, chimeric antibodies, Fab fractions, fragments and derivatives thereof. The term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, scFab, (scFab)$_2$, (scFv)$_2$, Fab, Fab', and F(ab')$_2$, F(ab 1)$_2$, Fv, dAb, and Fd fragments, diabodies, and antibody-related polypeptides. Antibody includes bispecific antibodies and multispecific antibodies so long as they exhibit the desired biological activity or function. In some aspects of the present disclosure, the targeting moiety is an antibody or a molecule comprising an antigen binding fragment thereof. In some aspects, the antibody is a nanobody. In some aspects, the antibody is an ADC. The terms "antibody-drug conjugate" and "ADC" are used interchangeably and refer to an antibody linked, e.g., covalently, to a therapeutic agent (sometimes referred to herein as agent, drug, or active pharmaceutical ingredient) or agents. In some aspects of the present disclosure, the targeting moiety is an antibody-drug conjugate.

Under certain conditions, the instant disclosure is also applicable to using other substances as ligators. For instance, other ligators suitable for targeting include naturally occurring receptors, any hemagglutinins and cell membrane and nuclear derivatives that bind specifically to hormones, vitamins, drugs, antibiotics, cancer markers, genetic markers, viruses, and histocompatibility markers. Another group of ligators includes any RNA and DNA binding substances such as polyethylenimine (PEI) and polypeptides or proteins such as histones and protamines.

Other ligators also include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, ribosomes, bacteriophages, cytochromes, lectins, certain resins, and organic polymers.

Targeting moieties also include various substances such as any proteins, protein fragments or polypeptides with affinity for the surface of any cells, tissues or microorganisms that are produced through recombinant DNA, genetic and molecular engineering. Thus, in some aspects, the targeting moiety directs a micelle of the present disclosure to a specific tissue (i.e., liver tissue or brain tissue), to a specific type of cell (e.g., a certain type of cancer cells), or to a physiological compartment or physiological barrier (e.g., the BBB).

e. Linkers

As described above, a cationic carrier unit disclosed herein can comprise, as shown, e.g., in FIG. 3, one or more linkers. As used herein, the term "linker" refers to a peptide or polypeptide sequence (e.g., a synthetic peptide or polypeptide sequence), or a non-peptide linker for which its main function is to connect two moieties in a cationic carrier unit disclosed herein. In some aspects, cationic carrier units of the present disclosure can comprise at least one linker connecting a tissue-specific targeting moiety (TM) with a water soluble polymer (WS), at least one linker connecting a water-soluble biopolymer (WP) with cationic carrier (CC) or an adjuvant moiety (AM), at least one linker connecting a cationic carrier (CC) with an adjuvant moiety (AM), or any combination thereof. In some aspects, two or more linkers can be linked in tandem.

When multiple linkers are present in a cationic carrier unit disclosed herein, each of the linkers can be the same or different. Generally, linkers provide flexibility to the cationic carrier unit. Linkers are not typically cleaved; however, in certain aspects, such cleavage can be desirable. Accordingly, in some aspects a linker can comprise one or more protease-cleavable sites, which can be located within the sequence of the linker or flanking the linker at either end of the linker sequence.

In one aspect, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker can comprise at least about 110, at least about 120, at least about 130, at least about 140, at least about 150, at least about 160, at least about 170, at least about 180, at least about 190, or at least about 200 amino acids.

In other aspects, the peptide linker can comprise at least about 200, at least about 250, at least about 300, at least about 350, at least about 400, at least about 450, at least about 500, at least 550, at least about 600, at least about 650, at least about 700, at least about 750, at least about 800, at least about 850, at least about 900, at least about 950, or at least about 1,000 amino acids.

The peptide linker can comprise between 1 and about 5 amino acids, between 1 and about 10 amino acids, between 1 and about 20 amino acids, between about 10 and about 50 amino acids, between about 50 and about 100 amino acids, between about 100 and about 200 amino acids, between about 200 and about 300 amino acids, between about 300 and about 400 amino acids, between about 400 and about 500 amino acids, between about 500 and about 600 amino acids, between about 600 and about 700 amino acids, between about 700 and about 800 amino acids, between about 800 and about 900 amino acids, or between about 900 and about 1000 amino acids.

Examples of peptide linkers are well known in the art. In some aspects, the linker is a glycine/serine linker. In some aspects, the peptide linker is glycine/serine linker according to the formula [(Gly)n-Ser]m where n is any integer from 1 to 100 and m is any integer from 1 to 100. In other aspects the glycine/serine linker is according to the formula [(Gly)x-Sery]z (SEQ ID NO: 1) wherein x in an integer from 1 to 4, y is 0 or 1, and z is an integers from 1 to 50. In one aspect, the peptide linker comprises the sequence Gn, where n can be an integer from 1 to 100. In a specific aspect, the sequence of the peptide linker is GGGG (SEQ ID NO: 2).

In some aspects, the peptide linker can comprise the sequence (GlyAla)n (SEQ ID NO: 3), wherein n is an integer between 1 and 100. In other aspects, the peptide linker can comprise the sequence (GlyGlySer)n (SEQ ID NO: 4), wherein n is an integer between 1 and 100.

In other aspects, the peptide linker comprises the sequence (GGGS)n (SEQ ID NO: 5). In still other aspects, the peptide linker comprises the sequence (GGS)n (GGGGS)n (SEQ ID NO: 6). In these instances, n can be an integer from 1-100. In other instances, n can be an integer from one to 20, i.e., 1, 2, 3, 4, 5, 6, 7, 8, 9, 10, 11, 12, 13, 14, 15, 16, 17, 18, 19, or 20.

Examples of linkers include, but are not limited to, GGG, SGGSGGS (SEQ ID NO: 7), GGSGGSGGSGGSGGG (SEQ ID NO: 8), GGSGGSGGGGSGGGS (SEQ ID NO: 9), GGSGGSGGSGGSGGSGGS (SEQ ID NO: 10), or GGGGSGGGGSGGGGS (SEQ ID NO: 11). In other aspects, the linker is a poly-G sequence (GGGG)n (SEQ ID NO: 12), where n can be an integer from 1-100.

In one aspect, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion). In another aspect, the peptide linker can comprise non-naturally occurring amino acids. In another aspect, the peptide linker can comprise naturally occurring amino acids occurring in a linear sequence that does not occur in nature. In still another aspect, the peptide linker can comprise a naturally occurring polypeptide sequence.

In some aspects, the linker comprises a non-peptide linker. In other aspects, the linker consists of a non-peptide linker. In some aspects, the non-peptide linker can be, e.g., maleimido caproyl (MC), maleimido propanoyl (MP), methoxyl polyethyleneglycol (MPEG), succinimidyl 4-(N-maleimidomethyl)-cyclohexane-1-carboxylate (SMCC), m-maleimidobenzoyl-N-hydroxysuccinimide ester (MBS), succinimidyl 4-(p-maleimidophenyl)butyrate (SMPB), N-succinimidyl(4-iodoacetyl)aminobenzonate (SIAB), succinimidyl 6-[3-(2-pyridyldithio)-propionamide]hexanoate (LC-SPDP), 4-succinimidyloxycarbonyl-alpha-methyl-alpha-(2-pyridyldithio)toluene (SMPT), etc. (see, e.g., U.S. Pat. No. 7,375,078).

Linkers can be introduced into polypeptide sequences using techniques known in the art (e.g., chemical conjugation, recombinant techniques, or peptide synthesis). Modifications can be confirmed by DNA sequence analysis. In some aspects, the linkers can be introduced using recombinant techniques. In other aspects, the linkers can be introduced using solid phase peptide synthesis. In certain aspects, a cationic carrier unit disclosed herein can contain simultaneously one or more linkers that have been introduced using recombinant techniques and one or more linkers that have been introduced using solid phase peptide synthesis or methods of chemical conjugation known in the art. In some aspects, the linker comprises a cleavage site.

III. Payloads

As used herein the term "payload" refers to a biologically active molecule, e.g., a therapeutic agent or a that can interactive by itself or via an adapter with a cationic carrier unit of the present disclosure, and be included within the core of a micelle of the present disclosure. Payloads contemplated in the present disclosure include but are not limited to therapeutic drugs, e.g., prodrugs, anticancer drugs, antineoplastic drugs, antifungal drugs, antibacterial drugs, antiviral drugs, cardiac drugs, neurological drugs, and drugs of abuse; alkaloids, antibiotics, bioactive peptides, steroids, steroid hormones, polypeptide hormones, interferons, interleukins, narcotics, nucleic acids including antisense oligonucleotides, pesticides and prostaglandins. Biologically active molecules also include any toxins including aflatoxins, ricins, bungarotoxins, irinotecan, ganciclovir, furosemide, indomethacin, chlorpromazine, methotrexate, cevine derivatives and analogs including cevadines, desatrines, and veratridine, among others.

Biologically active molecules also include but are not limited to, various flavone derivatives and analogs including dihydroxyflavones (chrysins), trihydroxyflavones (apigenins), pentahydroxyflavones (morins), hexahydroxyflavones (myricetins), flavyliums, quercetins, fisetins; various antibiotics including derivatives and analogs such as penicillin derivatives (i.e. ampicillin), anthracyclines (i.e. doxorubicin, daunorubicin, mitoxantrone), butoconazole, camptothecin, chalcomycin, chartreusin, chrysomicins (V and M), chloramphenicol, chlorotetracyclines, clomocyclines, cyclosporins, ellipticines, filipins, fungichromins, griseofulvin, griseoviridin, guamecyclines, macrolides (i.e. amphotericins, chlorothricin), methicillins, nystatins, chrymutasins, elsamicin, gilvocarin, ravidomycin, lankacidin-group antibiotics (i.e. lankamycin), mitomycin, teramycins, tetracyclines, wortmannins; various anti-microbials including reserpine, spironolactone, sulfacetamide sodium, sulphonamide, thiamphenicols, thiolutins; various purine and pyrimidine derivatives and analogs including 5'-fluorouracil 5'-fluoro-2'-deoxyuridine, and allopurinol; various photosensitizer substances, especially those used for singlet and triplet oxygen formation useful for photodynamic therapy (van Lier, J. E. In "Photodynamic Therapy of Neoplastic Disease"; Kessel, D., Ed., CRC Press, Boca Raton, FL, 1990, Vol. 1), including meso-chlorin e6 monoethylenediamine (Mce6), phytalocyanine, porphyrins and their derivatives and analogs; various steroidal compounds such as cortisones, estradiols, hydrocortisone, testosterones, prednisolones, progesterones, dexamethasones, beclomethasones and other methasone derivatives, other steroid derivatives and analogs including cholesterols, digitoxins, digoxins, digoxigenins; various coumarin derivatives and analogs including dihydroxycoumarins (esculetins), dicumarols, chrysarobins, chrysophanic acids, emodins, secalonic acids; various dopas, derivatives and analogs including dopas, dopamines, epinephrines, and norepinephrines (arterenols); various antineoplastic agents or cell growth inhibitors such as cisplatins and taxanes including paclitaxel and docetaxel; various barbiturates including phenobarbitone, amobarbital, allobarbital, pentobarbital and other barbital derivatives; various benzene derivatives including amino-benzoic acid, bromobenzoic acid, benzocaine, benzodiazepines, benzothiazide, butyl-p-aminobenzoate; various polypeptide derivatives; various carboxylic acid derivatives such as bromoisovalerylurea, phenyl-butyric acid, phenylvaleric acid, or any combination thereof.

Other biologically active molecules include, but are not limited to, diphenyl hydantoin, adiphenine, anethole, aspirin, azopropazone, bencyclane, chloralhydrate, chlorambucil, chlorpromazine, chlorogenin, cinnamic acid, clofibrate, coenzyme A, cyclohexyl anthranilate, diazepam, flufenamic acid, fluocinolone acetonide, flurbiprofen, guaiazulene, ibuprofen, indican, indomethacin, iodine, ketoprofen, mefanamic acid, menadione, metronidazole, nitrazepam, phenytoin, propylparaben, proscillaridin, quinolone, thalidomide, thiamine dilaurylsulphate, thiopental, triamcinolone, vitamins A, D3, E, K3, warfarin, or any combination thereof.

Other biologically active molecules are anti-viral drugs, nucleic acids and other anti-viral substances including those against any DNA and RNA viruses, AIDS, HIV and hepatitis viruses, adenoviruses, alphaviruses, arenaviruses, coronaviruses, flaviviruses, herpesviruses, myxoviruses, oncornaviruses, papovaviruses, paramyxoviruses, parvoviruses, picornaviruses, poxviruses, reoviruses, thabdoviruses, rhinoviruses, togaviruses and viriods; any anti-bacterial drugs, nucleic acids and other anti-bacterial substances including those against gram-negative and grampositive bacteria, *Acinetobacter, Achromobacter, Bacteroides, Clostridium, Chlamydia,* enterobacteria, *Haemophilus, Lactobacillus, Neisseria,* Staphyloccus, or Streptoccocus; any antifungal drugs, nucleic acids and other anti-fungal substances including those against *Aspergillus, Candida,* Coccidiodes, mycoses, phycomycetes, and yeasts; any drugs, nucleic acids and other substances against *mycoplasma* and *rickettsia*; any anti-protozoan drugs, nucleic acids and other substances; any anti-parasitic drugs, nucleic acids and other substances; any drugs, nucleic acids and other substances against heart diseases, tumors, and virus infected cells, among others.

(a) Nucleic Acids

In some aspects, the biologically active molecule (payload) is a nucleic acid, e.g., an RNA or a DNA. Nucleic acid active agents suitable for delivery using the micelles of the present disclosure include all types of RNA and all types of DNA, including also oligonucleotides such as probes and primers used in the polymerase chain reaction (PCR), hybridizations, or DNA sequencing. In some aspects, the nucleic acid comprises mRNA, miRNA, miRNA sponge, tough decoy miRNA (TD), antimir (antagomir), small RNA, rRNA, siRNA, shRNA, gDNA, cDNA, pDNA, PNA, BNA, antisense oligonucleotide (ASO), aptamer, cyclic dinucleotide, or any combination thereof.

In some aspects, the biologically active molecule (payload) comprises a short interfering RNA (siRNA), which is a double-stranded RNA that can induce sequence-specific post-transcriptional gene silencing, thereby decreasing or even inhibiting gene expression. For example, siRNAs can trigger the specific degradation of homologous RNA molecules, such as mRNAs, within the region of sequence identity between both the siRNA and the target RNA. Non limiting exemplary siRNAs are disclosed in WO 02/44321, which is incorporated by reference in its entirety.

In some aspects, the biologically active molecule (payload) comprises a short hairpin RNAs (shRNAs). In some aspects, the biologically active molecule comprises an miRNA or a miRNA inhibitor (antimiR). In some aspects, the biologically active molecule (payload) can be 10-30 nucleotides in length, for example from 14-25 nucleotides in length. In some aspects, the biologically active molecule (payload) has a length of 16-30 nucleotides, 18-25 nucleotides, particularly 18, 19, 20, 21, 22, 23, 24, or 25 nucleotides.

Sequences for miRNAs are available publicly, for example, through the miRBase registry (Griffiths-Jones, et al., Nucleic Acids Res., 36 (Database Issue):D154-D158 (2008); Griffiths-Jones, et al., Nucleic Acids Res., 36 (Database Issue):D140-D144 (2008); Griffiths-Jones, et al., Nucleic Acids Res., 36 (Database Issue):D109-D111 (2008)) and other publically accessible databases.

In some aspects, the miRNA inhibitors are oligomers or polymers of ribonucleic acid (RNA) or deoxyribonucleic acid (DNA) or modifications thereof. In some aspects, the miRNA antagonists are antimir. Antimirs are a specific class of miRNA inhibitors that are described, for example, in US2007/0213292 to Stoffel et al. Antimirs are RNA-like oligonucleotides that contain various modifications for RNase protection and pharmacologic properties such as enhanced tissue and cellular uptake. Antimirs differ from normal RNA by having complete 2'-O-methylation of sugar, phosphorothioate backbone and a cholesterol-moiety at 3'-end.

Non limiting examples of antimirs and other miRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901, all of which are hereby incorporated by reference.

In some aspects, the nucleic acids are phosphodiester antisense oligonucleotides, and any oligonucleotides where the sugar-phosphate "backbone" has been derivatized or replaced with "backbone analogues" such as with phosphorothioate, phosphorodithioate, phosphoroamidate, alkyl phosphotriester, or methylphosphonate linkages. In some aspects, the nucleic acids active agents are antisense oligonucleotides, and any oligonucleotides or oligodeoxynucleotides with non-phosphorous backbone analogues such as sulfamate, 3'-thioformacetal, methylene(methylimino) (MMI), 3'-N-carbamate, or morpholino carbamate.

In some aspects, the biologically active molecule (payload) is an antimir. As used herein, the terms "antimir," "anti microRNA," "anti miRNA," and variants thereof refer to molecules (e.g., synthetically generated molecules) that are used to neutralize microRNA (miRNA) function in cells for desired responses. miRNA are complementary sequences (approx. 20-22 bp) to mRNA that are involved in the cleavage of RNA or the suppression of the translation. By controlling the miRNA that regulate mRNAs in cells, antimirs (also called anti-miRNA oligonucleotides, AMOs, or antagomirs) can be used as further regulation as well as for therapeutic for certain cellular disorders. This regulation can occur through a steric blocking mechanism as well as hybridization to miRNA.

These interactions within the body between antimirs and a miRNA can be for therapeutics in disorders in which over/under expression occurs or aberrations in miRNA lead to coding issues. Some of the miRNA linked disorders that are encountered in the humans include cancers, muscular diseases, autoimmune disorders, and viruses.

Various components of antimirs can be manipulated to affect the binding affinity and potency of the antimir. The 2'-sugar of the antimirs can be modified to be substituted with fluorine and various methyl groups, almost all with an increase in binding affinity. However, some of these modified 2'-sugar antimirs lead to negative effects on cell growth. Modifying the 5'-3' phosphodiester backbone linkage to a phosphorothioate (P—S) backbone linkage is also known to have an effect on target affinity. Using the P—S mutation was shown to decrease the Tm of the oligonucleotide, which leads to a lower target affinity. A final requirement for antimirs is mismatch specificity and length restrictions. Due to miRNAs in the same families sharing "seed" (shared) sequences and differ by only a couple of additional nucleotides; one antimir can potentially target multiple miRNA sequences. One or more examples of antimirs or miRNA sequences are shown in the following table.

of AGAGAGGAGAGCCGUGUAUGAC (SEQ ID NO: 18), wherein the nucleotide sequence has one mismatch, two mismatches, three mismatches, or four mismatches. In some aspects, the payload (e.g., antimir) is a nucleotide sequence comprising, consisting essentially of, or consisting of AGAGAGGAGAGCCGUGUAUGAC (SEQ ID NO: 18), wherein the nucleotide sequence has one or two mismatches. In other aspects, the payload (e.g., antimir) is a nucleotide sequence targeting the seed sequence of has-miR-485-3p (UCAUACA; SEQ ID NO: 19). In some aspects, the payload (e.g., antimir) is a nucleotide sequence comprising UCAUACA (SEQ ID NO: 19), wherein U can be optionally T (complement of the seed), wherein the nucleotide sequence is about 10 nucleotides to 30 nucleotides (e.g., 10 to 25, 10 to 24, 10 to 23, 10 to 22, 10 to 21, 10 to 20, 10 to 19, or 10 to 18) in length. In some aspects, the payload (e.g., antimir) is a nucleotide sequence comprising UGUAUGA (SEQ ID NO: 20), wherein U can be optionally T (complement of the seed), wherein the nucleotide sequence comprises one, two three, four, five, six, seven, eight, nine, ten, 11, 12, 13, 14, 15, 16, 17, 18, 19, or 20 nucleic acids at the 5' terminus of the complement of the seed sequence and/or one, two three, four, five, six, seven, eight, nine, ten, 11, 12, 13, 14, 15, 16, 17, 18, 19, or 20 nucleic acids at the 3' terminus of the complement of the seed sequence.

In some aspects, the payload is a nucleotide sequence selected from the group consisting of: 5'-UGUAUGA-3' (SEQ ID NO: 23), 5'-GUGUAUGA-3' (SEQ ID NO: 24), 5'-CGUGUAUGA-3' (SEQ ID NO: 25), 5'-CCGUGUAUGA-3' (SEQ ID NO: 26), 5'-GCCGUGUAUGA-3' (SEQ ID NO: 27), 5'-AGCCGUGUAUGA-3' (SEQ ID NO: 28), 5'-GAGCCGUGUAUGA-3' (SEQ ID NO: 29), 5'-AGAGCCGUGUAUGA-3' (SEQ ID NO: 30), 5'-GAGAGCCGUGUAUGA-3' (SEQ ID NO: 31), 5'-GGAGAGCCGUGUAUGA-3' (SEQ ID NO: 32), 5'-AGGAGAGCCGUGUAUGA-3' (SEQ ID NO: 33), 5'-GAGGAGAGCCGUGUAUGA-3' (SEQ ID NO: 34), 5'-AGAGGAGAGCCGUGUAUGA-3' (SEQ ID NO: 35), 5'-GAGAGGAGAGCCGUGUAUGA-3' (SEQ ID NO: 36);

TABLE 1

| SEQ ID NO for miRNA | Target Score | miRNA Name | Mature miRNA sequence | SEQ ID NO for antimir | Artificial miRNA inhibitor sequence (antimir) |
|---|---|---|---|---|---|
| 13 | 95 | hsa-miR-204-5p | UUCCCUUUGUCAUCCUAUGCCU | 15 | AGGCAUAGGAUGACAAAGGGAA |
| 14 | 89 | hsa-miR-132-3p | UAACAGUCUACAGCCAUGGUCG | 16 | CGACCAUGGCUGUAGACUGGUA |

In some aspects, the payload is a polynucleotide comprising a nucleotide sequence having 5 to 30 nucleotides in length. In some aspects, the polynucleotide has 5, 6, 7, 8, 9, 10, 11, 12, 13, 14, 15, 16, 17, 18, 19, 20, 21, 22, 23, 24, 25, 26, 27, 28, 29, or 30 nucleotides in length. In some aspects, the nucleotide sequence has 15, 16, 17, 18, 19, 20, 21, 22, 23, 24, 25, or 26 nucleotides in length.

In some aspects, the payload (e.g., antimir) is a nucleotide sequence targeting hsa-miR-485, e.g., hsa-miR-485-3p. In some aspects, the hsa-miR-485-3p has the sequence GUCAUACACGGCUCUCCUCUCU (SEQ ID NO: 17). In some aspects, the payload (e.g., antimir) is a nucleotide sequence comprising, consisting essentially of, or consisting of AGAGAGGAGAGCCGUGUAUGAC (SEQ ID NO: 18), wherein U can be optionally T. In some aspects, the payload (e.g., antimir) is a nucleotide sequence comprising, consisting essentially of, or consisting 5'-UGUAUGAC-3' (SEQ ID NO: 37), 5'-GUGUAUGAC-3' (SEQ ID NO: 38), 5'-CGUGUAUGAC-3' (SEQ ID NO: 39), 5'-CCGUGUAUGAC-3' (SEQ ID NO: 40), 5'-GCCGUGUAUGAC-3' (SEQ ID NO: 41), 5'-AGCCGUGUAUGAC-3' (SEQ ID NO: 42), 5'-GAGCCGUGUAUGAC-3' (SEQ ID NO: 43), 5'-AGAGCCGUGUAUGAC-3' (SEQ ID NO: 44), 5'-GAGAGCCGUGUAUGAC-3' (SEQ ID NO: 45), 5'-GGAGAGCCGUGUAUGAC-3' (SEQ ID NO: 46), 5'-AGGAGAGCCGUGUAUGAC-3' (SEQ ID NO: 47), 5'-GAGGAGAGCCGUGUAUGAC-3' (SEQ ID NO: 48), 5'-AGAGGAGAGCCGUGUAUGAC-3' (SEQ ID NO: 49), or 5'-GAGAGGAGAGCCGUGUAUGAC-3' (SEQ ID NO: 50).

In some aspects, the payload is a nucleotide sequence comprising 5'-TGTATGA-3' (SEQ ID NO: 51), 5'-GTGTATGA-3' (SEQ ID NO: 52), 5'-CGTGTATGA-3' (SEQ ID NO: 53), 5'-CCGTGTATGA-3' (SEQ ID NO: 54), 5'-GCCGTGTATGA-3' (SEQ ID NO: 55), 5'-AGCCGTGTATGA-3' (SEQ ID NO: 56), 5'-GAGCCGTGTATGA-3' (SEQ ID NO: 57), 5'-AGAGCCGTGTATGA-3' (SEQ ID NO: 58), 5'-GAGAGCCGTGTATGA-3' (SEQ ID NO: 59), 5'-GGAGAGCCGTGTATGA-3' (SEQ TD NO: 60), 5'-AGGAGAGCCGTGTATGA-3' (SEQ ID NO: 61), 5'-GAGGAGAGCCGTGTATGA-3' (SEQ ID NO: 62), 5'-AGAGGAGAGCCGTGTATGA-3' (SEQ ID NO: 63), 5'-GAGAGGAGAGCCGTGTATGA-3' (SEQ ID NO: 64); 5'-TGTATGAC-3' (SEQ ID NO: 65), 5'-GTGTATGAC-3' (SEQ ID NO: 66), 5'-CGTGTATGAC-3' (SEQ ID NO: 67), 5'-CCGTGTATGAC-3' (SEQ ID NO: 68), 5'-GCCGTGTATGAC-3' (SEQ ID NO: 69), 5'-AGCCGTGTATGAC-3' (SEQ ID NO: 70), 5'-GAGCCGTGTATGAC-3' (SEQ ID NO: 71), 5'-AGAGCCGTGTATGAC-3' (SEQ ID NO: 72), 5'-GAGAGCCGTGTATGAC-3' (SEQ ID NO: 73), 5'-GGAGAGCCGTGTATGAC-3' (SEQ ID NO: 74), 5'-AGGAGAGCCGTGTATGAC-3' (SEQ ID NO: 75), 5'-GAGGAGAGCCGTGTATGAC-3' (SEQ ID NO: 76), 5'-AGAGGAGAGCCGTGTATGAC-3' (SEQ ID NO: 77), or 5'-GAGAGGAGAGCCGTGTATGAC-3' (SEQ ID NO: 78).

In some aspects, the payload (e.g., antimir) is a nucleotide sequence targeting hsa-miR-204, e.g., has-miR-204-5p. The has-miR-204-5p is shown at TABLE 1 as UUCCCUUUGUCAUCCUAUGCCU (SEQ ID NO: 13). In some aspects, the payload (e.g., antimir) is a nucleotide sequence comprising, consisting essentially of, or consisting of AGGCAUAGGAUGACAAAGGGAA (SEQ ID NO: 15), wherein U can be optionally T. In some aspects, the payload (e.g., antimir) is a nucleotide sequence comprising, consisting essentially of, or consisting of AGGCAUAGGAUGACAAAGGGAA (SEQ ID NO: 15), wherein U can be optionally T and wherein the nucleotide sequence has one mismatch, two mismatches, three mismatches, or four mismatches. In some aspects, the payload (e.g., antimir) is a nucleotide sequence comprising, consisting essentially of, or consisting of AGGCAUAGGAUGACAAAGGGAA (SEQ ID NO: 15), wherein U can be optionally T and wherein the nucleotide sequence has one or two mismatches. In other aspects, the payload (e.g., antimir) is a nucleotide sequence targeting the seed sequence of has-miR-204-5p (UCCCUUU; SEQ ID NO: 21). In some aspects, the payload (e.g., antimir) is a nucleotide sequence comprising AAAGGGA (SEQ ID NO: 22) (complement of the seed), wherein U can be optionally T and wherein the nucleotide sequence is about 10 nucleotides to 30 nucleotides (e.g., 10 to 25, 10 to 24, 10 to 23, 10 to 22, 10 to 21, 10 to 20, 10 to 19, or 10 to 18) in length. In some aspects, the payload (e.g., antimir) is a nucleotide sequence comprising AAAGGGA (SEQ ID NO: 22) (complement to the seed), wherein the nucleotide sequence comprises one, two three, four, five, six, seven, eight, nine, ten, 11, 12, 13, 14, 15, 16, 17, 18, 19, or 20 nucleic acids at the 5' terminus of the complement of the seed sequence and/or one, two three, four, five, six, seven, eight, nine, ten, 11, 12, 13, 14, 15, 16, 17, 18, 19, or 20 nucleic acids at the 3' terminus of the complement of the seed sequence.

i. Chemically Modified Polynucleotides

In some aspects, a polynucleotide of the present disclosure (e.g., an antimir, e.g., an miR485 antimir) comprises at least one chemically modified nucleoside and/or nucleotide. When the polynucleotides of the present disclosure are chemically modified, the polynucleotides can be referred to as "modified polynucleotides."

A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase").

A "nucleotide" refers to a nucleoside including a phosphate group. Modified nucleotides can be synthesized by any useful method, such as, for example, chemically, enzymatically, or recombinantly, to include one or more modified or non-natural nucleosides.

Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some aspects, the modified polynucleotides contain one, two, or more (optionally different) nucleoside or nucleotide modifications. In some aspects, a modified polynucleotide can exhibit one or more desirable properties, e.g., improved thermal or chemical stability, reduced immunogenicity, reduced degradation, increased binding to the target microRNA, reduced non-specific binding to other microRNA or other molecules, as compared to an unmodified polynucleotide.

In some aspects, a polynucleotide of the present disclosure is chemically modified. As used herein in reference to a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population, including, but not limited to, its nucleobase, sugar, backbone, or any combination thereof.

In some aspects, a polynucleotide of the present disclosure (e.g., an antimir) can have a uniform chemical modification of all or any of the same nucleoside type or a population of modifications produced by downward titration of the same starting modification in all or any of the same nucleoside type, or a measured percent of a chemical modification of all any of the same nucleoside type but with random incorporation In another aspect, the polynucleotide of the present disclosure (e.g., an antimir) can have a uniform chemical modification of two, three, or four of the same nucleoside type throughout the entire polynucleotide (such as all uridines and/or all cytidines, etc. are modified in the same way).

Modified nucleotide base pairing encompasses not only the standard adenine-thymine, adenine-uracil, or guanine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleobase inosine and adenine, cytosine, or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s. For example, TD's of the present disclosure can be administered as RNAs, as DNAs, or as hybrid molecules comprising both RNA and DNA units.

In some aspects, the polynucleotide (e.g., an antimir, e.g., an miR485 antimir) includes a combination of at least two (e.g., 2, 3, 4, 5, 6, 7, 8, 8, 10, 11, 12, 13, 14, 15, 16, 17, 18, 18, 20 or more) modified nucleobases.

In some aspects, the nucleobases, sugar, backbone linkages, or any combination thereof in a polynucleotide (e.g., an antimir, e.g., an miR485 antimir) are modified by at least about 5%, at least 10%, at least 15%, at least 20%, at least 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or 100%.

1. Base Modifications

In certain aspects, the chemical modification is at nucleobases in a polynucleotide of the present disclosure (e.g., an antimir, e.g., an miR485 antimir). In some aspects, the at least one chemically modified nucleoside is a modified uridine (e.g., pseudouridine (ψ), 2-thiouridine (s2U), 1-methyl-pseudouridine (m1ψ), 1-ethyl-pseudouridine (e1ψ), or 5-methoxyuridine (mo5U)), a modified cytosine (e.g., 5-methyl-cytidine (m5C)) a modified adenosine (e.g., 1-methyl-adenosine (m1A), N6-methyl-adenosine (m6A), or 2-methyl-adenine (m2A)), a modified guanosine (e.g., 7-methyl-guanosine (m7G) or 1-methyl-guanosine (m1G)), or a combination thereof.

In some aspects, the polynucleotide of the present disclosure (e.g., an antimir, e.g., an miR485 antimir) is uniformly modified (e.g., fully modified, modified throughout the entire sequence) for a particular modification. For example, a polynucleotide can be uniformly modified with the same type of base modification, e.g., 5-methyl-cytidine (m5C), meaning that all cytosine residues in the polynucleotide sequence are replaced with 5-methyl-cytidine (m5C). Similarly, a polynucleotide can be uniformly modified for any type of nucleoside residue present in the sequence by replacement with a modified nucleoside such as any of those set forth above.

In some aspects, the polynucleotide of the present disclosure (e.g., an antimir, e.g., an miR485 antimir) includes a combination of at least two (e.g., 2, 3, 4 or more) of modified nucleobases. In some aspects, at least about 5%, at least 10%, at least 15%, at least 20%, at least 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or 100% of a type of nucleobases in a polynucleotide of the present disclosure (e.g., an antimir, e.g., an miR485 antimir) are modified nucleobases.

2. Backbone Modifications

In some aspects, the payload can comprise a "polynucleotide of the present disclosure" (for example comprising an antimir, e.g., an miR485 antimir), wherein the polynucleotide includes any useful modification to the linkages between the nucleosides. Such linkages, including backbone modifications, that are useful in the composition of the present disclosure include, but are not limited to the following: 3-alkylene phosphonates, 3'-amino phosphoramidate, alkene containing backbones, aminoalkylphosphoramidates, aminoalkylphosphotriesters, boranophosphates, —CH$_2$—O—N(CH$_3$)—CH$_2$—, —CH$_2$—N(CH$_3$)—N(CH$_3$)—CH$_2$—, —CH$_2$—NH—CH$_2$—, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, —N(CH$_3$)—CH$_2$—CH$_2$—, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

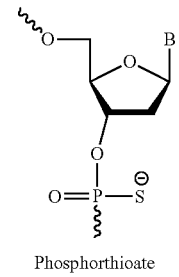

Phosphorthioate

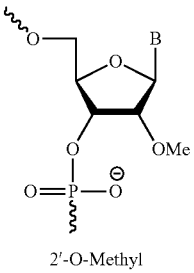

2'-O-Methyl

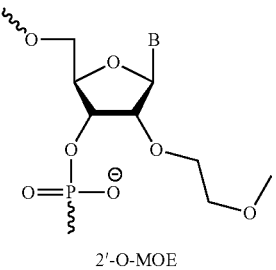

2'-O-MOE

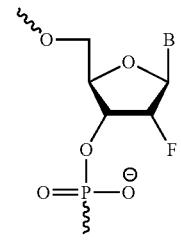

2'-Fluoro

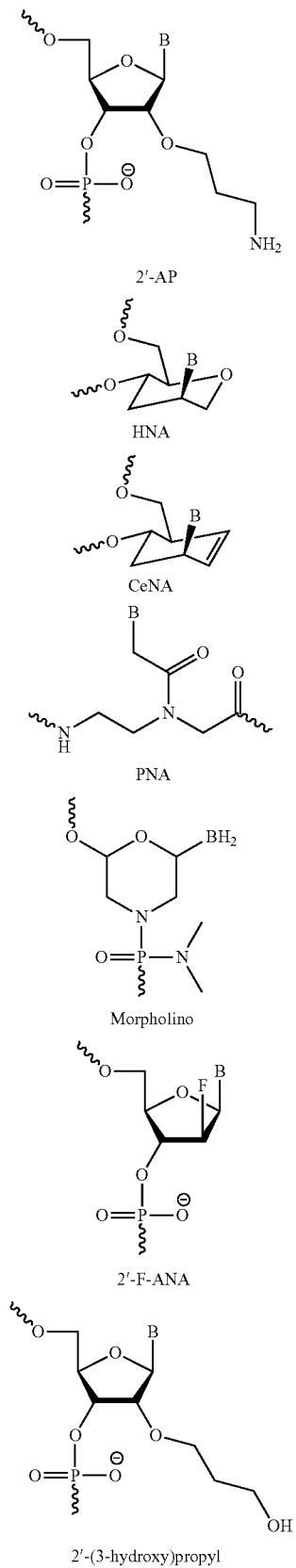

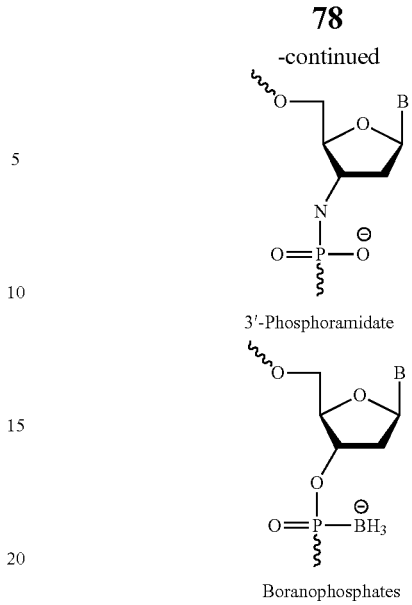

In some aspects, the presence of a backbone linkage disclosed above increase the stability (e.g., thermal stability) and/or resistance to degradation (e.g., enzyme degradation) of a polynucleotide of the present disclosure (e.g., an antimir, e.g., an miR485 antimir). In some aspects, the stability and/or resistance to degradation increases by at least about 10%, at least about 15%, at least about 20%, at least about 20%, at least about 35%, at least about 30%, at least about 40%, at least about 450%, at least about 50%, at least about 550%, at least about 60%, at least about 60%, at least about 700%, at least about 7500 at least about 800%, at least about 850%, at least about 900%, at least about 95%, or at least about 100% in the modified polynucleotide compared to a corresponding polynucleotide without the modification (reference or control polynucleotide)

In some aspects, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or 100% of the backbone linkages in a polynucleotide of the present disclosure ((e.g., an antimir, e.g., an miR485 antimir) are modified (e.g., all of them are phosphorothioate).

In some aspects, 1, 2, 3, 4, 5, 6, 7, 8, 9, 10, 11, 12, 13, 14, 15, 16, 17, 18, 19, 20, or 21 backbone linkages in a polynucleotide of the present disclosure (e.g., an antimir, e.g., an miR485 antimir) are modified (e.g., phosphorothioate).

In some aspects, the backbone comprises linkages selected from the group consisting of phosphodiester linkage, phosphotriesters linkage, methylphosphonate linkage, phosphoramidate linkage, phosphorothioate linkage, and combinations thereof.

3. Sugar Modifications

The modified nucleosides and nucleotides which can be incorporated into a polynucleotide of the present disclosure (e.g., an antimir, e.g., an miR485 antimir), can be modified on the sugar of the nucleic acid. Thus, in some aspects, the payload comprises a nucleic acid, wherein the nucleic comprises at least one nucleoside analog (e.g., a nucleoside with a sugar modification).

In some aspects, the sugar modification increases the affinity of the binding of a polynucleotide to its target miRNA. Incorporating affinity-enhancing nucleotide analogues in the polynucleotide, such as LNA or 2'-substituted sugars can allow the length of polynucleotide to be reduced, and also may reduce the upper limit of the size a polynucleotide before non-specific or aberrant binding takes place.

In some aspects, at least about 5%, at least about 10%, at least about 15%, at least about 20%, at least about 25%, at least about 30%, at least about 35%, at least about 40%, at least about 450%, at least about 50%, at least about 550%, at least about 60%, at least about 650%, at least about 70%, at least about 75%, at least about 80%, at least about 85%, at least about 90%, at least about 9500 at least about 960%, at least about 9700 at least about 980%, at least about 9900 or 10000 of the nucleotides in a polynucleotide of the present disclosure (e.g., an antimir, e.g., an miR485 antimir) contain sugar modifications (e.g., LNA).

In some aspects, 1, 2, 3, 4, 5, 6, 7, 8, 9, 10, 11, 12, 13, 14, 15, 16, 17, 18, 19, 20, 21, or 22 nucleotide units in a polynucleotide of the present disclosure (e.g., an antimir, e.g., an miR485 antimir) are sugar modified (e.g., LNA).

Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

The 2' hydroxyl group (OH) of ribose can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —O(CH$_2$CH$_2$O)$_n$CH$_2$CH$_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges include methylene, propylene, ether, amino bridges, aminoalkyl, aminoalkoxy, amino, and amino acid.

In some aspects, nucleoside analogues present in a polynucleotide of the present disclosure (e.g., an antimir, e.g., an miR485 antimir) comprise, e.g., 2'-O-alkyl-RNA units, 2'-OMe-RNA units, 2'-O-alkyl-SNA, 2'-amino-DNA units, 2'-fluoro-DNA units, LNA units, arabino nucleic acid (ANA) units, 2'-fluoro-ANA units, HNA units, INA (intercalating nucleic acid) units, 2'MOE units, or any combination thereof. In some aspects, the LNA is, e.g., oxy-LNA (such as beta-D-oxy-LNA, or alpha-L-oxy-LNA), amino-LNA (such as beta-D-amino-LNA or alpha-L-amino-LNA), thio-LNA (such as beta-D-thio0-LNA or alpha-L-thio-LNA), ENA (such a beta-D-ENA or alpha-L-ENA), or any combination thereof.

In some aspects, nucleoside analogs present in a polynucleotide of the present disclosure comprise Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), or any combination thereof.

In some aspects, a polynucleotide of the present disclosure (e.g., an antimir, e.g., an miR485 antimir) can comprise both modified RNA nucleotide analogues (e.g., LNA) and DNA units. In some aspects, a polynucleotide of the present disclosure is a gapmer. See, e.g., U.S. Pat. Nos. 8,404,649; 8,580,756; 8,163,708; 9,034,837; all of which are herein incorporated by reference in their entireties. In some aspects, a polynucleotide of the present disclosure is a micromir. See U.S. Pat. Appl. Publ. No. US20180201928, which is herein incorporated by reference in its entirety.

IV. Micelles

The present disclosure also provides micelles comprising the cationic carrier units of the present disclosure. The micelles of the present disclosure comprise cationic carriers unit of the present disclosure and negatively charged payload, wherein the negatively charged payload and the cationic carrier unit are associate with each other. In some aspects, the association is comprises a covalent bond (see FIG. 1). In other aspects, the association does not comprise a covalent bond (see FIG. 1). In other aspects, the association is via an ionic bond, i.e., via electrostatic interaction. In some aspects, the negatively charged payload (e.g., a DNA and/or RNA) is not conjugated to the cationic carrier unit by a covalent bond and/or the negatively charged payload interacts with the cationic carrier moiety of the cationic carrier unit only via an ionic interaction.

In some aspects, the cationic carrier units and micelles of the present disclosure protect the payload (e.g., a DNA and/or RNA) from degradation (e.g., by a DNase and/or an RNase). First, the cationic carrier unit is capable of protecting the payload through electrostatic interaction. Secondly, the micelle sequesters the payload to the core of the micelle, i.e., out of the reach of DNases and/or an RNases. In some aspects, the protection of the payload from circulating enzymes (e.g., nucleases) can increase the half-life of the negatively charged payload (e.g., a DNA and/or RNA) compared to the free payload. In some aspects, encapsulation of the payload in a micelle of the present disclosure can increase the plasma half-life of the payload at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, or at least about 30-fold compared to the free payload.

In some aspects, the positive charge of the cationic carrier unit, and in particular the charge of the cationic carrier moiety is sufficient to form a micelle when mixed with a negatively charged payload (e.g., a nucleic acid) in a solution, wherein the overall ionic ratio between the cationic carrier unit, in particular its cationic carrier moiety, and the negatively charged payload (e.g., a nucleic acid) is about 1:1. In some aspects, the overall ionic ratio between the cationic carrier unit, in particular its cationic carrier moiety, and the negatively charged payload (e.g., a nucleic acid) is higher than 1:1, i.e., an excess of cationic carrier unit is used. In some aspects, the overall ionic ratio between the cationic carrier unit, in particular its cationic carrier moiety, and the negatively charged payload (e.g., a nucleic acid) is lower than 1:1, i.e., an excess of negatively change payload is used.

In some aspects, upon combination with a suitable buffer (e.g., PBS), the complexes formed between the cationic carrier units of the present disclosure and payload (e.g., an antisense oligonucleotides such as an antimir), self-organize to yield micelles. See FIG. 5.

A micelle is a water soluble or colloidal structure or aggregate composed of one or more amphiphilic molecules. Amphiphilic molecules are those that contain at least one hydrophilic (polar) moiety and at least one hydrophobic (nonpolar) moiety. "Classic micelles" have a single, central and primarily hydrophobic zone or "core" surrounded by a hydrophilic layer or "shell." In aqueous solution, the micelle forms an aggregate with the hydrophilic "head" regions of the amphiphilic molecule in contact with the surrounding solvent, sequestering the hydrophobic single-tail regions of the amphiphilic molecule in the micelle core. Micelles are approximately spherical in shape. Other shapes, e.g., ellipsoids, cylinders, rod-like structures, or polymersomes are also possible. The shape and size, and therefore loading capacity, of the micelles disclosed can be modified by altering the ratio between water-soluble biopolymer (e.g., PEG) and cationic carrier (e.g., poly lysine). Depending on the ratio, the carrier units can organize as small particles, small micelles, micelles, rod-like structures, or polymersomes (see FIG. 6). Thus, the term "micelles of the present disclosure" encompasses not only classic micelles but also small particles, small micelles, micelles, rod-like structures, or polymersomes.

The micelles of the present disclosure can be composed of either a single monomolecular polymer containing hydrophobic and hydrophilic moieties or an aggregate mixture containing many amphiphilic (i.e. surfactant) molecules formed at or above the critical micelle concentration (CMC), in a polar (i.e. aqueous) solution. The micelle is self-assembled from one or more amphiphilic molecules where the moieties are oriented to provide a primarily hydrophobic interior core and a primarily hydrophilic exterior.

Figure 9:
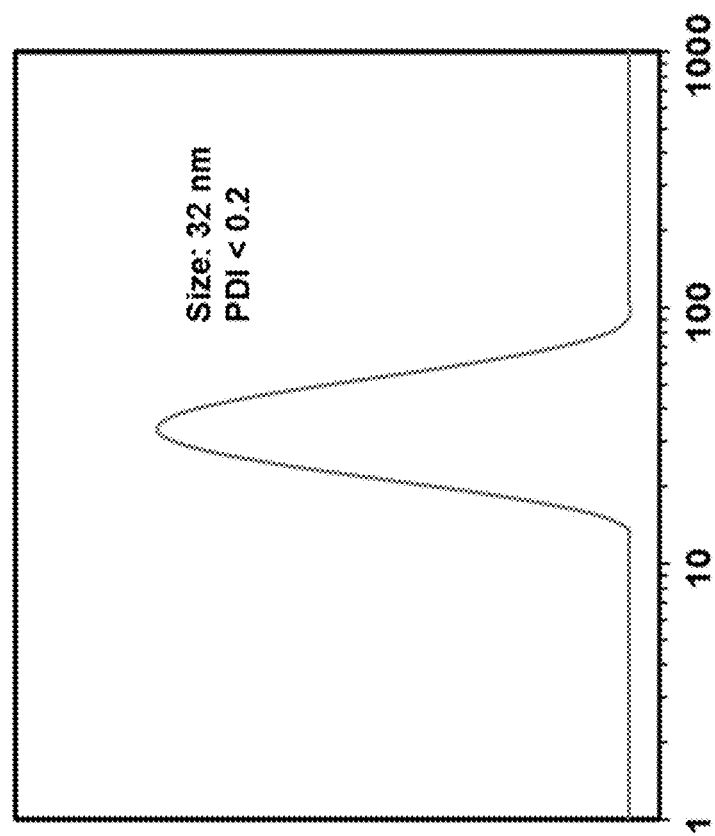
FIG. 9 shows particle size distribution of oligonucleotide (e.g., anti-miRNA)-loaded micelles of the present disclosure in PBS. Oligonucleotide (e.g., anti-miRNA)-loaded micelles show a 32 nm particle size with low PDI (polydispersity index) distribution which indicates that the population of micelles is homogeneous.

Micelles of the present disclosure can range in size from 5 to about 2000 nanometers. In some aspects, the diameter of the micelle is between about 10 nm and about 200 nm. In some aspects, the diameter of the micelle is between about 1 nm and about 100 nm, between about 10 nm and about 100 nm, between about 10 nm and about 90 nm, between about 10 nm and about 80 nm, between about 10 nm and about 70 nm, between about 20 nm and about 100 nm, between about 20 nm and about 90 nm, between about 20 nm and about 80 nm, between about 20 nm and about 70 nm, between about 30 nm and about 100 nm, between about 30 nm and about 90 nm, between about 30 nm and about 80 nm, between about 30 nm and about 70 nm, between about 40 nm and about 100 nm, between about 40 nm and about 90 nm, between about 40 nm and about 80 nm, or between about 43 nm and about 76 nm. In some aspects, the diameter of the micelles of the present disclosure is between about 30 nm and about 60 nm. In some aspects, the diameter of the micelles of the present disclosure is between about 15 nm and about 90 nm. In some aspects, the diameter of the micelles of the present disclosure is between about 15 nm and about 80 nm. In some aspects, the diameter of the micelles of the present disclosure is between about 15 nm and about 70 nm. In some aspects, the diameter of the micelles of the present disclosure is between about 15 nm and about 60 nm. In some aspects, the diameter of the micelles of the present disclosure is between about 15 nm and about 50 nm. In some aspects, the diameter of the micelles of the present disclosure is between about 20 nm and about 60 nm. In some aspects, the diameter of the micelles of the present disclosure is between about 20 nm and about 50 nm. In some aspects, the diameter of the micelles of the present disclosure is between about 20 nm and about 40 nm. In some aspects, the diameter of the micelles of the present disclosure is between about 25 nm and about 35 nm. In some aspects, the diameter of the micelles of the present disclosure is about 32 nm. An exemplary distribution of micelles sizes is shown in FIG. 9.

In some aspects, the micelle can comprise a single type of antimir, e.g., miR485 antimir. In other aspects, the micelle can comprise more than one type antimir, e.g., (i) antimir with different architectures targeting the same miRNA; (ii) antimir with different architectures targeting different miRNAs; (iii) antimir with the same architecture targeting the same miRNA; or, (iv) combinations thereof.

In some aspects, the micelles of the present disclosure comprise a single type of cationic carrier unit. In other aspects, the micelles of the present disclosure comprise more than one type of cationic carrier unit (e.g., targeting different receptor on the surface of a target cell). In some aspects, micelles of the present disclosure can comprise cationic carrier units with different targeting moieties, different cationic carrier moieties (e.g., to accommodate different payloads), and/or different adjuvant units.

In order to form a micelle with a payload, different types of cationic or anionic carrier unit can be combined together. For example, in order to target blood brain barrier, the micelle of the present disclosure can comprise a cationic (or an anionic) carrier unit linked to a targeting moiety and a cationic (or an anionic) carrier unit not linked to a targeting moiety. In some aspects, a micelle comprises about 50 to about 200 cationic or anionic carrier units. In other aspects, a micelle comprises about 50 to about 150, about 50 to about 140, about 50 to about 130, about 50 to about 120, about 50 to about 110, or about 50 to about 100 cationic or anionic carrier units. In some aspects, a micelle comprises about 60 to about 200 cationic or anionic carrier units. In other aspects, a micelle comprises about 60 to about 150, about 60 to about 140, about 60 to about 130, about 60 to about 120, about 60 to about 110, about 60 to about 100, about 60 to about 90, about 60 to about 80, or about 60 to about 70 cationic or anionic carrier units. In some aspects, a micelle comprises about 70 to about 200 cationic or anionic carrier units. In other aspects, a micelle comprises about 70 to about 150, about 70 to about 140, about 70 to about 130, about 70 to about 120, about 70 to about 110, about 70 to about 100, about 70 to about 90, or about 70 to about 80 cationic or anionic carrier units. In some aspects, a micelle comprises about 80 to about 200 cationic or anionic carrier units. In other aspects, a micelle comprises about 80 to about 150, about 80 to about 140, about 80 to about 130, about 80 to about 120, about 80 to about 110, about 80 to about 100, or about 80 to about 90 cationic or anionic carrier units. In some aspects, a micelle comprises about 90 to about 200 cationic or anionic carrier units. In other aspects, a micelle comprises about 90 to about 150, about 90 to about 140, about 90 to about 130, about 90 to about 120, about 90 to about 110, or about 90 to about 100 cationic or anionic carrier units. In some aspects, a micelle comprises about 100 to about 200 cationic or anionic carrier units. In other aspects, a micelle comprises about 100 to about 150, about 100 to about 140, about 100 to about 130, about 100 to about 120, about 100 to about 110, or about 100 to about 100 cationic or anionic carrier units.

The present disclosure also includes a micelle comprising (i) a nucleotide sequence (e.g., an oligonucleotide about 14, 15, 16, 17, 18, 19, 20, 21, 22, 23, or 24 nucleotides in length) and (ii) a cationic carrier unit described herein. In some aspects, the disclosure is directed to a micelle comprising (i) a nucleotide sequence, e.g., miRNA, or a miRNA inhibitor (e.g., an oligonucleotide about 14, 15, 16, 17, 18, 19, 20, 21, 22, 23, or 24 nucleotides in length), and (ii) about 80 to about 120 (e.g., about 85 to about 115, about 90 to about 110, about 95 to about 105) cationic carrier units described herein, e.g., TM-WP-CC-AM, WP-CC-AM, or a combination thereof (see FIG. 3). In some aspects, the micelle comprises (i) a nucleotide sequence, e.g., miRNA, or a miRNA inhibitor (e.g., an oligonucleotide about 14, 15, 16, 17, 18, 19, 20, 21, 22, 23, or 24 nucleotides in length), and (ii) about 80 to about 120 (e.g., about 80, about 85, about 90, about 95, about 100, about 105, or about 110) of a cationic carrier unit described herein, e.g., optional TM-WP-CC-AM (see FIG. 3). In some aspects, the micelle comprises (i) a nucleotide sequence, e.g., miRNA, or a miRNA inhibitor (e.g., an oligonucleotide about 14, 15, 16, 17, 18, 19, 20, 21, 22, 23, or 24 nucleotides in length), and (ii) about 90 to about 110, e.g., about 100, cationic carrier units, wherein (a) about 45 to about 55, e.g., about 50 of the cationic carrier units comprise TM-WP-CC-AM and (b) about 45 to about 55, e.g., about 50 of the cationic carrier units comprise WP-CC-CM, wherein TM is phenyl alanine, WP is (PEG)$_{5000}$, and CC is about 40 to about 50 lysines, e.g., about 45, about 46, about 47, about 48, about 49, or about 50 lysines, and wherein each of about 5 to about 15 of lysines, about 10 lysines, is fused to Vitamin B3 (nicotinamide).

In some aspects, a micelle of the present disclosure comprises (i) a nucleotide sequence, e.g., a miR485-3p inhibitor, e.g., 5'-AGAGAGGAGAGCCGUGUAUGAC-3' (SEQ ID NO:18), and (ii) about 100 cationic carrier units, wherein (a) about 50 of the cationic carrier units comprise TM-WP-CC-AM and (b) about 50 of the cationic carrier units comprise WP-CC-CM, wherein TM is phenyl alanine, WP is (PEG)$_{5000}$, and CC is about 47 lysines, and wherein each of about 10 lysines is fused to Vitamin B3 (nicotinamide).

In some aspects, the micelle can comprise a single payload (e.g., a single oligonucleotide, e.g., an antimir). In other aspects, the micelle can comprise more than one payload (e.g., multiple oligonucleotides, e.g., multiple antimirs).

V. Methods of Manufacture

The present disclosure also provides methods of making the cationic carrier units and micelles of the present disclosure. In general, the present disclosure provides a method of preparing a cationic carrier unit of the present disclosure comprising synthesizing the cationic carrier unit as described, e.g., in the Examples section. As used herein, the term "synthesizing" refers the assembling the cationic carrier unit using methods known in the art. For example, protein components (e.g., an antibody targeting moiety) can be prepared recombinantly and subsequently conjugated to the other components of the cationic carrier units. In some aspects, each one of the components of the cationic carrier unit can be prepared using methods known in the art, e.g., recombinant protein production, solid phase peptide or nucleic acid synthesis, chemical synthesis, enzymatic synthesis, or any combination thereof, and the resulting component can be conjugated using chemical and/or enzymatic methods known in the art.

The cationic carrier units of the present disclosure can be purified to remove contaminants. In some aspects, the cationic carrier unit comprises a uniform population of cationic carrier units. However, in other aspects, the cationic carrier unit can comprise multiple species (e.g., some of them comprising a targeting moiety, and some comprising the remaining moieties but without a targeting moiety). In some aspects, the manufacture of the cationic carrier units of the present disclosure comprise lyophilization or any other form of dry storage suitable for reconstitution. In some aspects, the preparation of the cationic carrier unit in a dry form takes place after combination of the cationic carrier units with the payload (e.g., a nucleic acid).

In some aspects, the method of preparing a micelle of the present disclosure comprises mixing the cationic carrier unit with the negatively charged payload (e.g., a nucleic acid such an antisense oligonucleotide, e.g., an antimir) at an ionic ratio of 1:1. In some aspects, the cationic carrier unit and the negatively charged payload are combined in solution. In some aspects, after combination of the cationic carrier and the negative charged payload in solution, the resulting solution is lyophilized or dried. In some aspects, the combination of the cationic carrier and the negative charged payload is conducted in dry form.

As shown in FIG. 6, the ratio of number n of monomer units in the water-soluble polymer (A, e.g., PEG) to the number m of monomer units (e.g., lysines) in the cationic carrier moiety (B, e.g., poly lysine), wherein the number of units n or m in each case can be up to 1,000 units affects the size and shape of the resulting micelles. At mB/(nA+mB) ratios of 0.5, the micelles obtained are classic micelles. If mB/(nA+mB) is above 0.5, the micelles obtained are rod like micelles or polymersomes. If mB/(nA+mB) is below 0.5, the micelles obtained are small micelles or small particles.

The micelles of the present disclosure can be generation using any of the techniques known in the art, for example, vortexing, extrusion, or sonication. The formation of micelles depends on applying conditions that are above the critical micelle concentration (CMC) of a solution comprising the cationic carrier units of the present disclosure. After they reach a certain value of concentration, surfactants begin to associate and to organize themselves into more complex units, such as micelles. The CMC of a solution comprising the cationic carriers of the present disclosure can be determined by any physical property (e.g., surface tension) that shows a distinct transition around the CMC.

The well-known Smith-Ewart theory predicts that the number of particles nucleated leading to the formation of micelles above the CMC is proportional to the surfactant (in the present disclosure, the cationic carrier units complexed or associated to the anionic payload) concentration to the 0.6 power. This is so because for a given surfactant the number of micelles formed generally increases with an increase in the surfactant concentration.

In some aspects, the micelles of the present disclosure can be purified, e.g., to remove contaminants and/or to generate an uniform population of micelles (e.g., micelles having the same size, or micelles having the same payload or the same targeting moiety).

IV. Pharmaceutical Compositions

The present disclosure also provides pharmaceutical compositions comprising cationic carrier units and/or micelles of the present disclosure (i.e., micelles comprising cationic carrier units of the present disclosure) that are suitable for administration to a subject. As discussed above, micelles of the present disclosure can be homogeneous (i.e., all micelles comprises the same type of cationic carrier unit, with the same targeting moiety and the same payload). However, in other aspects, the micelles can comprise multiple targeting moieties, multiple payloads, etc.

The pharmaceutical compositions generally comprise a cationic carrier unit and/or micelle of the present disclosure and a pharmaceutically-acceptable excipient or carrier in a form suitable for administration to a subject. Pharmaceutically acceptable excipients or carriers are determined in part by the particular composition being administered, as well as by the particular method used to administer the composition.

There is a wide variety of suitable formulations of pharmaceutical compositions comprising micelles of the present disclosure (See, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration. In some aspects, the pharmaceutical composition comprises one or more micelles described herein.

In certain aspects, the micelles described herein are co-administered with one or more additional therapeutic agents, in a pharmaceutically acceptable carrier. In some aspects, the pharmaceutical composition comprising the micelles described herein is administered prior to administration of the additional therapeutic agent(s). In other aspects, the pharmaceutical composition comprising the micelles described herein is administered after the administration of the additional therapeutic agent(s). In further aspects, the pharmaceutical composition comprising the micelles described herein is administered concurrently with the additional therapeutic agent(s).

In some aspects, the pharmaceutical carrier is added following micelle formation. In other aspects, the pharmaceutical carrier is added before micelle formation.

Acceptable carriers, excipients, or stabilizers are nontoxic to recipients (e.g., animals or humans) at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the cationic carrier units or micelles disclosed herein, use thereof in the compositions is contemplated.

Supplementary therapeutic agents can also be incorporated into the compositions of the present disclosure. Typically, a pharmaceutical composition is formulated to be compatible with its intended route of administration. The micelles described herein can be administered by parenteral, topical, intravenous, oral, subcutaneous, intra-arterial, intradermal, transdermal, rectal, intracranial, intraperitoneal, intranasal, intratumoral, intramuscular route or as inhalants. In certain aspects, the pharmaceutical composition micelles described herein is administered intravenously, e.g. by injection. The micelles described herein can optionally be administered in combination with other therapeutic agents that are at least partly effective in treating the disease, disorder or condition for which the micelles described herein are intended.

Solutions or suspensions can include the following components: a sterile diluent such as water, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, and sodium chloride can be added to the composition. Prolonged absorption of the injectable compositions can be brought about by including in the composition a compound which delays absorption, e.g., aluminum monostearate and gelatin.

Pharmaceutical compositions of the present disclosure can be sterilized by conventional, well known sterilization techniques. Aqueous solutions can be packaged for use or filtered under aseptic conditions and lyophilized, the lyophilized preparation being combined with a sterile aqueous solution prior to administration.

Sterile injectable solutions can be prepared by incorporating the micelles described herein in an effective amount and in an appropriate solvent with one or a combination of ingredients enumerated herein, as desired. Generally, dispersions are prepared by incorporating the micelles described herein into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The micelles described herein can be administered in the form of a depot injection or implant preparation which can be formulated in such a manner to permit a sustained or pulsatile release of the micelles described herein.

Systemic administration of compositions comprising micelles described herein can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain aspects the pharmaceutical composition comprising micelles described herein is administered intravenously into a subject that would benefit from the pharmaceutical composition. In certain aspects, the composition is administered to the lymphatic system, e.g., by intralymphatic injection or by intranodal injection (see e.g., Senti et al., PNAS 105(46): 17908 (2008)), or by intramuscular injection, by subcutaneous administration, by intratumoral injection, by direct injection into the thymus, or into the liver.

In certain aspects, the pharmaceutical composition comprising micelles described herein is administered as a liquid suspension. In certain aspects, the pharmaceutical composition is administered as a formulation that is capable of forming a depot following administration. In certain preferred aspects, the depot slowly releases the micelles described herein into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the micelles described herein and optionally a pharmaceutically active or therapeutic agent. The therapeutic agent can be a biological agent, a small molecule agent, or a nucleic acid agent.

Dosage forms are provided that comprise micelles described herein. In some aspects, the dosage form is formulated as a liquid suspension for intravenous injection.

The micelles disclosed herein or pharmaceutical composition comprising the micelles may be used concurrently with other drugs. To be specific, the micelles or pharmaceutical compositions of the present disclosure may be used together with medicaments such as hormonal therapeutic agents, chemotherapeutic agents, immunotherapeutic agents, medicaments inhibiting the action of cell growth factors or cell growth factor receptors and the like.

V. Methods of Treatment and Use

The present disclosure also provides methods of treating a disease or condition in a subject in need thereof comprising administering a micelle of the present disclosure or a combination thereof to the subject, e.g., a mammal, such as human subject. In some aspects, the present disclosure provides a method of treating a neurodegenerative disorder or cancer in a subject in need thereof, comprising administering to the subject a therapeutically effective amount of a micelle of the present disclosure, or a pharmaceutical composition of the present disclosure.

In some aspects, the micelles of the present disclosure can administered via intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

In some aspects, the micelles of the present disclosure can be used concurrently with other medicaments or treatment suitable for the treatment of the diseases and conditions disclosed herein.

The present disclosure also provides methods to encapsulate a payload for delivery, comprising incorporating the payload, e.g., an anionic payload such as a nucleic acid (e.g., an antimir) into a micelle of the present disclosure.

The present disclosure also provides methods to increase the resistance of a payload to degradation (e.g., nuclease-mediated degradation), comprising incorporating the payload, e.g., an anionic payload such as a nucleic acid (e.g., an antimir) into a micelle of the present disclosure.

Figure 7:
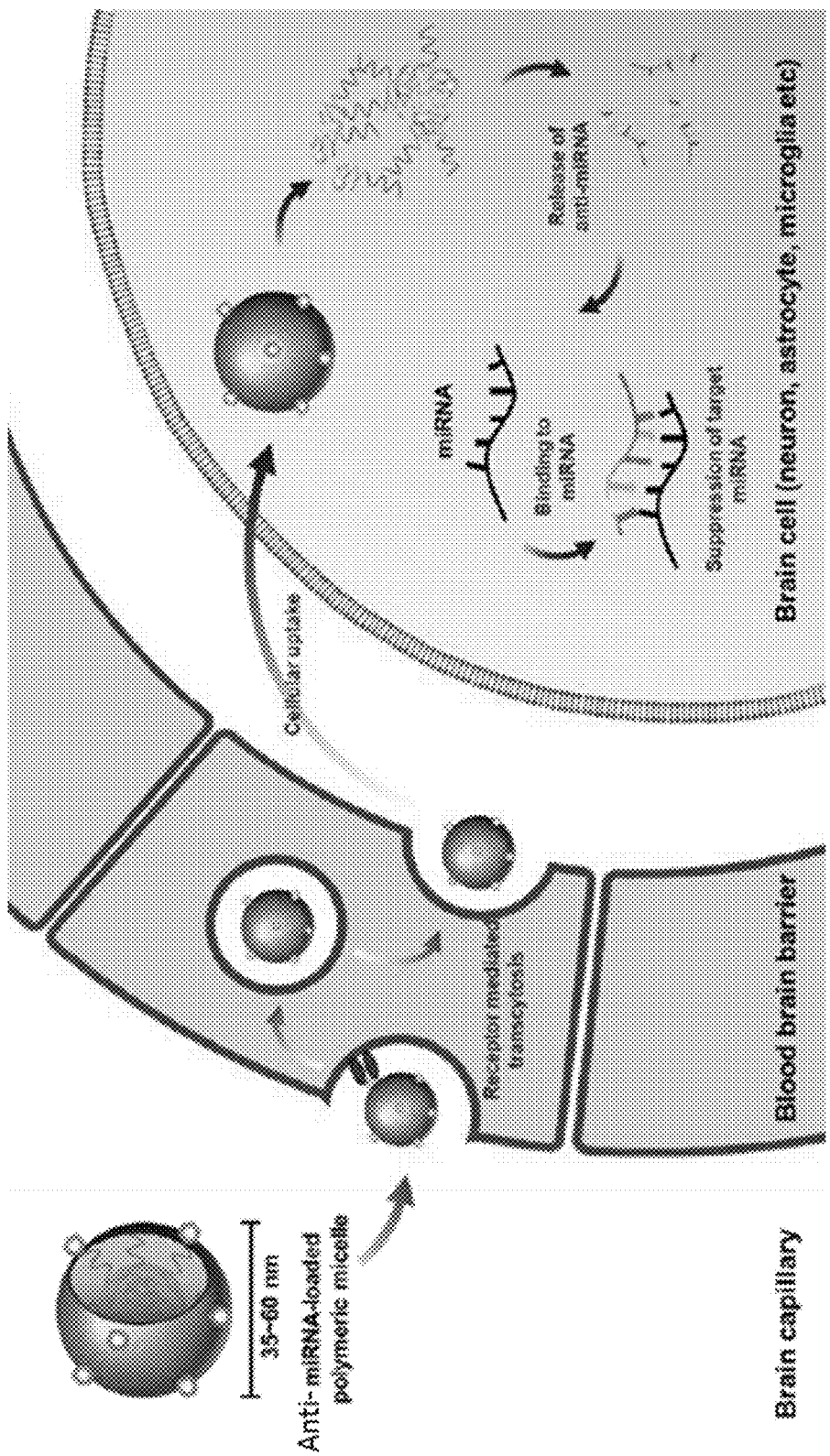
FIG. 7 shows a schematic representation of the mechanism by which payloads contained in micelles of the present disclosure are delivered to target locations in the central nervous system. The micelles cross the blood brain barrier via receptor mediated transcytosis followed by cellular update by brain cells, e.g., neurons, astrocytes, or microglia. The micelles are disassembled in the cytoplasm leading to the release of the payload, e.g., an anti-miRNA, which upon binding to a target mRNA suppress or downregulate the expression of the protein encoded by the target mRNA.

In some aspects, the present disclosure provides methods of crossing blood brain barrier (BBB) comprising administering the micelles disclosed herein, e.g., micelles comprising tryptophan and/or tyrosine as a targeting moiety. As exemplified in FIG. 7, a micelle of the present disclosure loaded with anti-miRNA can be targeted to a BBB receptor, e.g., LAT1, as disclosed above. Once the micelle is translocated across the BBB via receptor mediate transcytosis and undergoes cellular uptake by brain cells (e.g., neurons, astrocytes or microglia), the payload (e.g., an antimir) would be released and interact with an intracellular target (e.g., the antimir can bind to a target microRNA and trigger RNAse H mediated degradation).

In some aspects, encapsulation of the payload in a micelle of the present disclosure can increase the resistance of the payload to degradation at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% compared to the free payload (i.e., not in a micelle, e.g., free in solution).

In some aspects, encapsulation of the payload in a micelle of the present disclosure can increase the resistance of the payload to degradation at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, or at least about 30-fold compared to the free payload.

The present disclosure also provides methods to increase the stability of a payload during administration (e.g., while in the subject's bloodstream) comprising incorporating the payload, e.g., an anionic payload such as a nucleic acid (e.g., an antimir) into a micelle of the present disclosure.

In some aspects, encapsulation of the payload in a micelle of the present disclosure can increase the stability (e.g., increase the resistance to nucleases) of the payload at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% compared to the free payload.

In some aspects, encapsulation of the payload in a micelle of the present disclosure can increase the stability (e.g., increase the resistance to nucleases) of the payload at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, or at least about 30-fold compared to the free payload.

The present disclosure also provides methods to increase a payload's plasma half-life comprising incorporating the payload, e.g., an anionic payload such as a nucleic acid (e.g., an antimir) into a micelle of the present disclosure.

In some aspects, encapsulation of the payload in a micelle of the present disclosure can increase the plasma half-life of the payload at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, at least about 1900%, or at least about 2000%, compared to the free payload.

In some aspects, encapsulation of the payload in a micelle of the present disclosure can increase the plasma half-life of the payload at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, or at least about 30-fold compared to the free payload.

In some aspects, the encapsulated payload is an antimir disclosed herein, e.g., an antisense oligonucleotide of SEQ ID NO: 18, or a variant or derivative thereof (e.g., an oligonucleotide having at least about 70% identity to the antisense oligonucleotide of SEQ ID NO: 18) wherein the encapsulation of the antimir in a micelle of the present disclosure increases the plasma half-life of the antimir at least about 10-fold, at least about 12-fold, at least about 14-fold, at least about 16-fold, at least about 18-fold, or at least about 20-fold compared to the plasma half-life of the free antimir. In one particular aspect, the encapsulated payload is an antimir disclosed herein, e.g., an antisense oligonucleotide of SEQ ID NO: 18, or a variant or derivative thereof (e.g., an oligonucleotide having at least about 70% identity to the antisense oligonucleotide of SEQ ID NO: 18) wherein the encapsulation of the antimir in a micelle of the present disclosure increases the plasma half-life of the antimir at least about 20-fold compared to the plasma half-life of the free antimir. In some aspects, the plasma half-life of the antimir encapsulated in a micelle of the present disclosure is at least about 30 minutes, at least about 40 minutes, at least about 50 minutes, at least about 60 minutes, at least about 70 minutes, at least about 80 minutes, at least about 90 minutes, at least about 100 minutes, or at least about 120 minutes. In one particular aspects, the plasma half-life of the antimir (e.g., an antisense oligonucleotide of SEQ ID NO: 18) encapsulated in a micelle of the present disclosure is at least about 90 minutes.

The present disclosure also provides methods to increase the permeation, delivery, transit, or transport of a payload through a physiological barrier, e.g., the BBB or the plasma membrane, comprising incorporating the payload, e.g., an anionic payload such as a nucleic acid (e.g., an antimir) into a micelle of the present disclosure.

In some aspects, encapsulation of a payload in a micelle of the present disclosure can increase the permeation, delivery, transit, or transport of the payload through a physiological barrier, e.g., the BBB or the plasma membrane, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% compared to the free payload.

In some aspects, encapsulation of a payload in a micelle of the present disclosure can increase the permeation, delivery, transit, or transport of the payload through a physiological barrier, e.g., the BBB or the plasma membrane, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, or at least about 30-fold compared to the free payload.

In some aspects, the micelles of the present disclosure can be used to target stem cells, e.g., to deliver therapeutic molecules (e.g., therapeutic polynucleotides) or gene therapy components. In other aspects, the micelles of the present disclosure can be used to treat cancer. For example, micelles of the present disclosure can target a marker specific for a certain type of cancer, e.g., a glioma, breast cancer, pancreatic cancer, liver cancer, skin cancer, or cervical cancer, and carry as payload a therapeutic molecule (e.g., a therapeutic polynucleotide, a peptide, or a small molecule).

In specific aspects, the micelles of the present disclosure can be used to treat pancreatic cancer. In some aspects, the targeting moiety directing the micelles of the present disclosure to pancreatic tissues is a cyclic RGD peptide. In other aspects, the targeting moiety directing the micelles of the present disclosure to pancreatic tissues is a biomarker predominantly or exclusively expressed on the surface of normal or cancerous pancreatic cells. In some aspects, the payload of the micelle of the present disclosure is an oligonucleotide targeting K-Ras, wherein the delivery of the payload to pancreatic tissue effectively reduces the expression of K-Ras.

Figure 24:
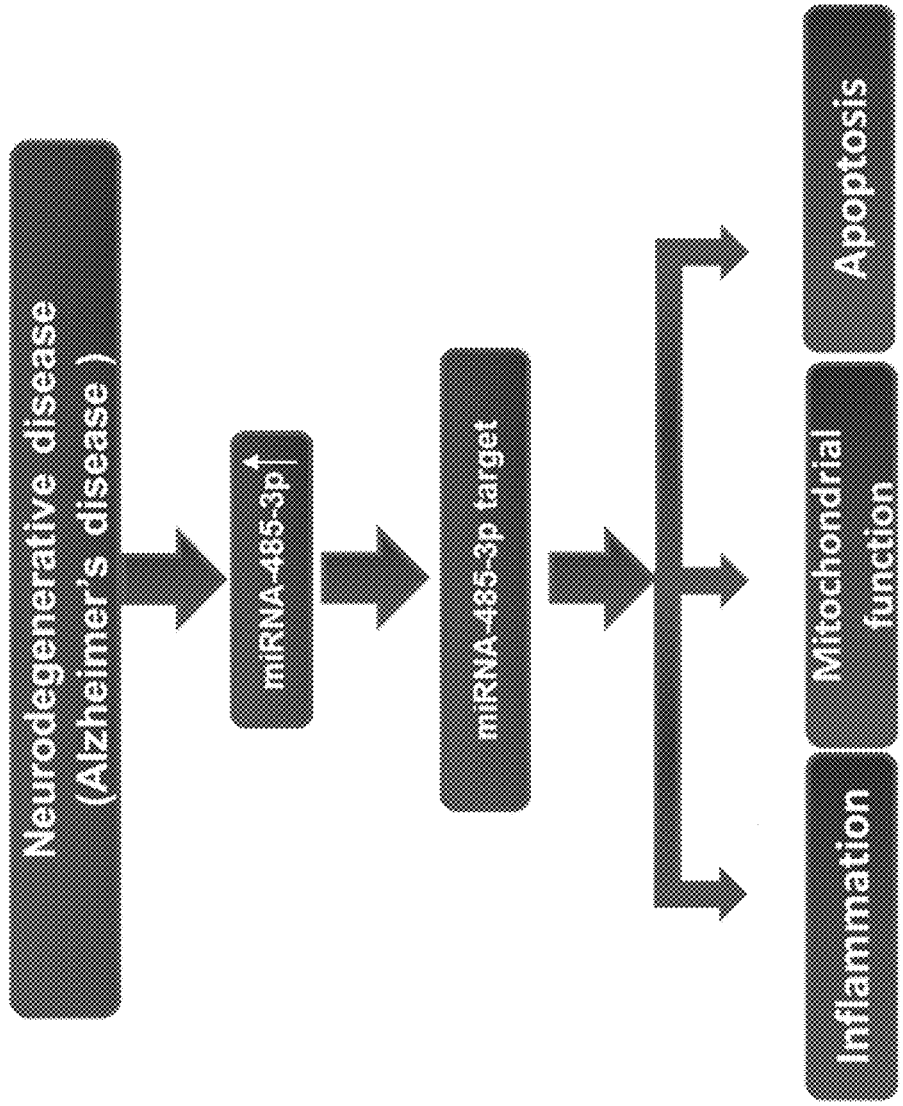
FIG. 24 shows the role of miRNA 485-3p in Alzheimer's disease.

In some aspects, the micelles of the present disclosure can be used to treat or ameliorate the symptoms of a neurodegenerative disease, e.g., Alzheimer's disease. In some aspects, the micelles of the present disclosure comprise a payload, e.g., an antimir, targeting a molecule overexpressed in Alzheimer's disease neuronal tissue, e.g., miRNA-485-3p. Accordingly, in some aspects, the administration of a micelle of the present disclosure (e.g., a micelle comprising a LAT1 targeting moiety to effectively transport the micelle across the BBB and an antimir payload targeting miRNA-485-3p) to an Alzheimer's disease patient can prevent or ameliorate symptoms of Alzheimer's disease such as apoptosis, loss of mitochondrial function, or inflammation. See FIG. 24.

In some aspects, the present disclosure provides a method to reduce inflammation, e.g., neuroinflammation, in a subject suffering from a neurodegenerative disease (e.g., Alzheimer's disease) comprising administering to the subject a therapeutically effective amount of a micelle of the present disclosure, wherein the micelle comprises an therapeutic agent capable of effectively reducing inflammation, e.g., neuroinflammation, in the subject. In some aspects, the neuroinflammation is cortex inflammation. In some aspects, the neuroinflammation is hippocampus inflammation. In some aspects, the therapeutic agent is an antimir targeting miRNA-485-3p (e.g., an antimir of SEQ ID NO:18 or fragment or variant thereof) wherein the antimir can reduce the levels of miRNA-485-3p in the subject.

In some aspects, the administration of a micelle of the present disclosure to a subject suffering from a neurodegenerative disease (e.g., Alzheimer's disease) can decrease the level of neuroinflammation by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the neuroinflammation compared to the level of neuroinflammation observed in a subject or a population of subjects not treated with a micelle of the present disclosure.

In some aspects, the present disclosure provides a method to reduce amyloid plaque burden in a subject suffering from Alzheimer's disease comprising administering to the subject a therapeutically effective amount of a micelle of the present disclosure, wherein the micelle comprises an therapeutic agent capable of effectively reducing amyloid plaque burden in the subject. In some aspects, the therapeutic agent is an antimir targeting miRNA-485-3p (e.g., an antimir of SEQ ID NO:18 or fragment or variant thereof) wherein the antimir can reduce the levels of miRNA-485-3p in the subject.

In some aspects, the administration of a micelle of the present disclosure to a subject suffering from a neurodegenerative disease (e.g., Alzheimer's disease) can decrease at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the amyloid plaque burden in the subject compared to the amyloid plaque burden observed in a subject or a population of subjects not treated with a micelle of the present disclosure.

In some aspects, the present disclosure provides a method to recover and/or induce neurogenesis in a subject suffering from a neurodegenerative disease (e.g., Alzheimer's disease) comprising administering to the subject a therapeutically effective amount of a micelle of the present disclosure, wherein the micelle comprises an therapeutic agent capable of effectively recovering and/or inducing neurogenesis in the subject. In some aspects, the therapeutic agent is an antimir targeting miRNA-485-3p (e.g., an antimir of SEQ ID NO:18 or fragment or variant thereof) wherein the antimir can reduce the levels of miRNA-485-3p in the subject.

In some aspects, the administration of a micelle of the present disclosure to a subject suffering from a neurodegenerative disease (e.g., Alzheimer's disease) can recover and/or induce neurogenesis in the subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the level of neurogenesis observed in a subject or a population of subjects not treated with a micelle of the present disclosure.

In some aspects, the present disclosure provides a method to improve cognitive function in a subject suffering from a neurodegenerative disease (e.g., Alzheimer's disease) comprising administering to the subject a therapeutically effective amount of a micelle of the present disclosure, wherein the micelle comprises an therapeutic agent capable of effectively improving cognitive function in the subject. In some aspects, the therapeutic agent is an antimir targeting miRNA-485-3p (e.g., an antimir of SEQ ID NO:18 or fragment or variant thereof) wherein the antimir can reduce the levels of miRNA-485-3p in the subject.

In some aspects, the administration of a micelle of the present disclosure to a subject suffering from a neurodegenerative disease (e.g., Alzheimer's disease) can increase the cognitive function of the subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the cognitive function observed in a subject or a population of subjects not treated with a micelle of the present disclosure.

VIII. Kits

The present disclosure also provides kits, or products of manufacture, comprising a cationic carrier unit, a micelle, or a pharmaceutical composition of the present disclosure and optionally instructions for use. In some aspects, the kit or product of manufacture comprises a cationic carrier unit, a micelle, or a pharmaceutical composition of the present disclosure in one or more containers. In some aspects, the kit or product of manufacture comprises a cationic carrier unit, a micelle, or a pharmaceutical composition of the present disclosure and a brochure. In some aspects, the kit or product of manufacture comprises a cationic carrier unit, a micelle, or a pharmaceutical composition of the present disclosure and instructions for use. One skilled in the art will readily recognize that a cationic carrier unit, a micelle, or a pharmaceutical composition of the present disclosure, or combinations thereof, can be readily incorporated into one of the established kit formats which are well known in the art.

In some aspects, the kit or product of manufacture comprises a cationic carrier unit of the present disclosure in dry form in a container (e.g., a glass vial), and optionally a vial with a solvent suitable to hydrate the dry the cationic carrier unit, and optionally instructions for the hydration of the cationic carrier unit and the formation of micelles. In some aspects, the kit or product of manufacture further comprises at least one additional container (e.g., a glass vial) with the micelle's anionic payload (e.g., an antisense oligonucleotide). In some aspects, the kit or product of manufacture comprises a cationic carrier unit of the present disclosure in a dry form and the micelle's anionic payload also in dry form in the same container, or in different containers. In some aspects, the kit or product of manufacture comprises a cationic carrier unit of the present disclosure in solution and the micelle's anionic payload also in solution in the same container, or in different containers. In some aspects, the kit or product of manufacture comprises a micelle of the present disclosure in solution, and instructions for use. In some aspects, the kit or product of manufacture comprises a micelle of the present disclosure in dry form, and instructions for use (e.g., instructions for reconstitution and administration).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooke, Antisense drug Technology: Principles, Strategies and Applications, 2nd Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1

(a) Synthesis of alkyne modified tyrosine: An alkyne modified tyrosine was generated as an intermediate for the synthesis of a tissue specific targeting moiety (TM, see FIG. 3) of a cationic carrier unit to direct micelles of the present disclosure to the LAT1 transporter in the BBB.

A mixture of N-(tert-butoxycarbonyl)-L-tyrosine methyl ester (Boc-Tyr-OMe) (0.5 g, 1.69 mmol) and $K_2CO_3$ (1.5 equiv., 2.54 mmol) in acetonitrile (4.0 ml) was added drop by drop to propargyl bromide (1.2 equiv., 2.03 mmol). The reaction mixture was heated at 60° C. overnight. After the reaction, the reaction mixture was extracted using water: ethyl acetate (EA). Then, the organic layer was washed using a brine solution. The crude material was purified by flash column (EA in hexane 10%). Next, the resulting product was dissolved in 1,4-dioxane (1.0 ml) and 6.0 M HCl (1.0 ml). The reaction mixture was heated at 100° C. overnight. Next, the dioxane was removed and extracted by EA. Aqueous NaOH (0.5 M) solution was added to the mixture until the pH value become 7. The reactant was concentrated by evaporator and centrifuged at 12,000 rpm at 0° C. The precipitate was washed with deionized water and lyophilized.

(b) Synthesis of poly(ethylene glycol)-b-poly(L-lysine) (PEG-PLL): This synthesis step generated the water-soluble biopolymer (WP) and cationic carrier (CC) of a cationic carrier unit of the present disclosure (see FIG. 3).

Poly(ethylene glycol)-b-poly(L-lysine) was synthesized by ring opening polymerization of Lys(TFA)-NCA with monomethoxy PEG (MeO-PEG) as a macroinitiator. In brief, MeO-PEG (600 mg, 0.12 mmol) and Lys(TFA)-NCA (2574 mg, 9.6 mmol) were separately dissolved in DMF containing 1M thiourea and DMF (or NMP). Lys(TFA)-NCA solution was dropped into the MeO-PEG solution by micro syringe and the reaction mixture was stirred at 37° C. for 4 days. The reaction bottles were purged with argon and vacuum. All reactions were conducted in argon atmosphere. After the reaction, the mixture was precipitated into an excess amount of diethyl ether. The precipitate was re-dissolved in methanol and precipitated again into cold diethyl ether. Then it was filtered and white powder was obtained after drying in vacuo. For the deprotection of TFA group in PEG-PLL(TFA), the next step was followed.

MeO-PEG-PLL(TFA) (500 mg) was dissolved in methanol (60 mL) and 1N NaOH (6 mL) was dropped into the polymer solution with stirring. The mixture was maintained for 1 day with stirring at 37° C. The reaction mixture was dialyzed against 10 mM HEPES for 4 times and distilled water. White powder of PEG-PLL was obtained after lyophilization.

(b) Synthesis of azido-poly(ethylene glycol)-b-poly(L-lysine) ($N_3$—PEG-PLL): This synthesis step generated the water-soluble biopolymer (WP) and cationic carrier (CC) of a cationic carrier unit of the present disclosure (see FIG. 3).

Azido-poly(ethylene glycol)-b-poly(L-lysine) was synthesized by ring opening polymerization of Lys(TFA)-NCA with azido-PEG ($N_3$-PEG). In brief, $N_3$-PEG (300 mg, 0.06 mmol) and Lys(TFA)-NCA (1287 mg, 4.8 mmol) were separately dissolved in DMF containing 1M thiourea and DMF (or NMP). Lys(TFA)-NCA solution was dropped into the $N_3$-PEG solution by micro syringe and the reaction mixture was stirred at 37° C. for 4 days. The reaction bottles were purged with argon and vacuum. All reactions were conducted in argon atmosphere. After the reaction, the mixture was precipitated into an excess amount of diethyl ether. The precipitate was re-dissolved in methanol and precipitated again into cold diethyl ether. Then it was filtered and white powder was obtained after drying in vacuo. For the deprotection of TFA group in PEG-PLL(TFA), the next step was followed.

$N_3$-PEG-PLL (500 mg) was dissolved in methanol (60 mL) and 1N NaOH (6 mL) was dropped into the polymer solution with stirring. The mixture was maintained for 1 day with stirring at 37° C. The reaction mixture was dialyzed against 10 mM HEPES for 4 times and distilled water. White powder of $N_3$-PEG-PLL was obtained after lyophilization.

(c) Synthesis of (methoxy or) azido-poly(ethylene glycol)-b-poly(L-lysine/nicotinamide/mercaptopropanamide) ($N_3$—PEG-PLL(Nic/SH)): In this step, the tissue-specific adjuvant moieties (AM, see FIG. 3) were attached to the WP-CC component of a cationic carrier unit of the present disclosure. The tissue-specific adjuvant moiety (AM) used in the cationic carrier unit was nicotinamide (vitamin B3). This step would yield the WP-CC-AM components of the cationic carrier unit depicted in FIG. 3.

Azido-poly(ethylene glycol)-b-poly(L-lysine/nicotinamide/mercaptopropanamide) ($N_3$—PEG-PLL(Nic/SH)) was synthesized by chemical modification of $N_3$-PEG-PLL and nicotinic acid in the presence of EDC/NHS. $N_3$-PEG-PLL (372 mg, 25.8 µmol) and nicotinic acid (556.7 mg, 1.02 equiv. to $NH_2$ of PEG-PLL) were separately dissolved in mixture of deionized water and methanol (1:1). EDC.HCl (556.7 mg, 1.5 equiv. to $NH_2$ of $N_3$-PEG-PLL) was added into nicotinic acid solution and NHS (334.2 mg, 1.5 equiv. to $NH_2$ of PEG-PLL) stepwise added into the mixture.

The reaction mixture was added into the $N_3$-PEG-PLL solution. The reaction mixture was maintained at 37° C. for 16 hours with stirring. After 16 hours, 3,3'-dithiodiproponic acid (36.8 mg, 0.1 equiv.) was dissolved in methanol, EDC.HCl (40.3 mg, 0.15 equiv.), and NHS (24.2 mg, 0.15 equiv.) were dissolved each in deionized water. Then, NHS and EDC.HCl were added sequentially into 3,3'-dithiodiproponic acid solution. The mixture solution was stirred for 4 hours at 37° C. after adding crude $N_3$-PEG-PLL(Nic) solution.

For purification, the mixture was dialyzed against methanol for 2 hours, added DL-dithiothreitol (DTT, 40.6 mg, 0.15 equiv.), then activated for 30 min.

For removing the DTT, the mixture was dialyzed sequentially methanol, 50% methanol in deionized water, deionized water (d) Synthesis of Phenyl alanine-poly(ethylene glycol)-b-poly(L-lysine/nicotinamide/mercaptopropanamide) (Phe-PEG-PLL(Nic/SH)): In this step, the tissue-specific targeting moiety (TM) was attached to the WP-CC-AM component synthesized in the previous step. The TM component (phenyl alanine) was generated by reaction of the intermediate generated in step (a) with the product of step (c).

To target brain endothelial tissue in blood vessels, as a LAT1 targeting amino acid, phenyl alanine was introduced by click reaction between $N_3$-PEG-PLL(Nic/SH) and alkyne modified tyrosine in the presence of copper catalyst In brief, $N_3$-PEG-PLL(Nic/SH) (130 mg, 6.5 µmol) and alkyne modified phenyl alanine (5.7 mg, 4.0 equiv.) were dissolved in deionized water (or 50 mM sodium phosphate buffer). Then, $CuSO_4 \cdot H_2O$ (0.4 mg, 25 mol %) and Tris(3-hydroxypropyltriazolylmethyl)amine (THPTA, 3.4 mg, 1.2 equiv.) were dissolved deionized water and added $N_3$-PEG-PLL(Nic/SH) solution. Then, sodium ascorbate (3.2 mg, 2.5 equiv.) were added into the mixture solution. The reaction mixture was maintained with stirring for 16 hours at room temperature. After the reaction, the mixture was transferred into dialysis membranes (MWCO=7,000) and dialyzed against deionized water for 1 day. The final product was obtained after lyophilization. FIG. 4 shows the $^1$H-NMR characterization of the carrier unit.

Example 2

Polyion Complex (PIC) Micelle Preparation

Once the cationic carrier units of the present disclosure were generated as described in Example 1, micelles were produced. The micelles described in the present example comprised cationic carrier units combined with an antisense oligonucleotide payload.

Nano sized PIC micelles were prepared by mixing MeO- or Phe-PEG-PLL(Nic) and miRNA. PEG-PLL(Nic) was dissolved in HEPES buffer (10 mM) at 0.5 mg/mL concentration. Then a miRNA solution (22.5 µM) in RNAse free water was mixed with the polymer solution at 2:1 (v/v) ratio of miRNA to polymer.

The mixing ratio of polymer to anti-miRNA was determined by optimizing micelle forming conditions, i.e., ratio between amine in polymer (carrier of the present disclosure) to phosphate in anti-miRNA (payload). The mixture of polymer (carrier) and anti-miRNA (payload) was vigorously mixed for 90 seconds by multi-vortex at 3000 rpm, and kept at room temperature for 30 min to stabilize the micelles.

Particle size distribution and scattering light intensity (SLI) were measured by Zeta-sizer with 634 nm wavelength. FIG. 9 shows particle size distribution of miRNA-loaded polyion complex micelles in PBS. Anti-miRNA loaded micelles shows <60 nm particle size with low PDI distribution which indicates the complex is a homogeneous particle. The peak of the distribution, as shown in FIG. 9, was at 32 nm.

Micelles (10 µM of Anti-miRNA concentration) were stored at 4° C. prior to use. MeO- or Phe-micelles were prepared using the same method, and different amounts of Phe-containing micelles (25%~75%) were also prepared by mixing both polymers during micelle preparation.

Example 3

Targeting Brain Using LAT1 and Phenylalanine

Figure 10:
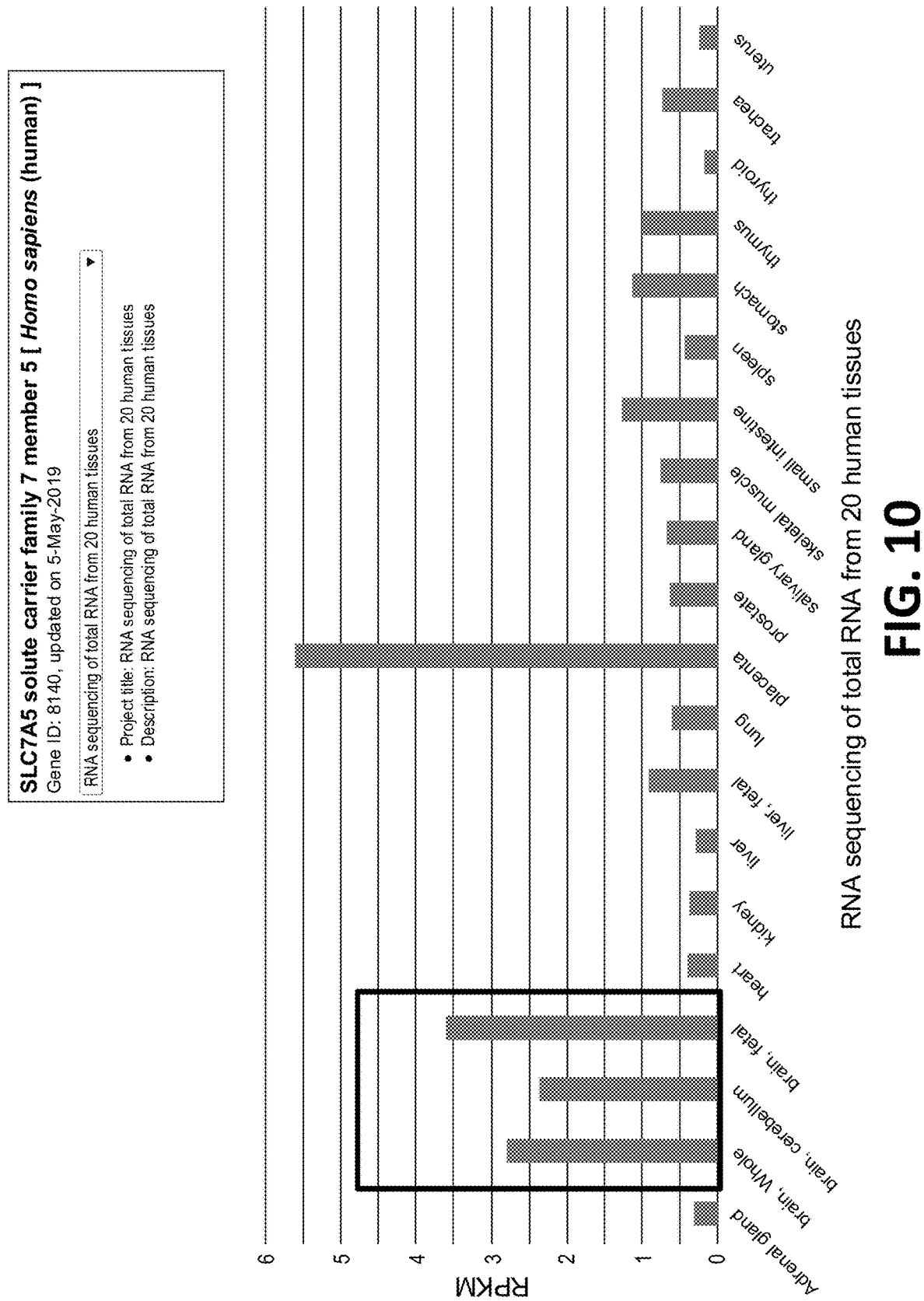
FIG. 10 shows the distribution of LAT1(SLC7A5) solute carrier family 7 member 5 [*Homo sapiens* (human)] in different tissue. The data was obtained from NCBI and corresponds to RNA sequencing of total RNA from 20 human tissues.
Figure 11:
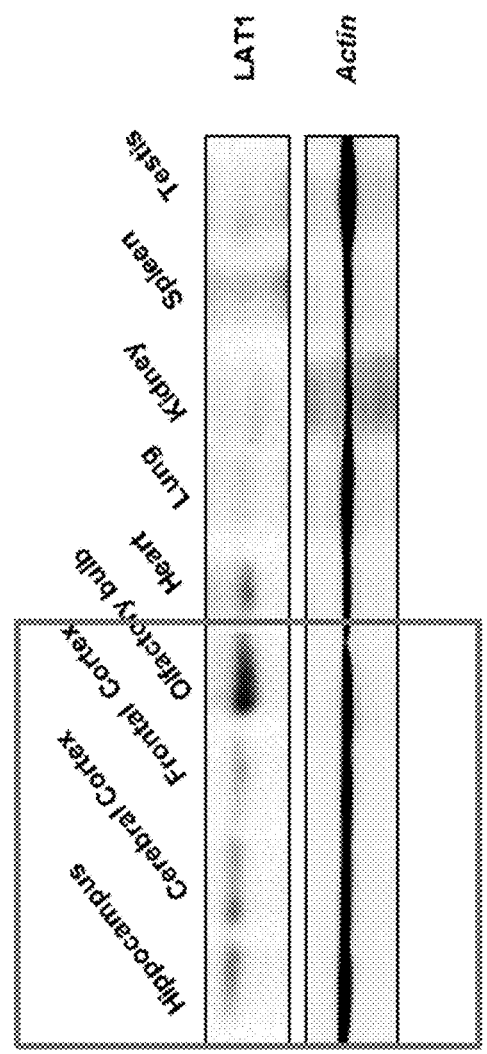
FIG. 11 shows LAT1 expression levels in vivo in different mouse tissues.

LAT1 was selected as the target molecule to drive the micelles of the present disclosure across the BBB. As shown in FIG. 10, in humans, LAT1 was preferentially expressed in brain. FIG. 11 shows that in mice LAT1 was also expressed preferentially in brain tissue.

To investigate the possibility of crossing the blood brain barrier using a LAT1 protein, Cy 5.5 dye or Cy 5.5 labeled phenylalanine was intracerebroventricularly administrated to mice (n=3) and the fluorescence intensities of brain lysate were analyzed after 1 hour of injection. For measurement, Cy 5.5 was labeled by click reaction with alkyne modified tyrosine and $N_3$-Cy 5.5.

Cy 5.5 labeled phenylalanine or $N_3$-Cy 5.5 (20 μg of Cy5.5 Conc.) was separately administrated via intracerebroventricular injection and the same volume of PBS was also injected as a control. One hour post injection, all mice (n=3) were sacrificed and remaining blood was washed with 5 mL PBS for perfusion. The mice brains were extracted and homogenized with lysis buffer using a probe-type sonicator. The lysate samples were transferred into the 96-well plates and fluorescence intensities were measured by multi-plate reader with Ex/Em=650/690.

Figure 12:
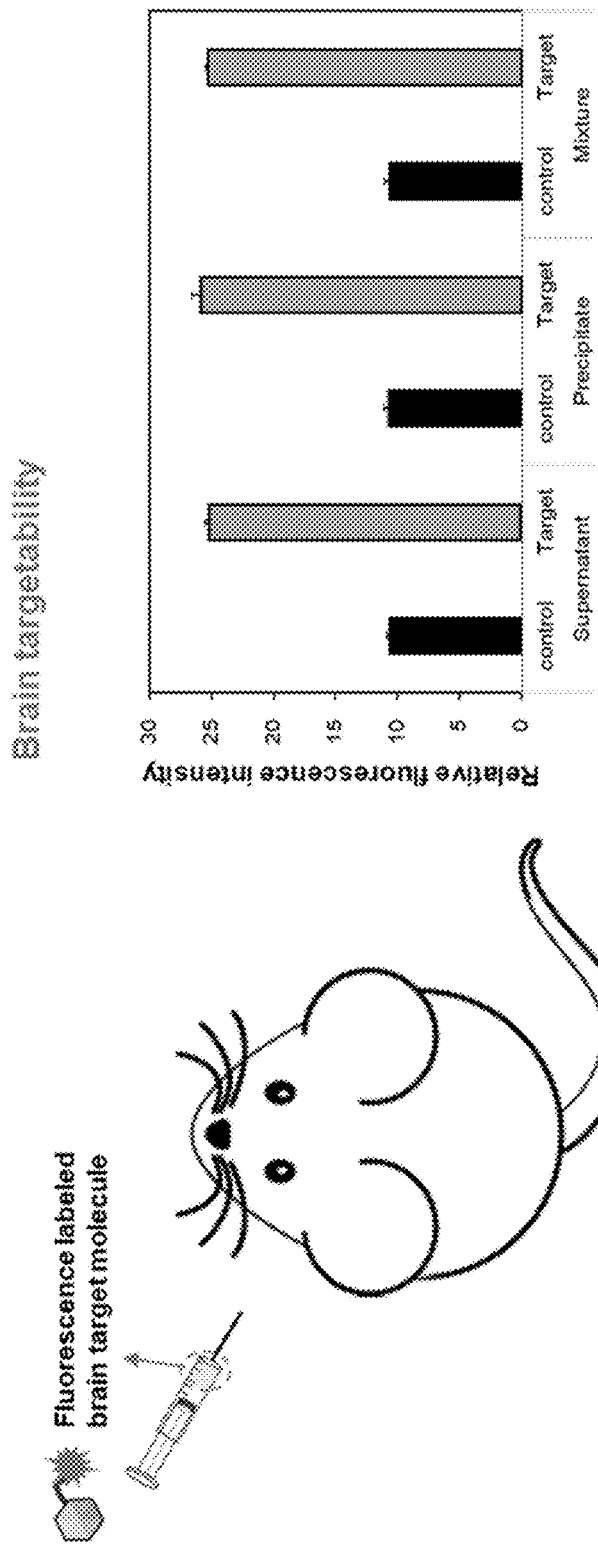
FIG. 12 shows LAT1 targeting using a brain targeting carrier unit of the present disclosure. The fluorescence (Cy5.5) labeled brain targeting carrier unit binds to LAT1, which is expressed in brain parenchyma, and shows higher accumulation than a non-targeted Cy5.5 molecule.

The fluorescence (Cy5.5) labeled carrier unit targeted to brain indeed was able to bind to LAT1, which was expressed in brain parenchyma, and showed higher accumulation levels than a non-targeted Cy5.5 molecule. See FIG. 12.

Anti-miRNA loaded polyion complex micelle (i.e., micelles of the present disclosure) which were targeted to LAT1 were able to cross the BBB and were significantly accumulated in the brain compared to non-targeted micelles.

Example 4

In Vivo Stability of Micelles of the Disclosure

In vivo stability of the micelles disclosed herein was evaluated by measuring the blood circulation behavior after systemic injection of the micelle. Cy 5.5 labeled miRNA loaded micelles and naked Cy 5.5 labeled miRNA (20 μg of miRNA Conc.) were systemically injected into the mice, and 120 μL of blood was sampled from the tail vein at desired times. The blood samples were centrifuged at 2,500 rpm, and supernatant plasma samples were transferred into 96-well plate. The remaining fluorescence intensities of plasma were analyzed by multi-plate reader with Ex/Em=650/690.

Figure 8:
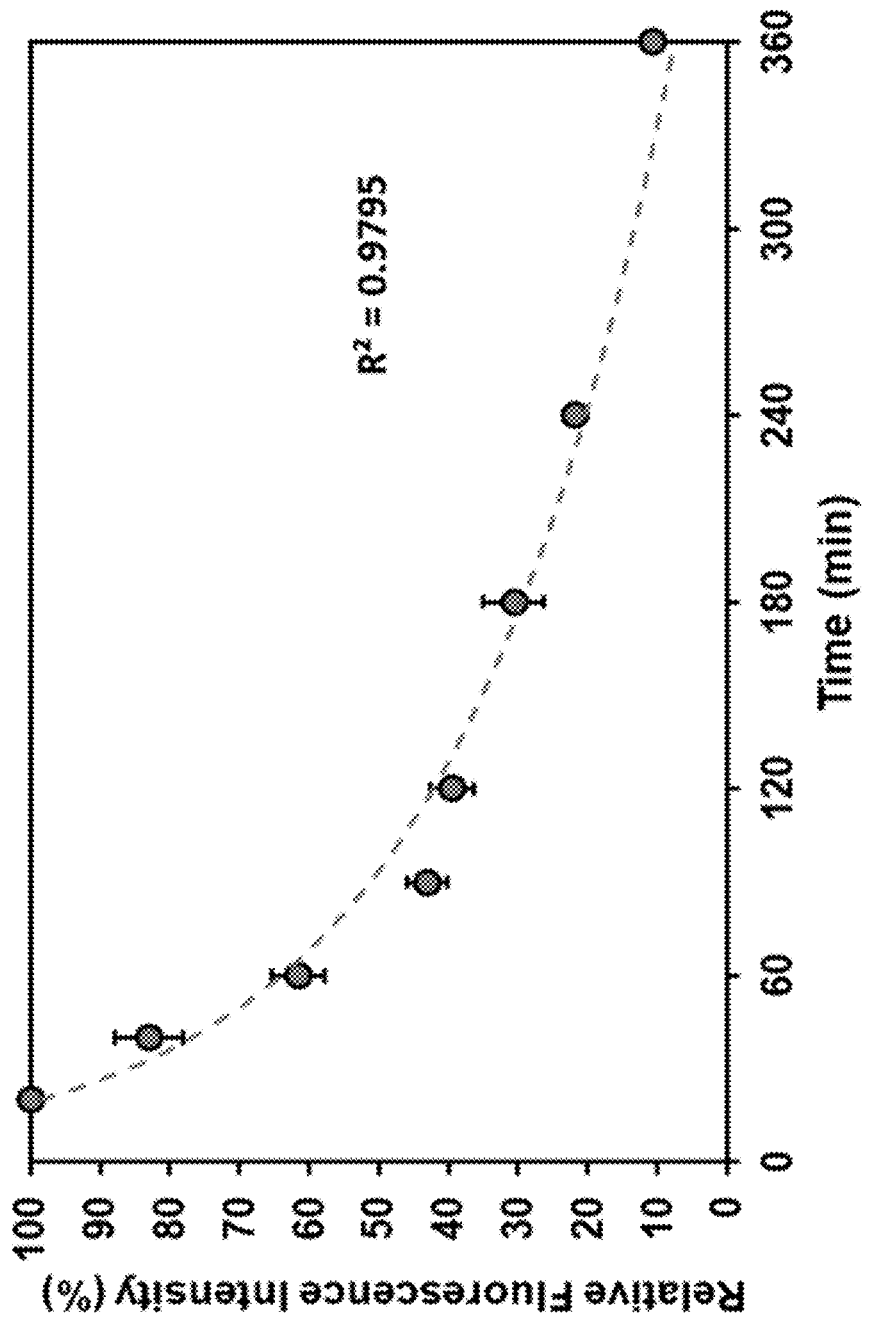
FIG. 8 shows the increase in stability (increase in blood plasma half-life) due to encapsulation of the payload in a micelle of the present disclosure. Without the micelles, an anti-microRNA (antimir) has a blood plasma half-life of less than 5 minutes. After incorporation to a micelle of the present disclosure, the blood plasma half-life of the antimir increases to 80-120 minutes. After encapsulation, the half-life of the antimir disclosed in the examples increased from less than 5 minutes to approximately 93 minutes (i.e., approximately a 20-fold increase in plasma half-life).

Encapsulation of the anti-microRNA payload in a micelle of the present disclosure resulted in an increase in stability. See FIG. 8. Under control conditions, an anti-microRNA (antimir) had a blood plasma half-life of less than 5 minutes. However, after incorporation of the anti-miRNA in a micelle of the present disclosure, the blood plasma half-life increased to 80-120 minutes. The stability of the micelles was not affected by different anti-miRNA loads. Micelles in which the carrier units did not contain antimir was stable as those with 25% or 50% of the carrier units complexed to antimir.

Example 5

Experiments in Alzheimer's Disease Models (i) Materials and Methods (a) Mice: 5×FAD APP transgenic mice (Stock number: 34840-JAX) were purchased from the Jackson Laboratory. TG and age-matched wild type (WT) littermates were used in the studies. All the animals were kept in individually cages in a 12/12-h light/dark cycle with controlled temperature and humidity, and food and water. 5×FAD mice, also known as APP/PS1, Tg6799 or Tg-5×FAD, are animal model systems for Alzheimer's disease. 5×FAD mice express human APP and PSEN1 transgenes with a total of five AD-linked mutations: the Swedish (K670N/M671L), Florida (I716V), and London (V717I) mutations in APP, and the M146L and L286V mutations in PSEN1. Three lines were generated originally: Tg6799, Tg7031, and Tg7092. The Tg6799 line, which expresses the highest levels of mutant APP, is the most studied of the three. These widely used mice recapitulate many AD-related phenotypes and have a relatively early and aggressive presentation.

Amyloid plaques, accompanied by gliosis, are seen in mice as young as two months of age. Amyloid pathology is more severe in females than in males. Neuron loss occurs in multiple brain regions, beginning at about 6 months in the areas with the most pronounced amyloidosis. Mice display a range of cognitive and motor deficits.

3×Tg-AD mice harboring three human transgenes, APP (Swe), PS1(M146V) and tau(P301L), were purchased at the Jackson Laboratory. The 3×Tg-AD mice were generated on a C57BL6/129SvJ hybrid background. Mice were housed 4-5 per cage, kept on 12 hr light/dark cycle, and were given ad libitum access to food and water. Translation of the overexpressed transgenes appears to be restricted to the central nervous system, notably in Alzheimer's disease-relevant areas including the hippocampus and cerebral cortex. The initial characterization of this mouse line indicated a progressive increase in amyloid beta peptide deposition, with intracellular immunoreactivity being detected in some brain regions as early as 3-4 months. Synaptic transmission and long-term potentiation are demonstrably impaired in mice 6 months of age. Between 12-15 months aggregates of conformationally altered and hyperphosphorylated tau are detected in the hippocampus. This mutant mouse exhibits plaque and tangle pathology associated with synaptic dysfunction, traits similar to those observed in Alzheimer's disease patients.

(b) ASO-MDS treatment (IV injection): For Intravenous (IV) injection, miR-485-3p antagomir (antimir) in micelles of the present disclosure (ASO-MDS) or negative controls (miR only and micelle only) were prepared. All the treatments of 8-month 5×FAD mice were achieved through intravenous injection of 1.5 mg/kg ASO-MDS on days 7, 14, 21, and 28. See FIG. 17.

(c) Immunohistochemistry: For immunohistochemistry, brains were removed, postfixed and embedded in paraffin. Coronal sections (10-μm thick) through the infarct were cut using a microtome and mounted on slides. The paraffin was removed, and the sections were washed with PBS-T and blocked in 10% bovine serum albumin for 2 h. Thereafter, the following primary antibodies were applied: Rabbit anti-β-amyloid (1-42) (Cell Signaling Technology, Cat #14974), mouse anti-GFAP (Merck, Cat #MAB360), Rabbit anti-IL-1β (Abcam, Cat #9722), Mouse anti-TNF-α (Santa Cruz, Cat #sc-52746) anti-actin (Santa Cruz, Cat #sc-47778). After the behavioral test, hippocampal regions and cortex regions were dissected from H/I mice, and the brain tissue was homogenized in ice-cold RIPA buffer containing protease inhibitors. Homogenates were centrifuged at 12,000 r.p.m. for 30 min at 4° C., and supernatants were collected. The results were visualized using an enhanced chemiluminescence system, and quantified by densitometric analysis (Image J software, NIH). All experiments were performed independently at least three times.

(d) Behavior tests (Y-maze and Passive avoidance): The Y-maze consisted of three black, opaque, plastic arms (30 cm×8 cm×15 cm) 120° from each other. The 5×FAD mice were placed in the center and were allowed to explore all three arms. The number of arm entries and number of trials (the standard for the number of shift is 10 cm from the center, entries into three separate arms.) were recorded to calculate the percentage of alternation. An entry was defined as all three appendages entering a Y-maze arm. Alternating behavior was defined as the number of triads divided by the number of arm entries minus 2 and multiplied by 100. The passive avoidance chamber was divided into a white (light) and a black (dark) compartment (41 cm×21 cm×30 cm). The light compartment contained a 60W electric lamp. The floor (of the dark) department contained a number of (2-mm) stainless steel rods spaced 5 mm apart. The test was done for 3 days.

In the first day, the mouse was allowed to adapt for 5 minutes in a bright zone. The second day was a training phase consisting of 2 steps. In first step, each mouse was placed in the light zone and moved to the dark zone twice. One hour after the first step, each mouse was placed in the light compartment. The door separating the two compartments was opened 30 seconds later. Once the mouse entered the dark compartment, the door closed and an electrical foot shock (0.3 mA/10 g) was delivered through the grid floor for 3 seconds. If the mouse did not go into the dark zone for more than 5 minutes, it was considered to have learned, and the training was done up to 5 times. Twenty-four hours after the training trial, mice were placed in the light chamber for testing. Latency was defined as the time it took for a mouse to enter the dark chamber after the door separating the two compartments opened. The time taken for the mouse to enter the dark zone and exit to the bright zone was defined as TDC (time spent in the dark compartment).

(e) Data analysis: All data are expressed as the mean±s.d. Post-hoc comparisons (Student-Newman-Keuls test) were performed using Prism 8. Behavior tests were assessed by nonparametric statistical procedures. Three group (Control (miR only and micelle only) versus HI-485-3p) comparisons were analysed by the Mann-Whitney U-tests.

Figure 23A:
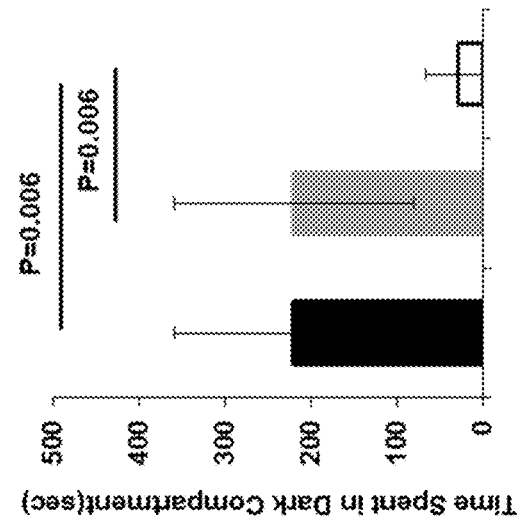
FIG. 23A shows that ASO-MDS delivery improves cognitive function (Y maze) in 5×FAD mice.
Figure 23B:
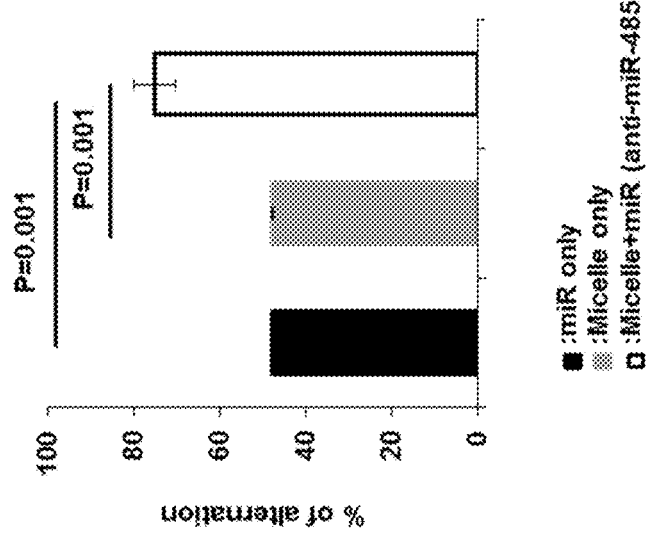
FIG. 23B shows that ASO-MDS delivery improves cognitive function (passive avoidance test) in 5×FAD mice. Y maze and passive avoidance tests for FIG. 23A and FIG. 23B were performed in Mock (miR only and micelle only (left and middle panels, respectively)—and ASO-MDS injected 5×FAD mice (right panel) (n=5 for Mock treated 8-10 months 5×FAD mice, n=7 for BMD001 injected 8-10 months 5×FAD mice).

(ii) Results miRNA-485-3p can be elevated in patients with Alzheimer's disease, leading, e.g., to inflammation, changes in mitochondrial function, and apoptosis. See FIG. 23. Accordingly, micelles of the present disclosure loaded with an antimir targeting miRNA-485-3p were administered to mice models for Alzheimer's disease. These micelles comprising anti-miR-485-3p are referred to as "ASO-MDS" (Anti-Sense Oligonucleotide-Micelle Delivery System) or "micelle+anti-miR-485-3p" in the figures and throughout this application.

Figure 21A:
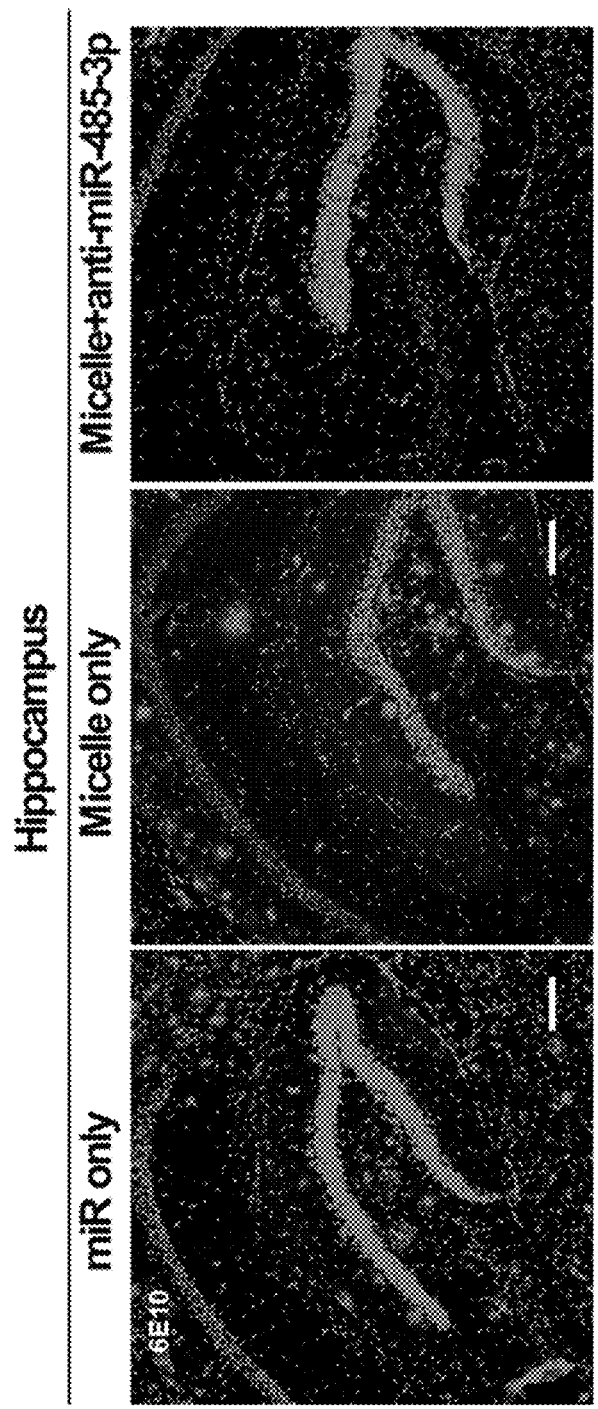
FIG. 21A shows that ASO-MDS delivery decreases amyloid plaque burden in 5×FAD. Immunohistochemical analysis of dentate gyrus in hippocampus after administration of mock (miR only and micelle only (left and middle panels, respectively) or ASO-MDS (right panel). Diffuse plaques in the brain sections were stained by anti-amyloid beta (clone 6E10) and nucleus.
Figure 21B:
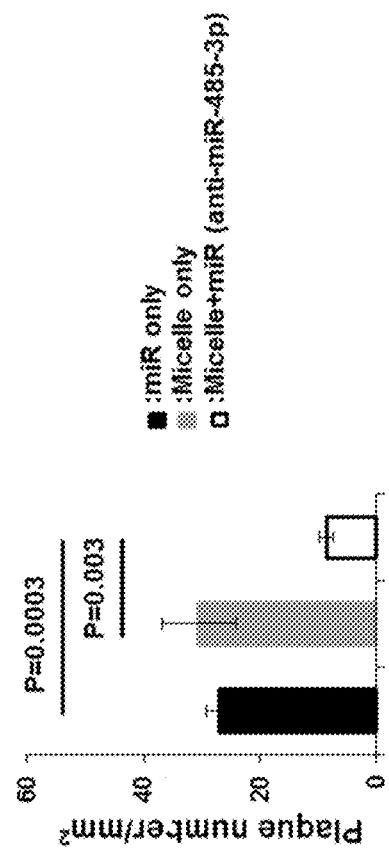
FIG. 21B shows a bar graph of the same data in FIG. 21A. The left bar is miR only, the middle bar is micelle only, and the right bar is micelle+miR.
Figure 22A:
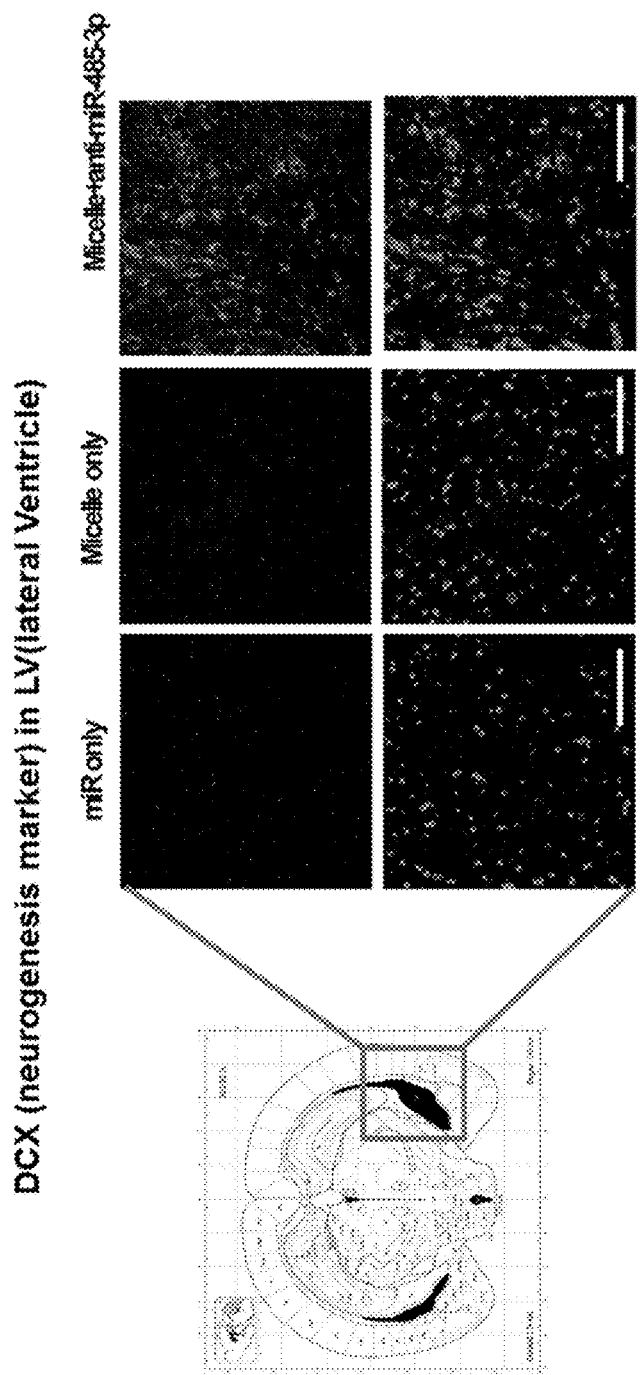
FIG. 22A shows administration of BMD001 recovers neurogenesis in 5×FAD. Immunohistochemical analysis of Lateral Ventricle after administration of mock (miR only and micelle only (left and middle panels, respectively) or ASO-MDS (right panel). Neurogenesis in the brain sections was identified by anti-DCX staining The graph shows the mean number of DCX-stained cells per $mm^2$. The upper panels are stained by anti-DCX staining, i.e., a neurogenesis marker. The lower panels show staining by DAPI (4',6-diamidino-2-phenylindole).
Figure 22B:
FIG. 22B shows a bar graph of the same data shown in FIG. 22A.

After ASO-MDS micelles were injected weekly for 4 weeks in 8 month old 5×FAD transgenic mice, it was observed that neuroinflammation had been reduced in the cortex and hippocampus of the 5×FAD mice after the injection. See FIGS. 19A, 19B, 20A, and 20B. Furthermore, administration of ASO-MDS micelles caused a decrease in amyloid plaque burden. FIGS. 21A and 21B. Treatment with ASO-MDS also led to a recovery in neurogenesis. See FIGS. 22A and 22B. In addition to the improvements in inflammation, amyloid plaque burden, and neurogenesis, treatment with ASO-MDS also improved cognitive function, as shown by the Ymaze and passive avoidance tests. See FIGS. 23A and 23B.

ASO-MDS showed significantly higher % of alteration, i.e., about 80% of alteration while the negative controls showed about 50% in the Ymaze test. See FIG. 23A. ASO-MDS also showed significantly lower time spent in dark compartment (sec) compared to the negative controls.

Example 6

K-Ras Silencing in Pancreatic Cancer

Figure 25:
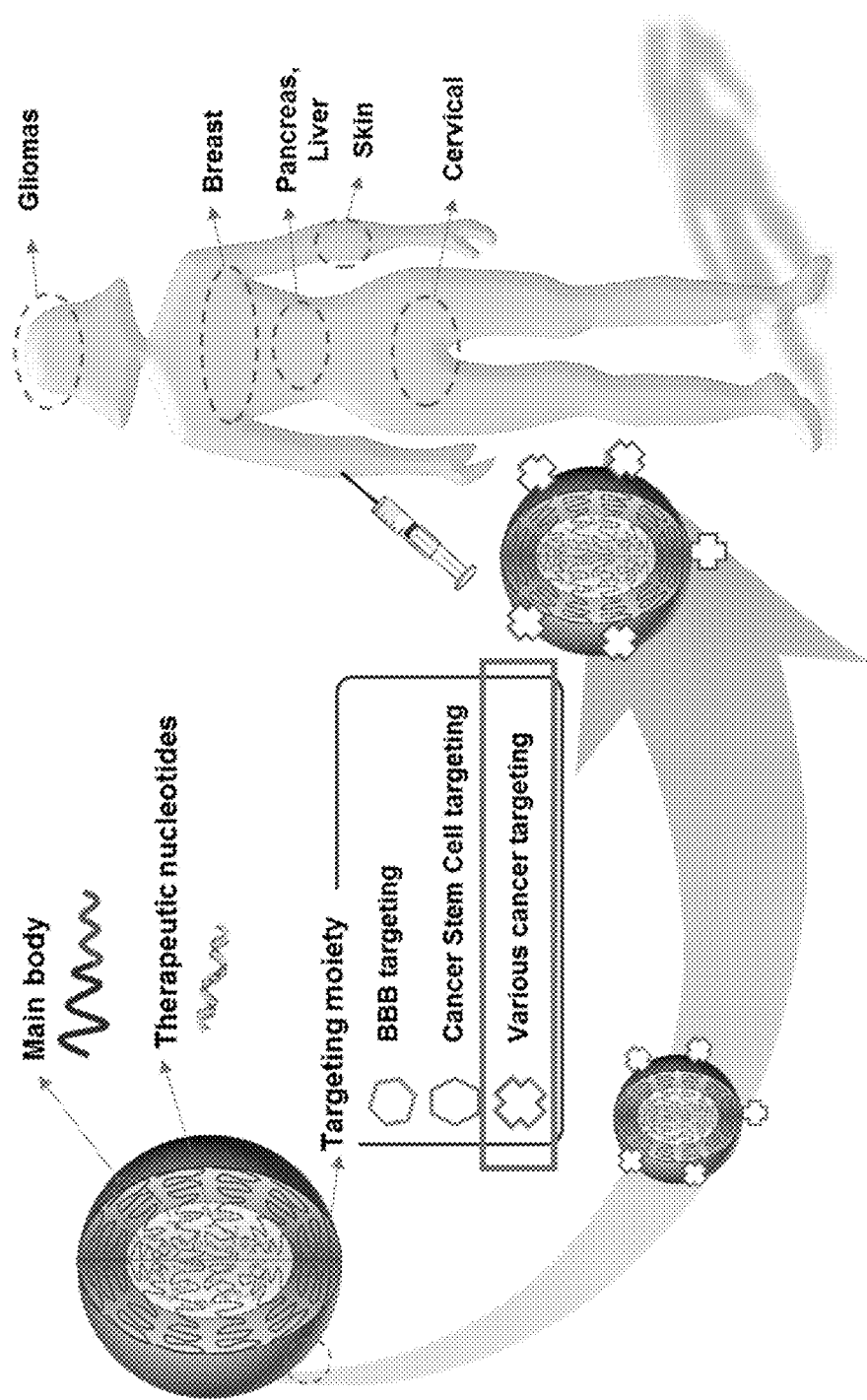
FIG. 25 shows a schematic illustration of cancer targeting application of the micellar delivery system of the present disclosure. The micellar system disclosed herein is a versatile delivery system for cancer treatment as well as brain disease. Various cancer targeting ligands can be applied to this carrier system for delivery of therapeutic agents, e.g., polynucleotides, to cancer cells.

To determine whether the micelles of the present disclosure can be used to effectively deliver anticancer therapies (see FIG. 25), micelles of the present disclosure were targeted to human pancreatic cells using (i) conventional cRGD tumor targeting with a peptide ligand, or (ii) an alternative targeting strategy (X-target). The payload of the micelles was an antisense oligonucleotide targeting K-Ras.

Figure 26A:
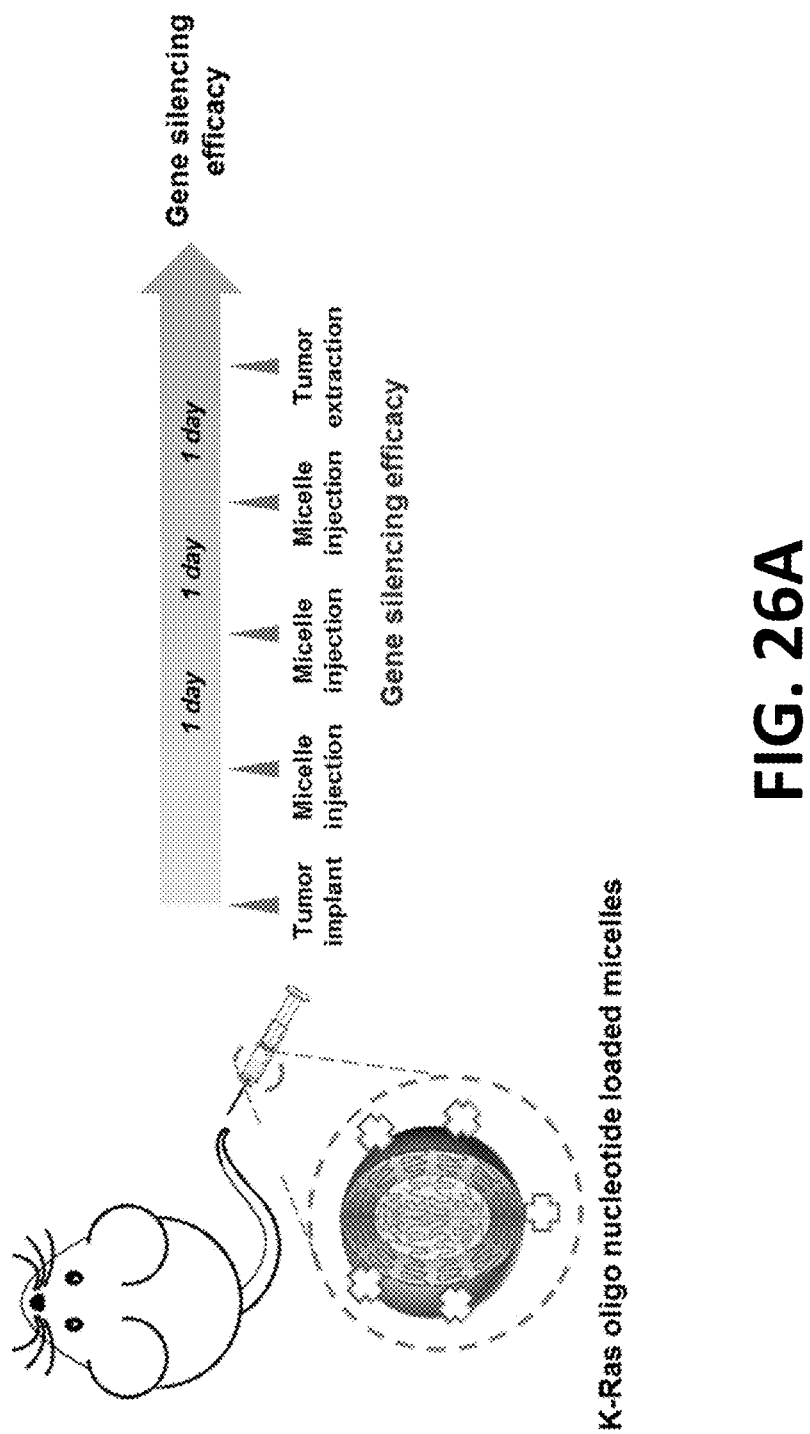
FIG. 26A shows K-Ras gene silencing efficacy in pancreatic cancer using the micellar delivery system of the present disclosure.

Pancreatic tumor bearing mice (n=3) were established after 10 days post injection of Panc1-cell into the mice. Panc1 is a human cell line used as pancreatic cancer model. The cell line was established from a pancreatic adenocarcinoma of ductal origin (epithelioid carcinoma). Cells possess the type B phenotype of G6PD. Lieber M, et al. "Establishment of a continuous tumor-cell line (panc-1) from a human carcinoma of the exocrine pancreas." Int. J. Cancer 15: 741-747, 1975. The two kinds of micelles described above were intravenously injected once a day for 3 times. See FIG. 26A. After extracting the tumor, the gene silencing efficacy was evaluated by RT-PCR.

The administration of micelles with conventional cRGD tumor targeting peptide ligand resulted in approximately 20% knock down of K-Ras. In contrast, the administration of the micelles using the alternative X-target system resulted in approximately 50% gene knock down efficacy. See FIG. 26B.

Example 7

Cellular Uptake Behavior of ASO-MDS on Human Brain Cells

Human primary microglia, astrocyte, hepatocytes and SH-5Y Cells were seeded in a 6-well plate overnight. Cells were treated with Cy5.5 labeled ASO-MDS 100 nM. Measurements of ASO-MDS uptake in cells were acquired every hour for a total of 48 h. Uptake capacity was calculated by following the percent confluency of the well using Incucyte S3 instrument.

Figure 13:
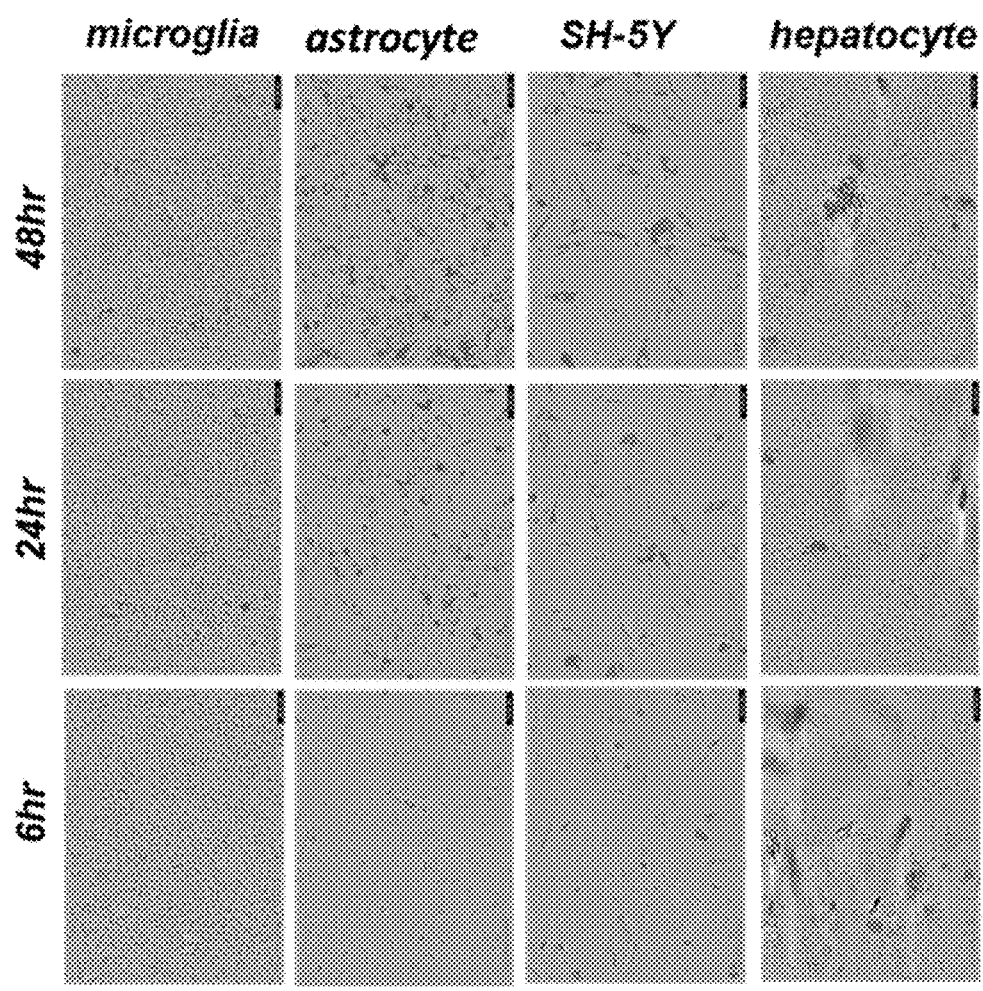
FIG. 13 shows cellular uptake of Cy5.5 labeled anti-microRNA loaded micelles by human microglia, astrocytes, neuroblasts-like SH-5Y cells, and primary hepatocytes. After incubating each type of cell with Cy5.5, labeled anti-microRNA were transfected to the cells, and the fluorescence images were tracked for 48 hr using the IncuCyte imaging platform. Uptake of anti-microRNA was significant in the human brain cells (microglia, astrocyte, SH-5Y), but no uptake was observed in hepatocytes, a liver cell-line.

To investigate uptake capacity following cell types, Cy5.5 labeled ASO-MDS were prepared and the ASO-MDS the stock was diluted with PBS. The uptake of ASO-MDS was increased in human primary microglia, astrocyte and SH-5Y cells, but not in human primary hepatocytes (FIG. 13). This indicated that ASO-MDS can be delivered specifically to cells in the brain.

Example 8

LAT1 Targetability of Anti-microRNA Loaded Micelle In Vitro

GL-26 cells were used to evaluate targeting of LAT1 by ASO-MDS micelles. GL-26 cells were seeded onto a 96-well plate with 10% FBS, 1% P/S containing DMEM. Four types of samples were used: (i) cells incubated ASO-MDS targeted to LAT1 ("target micelle"), (ii) cells incubated with ASO-MDS not targeted to LAT1 ("non-target micelle"), (iii) samples as (i) but LAT1 in the cells was inhibited by preincubation with phenyl alanine ("target micelle/inhibitor"), and (iv) samples as (ii) but LAT1 activity in the cells was inhibited by preincubation with phenyl alanine ("non-target micelle/inhibitor").

After 1 day incubation at 37° C. for 24 hr, the medium was freshly exchanged and 1 mM of free phenyl alanine was added to samples (iii) and (iv) to inhibit LAT1. Then cells were further incubated for 1 hour, and Cy 5.5 labeled anti-microRNA loaded micelles (ASO-MDS) were added at a 300 nM of RNA concentration. The medium was removed and washed twice with PBS, and 100 µL of PBS was added into each well. The remaining fluorescence intensity of the cells was measured using a Microplate reader with Ex 650/Em 690 wavelengths.

The remaining fluorescence intensity of target-micelle treated cells was approximately 3-fold higher than that of fluorescence of the non-target micelle cells indicating that there was an increase in the uptake of Cy5.5 labeled anti-microRNA when the ASO-MDS micelles were targeted to LAT1.

Figure 14:
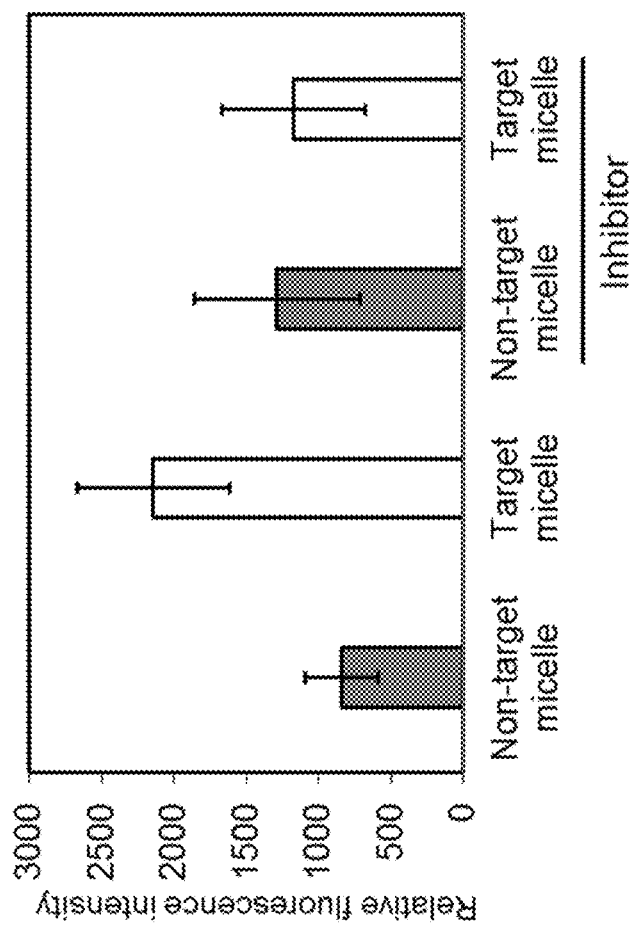
FIG. 14 shows a comparison of LAT1 targetability in GL-26 cells, which overexpress LAT1 on their surface. The drawing shows cells with and without LAt1 inhibitor treatment. The uptake of the targeted micelles was 3-fold higher than the uptake observed for non-targeted micelle. When LAT1 was inhibited, no significant differences in uptake were observed between non-target and target-micelle.

There were no significant differences in cellular uptake of Cy5.5 labeled anti-microRNA when cells treated with either targeted or non-targeted ASO-MDS were preincubated with a of LAT1 inhibitor (FIG. 14). This indicated that when LAT1 was inhibited with phenyl alanine, targeting the ASO-MDS micelles to LAT1 was not sufficient to increase Cy5.5 labeled anti-microRNA uptake by the cells. In other words, the LAT1-mediated uptake of a payload encapsulated in a micelle of the present disclosure, wherein the micelle is targeted to LAT1, depends on the functional state of LAT1.

Example 9

Bio-Distribution of Anti-microRNA Loaded Micelle

Bio-distribution of anti-microRNA was measured using an IVIS live animal imaging station. To compare the time-dependent differences in anti-microRNA distribution for naked anti-microRNA and anti-microRNA loaded micelle (ASO-MDS), both samples (25 µg of RNA concentration) were administrated to the mice via tail vein injection. The fluorescence images of mice were obtained at desired times using the IVIS live animal imaging station and observed for 16 hr.

Figure 15:
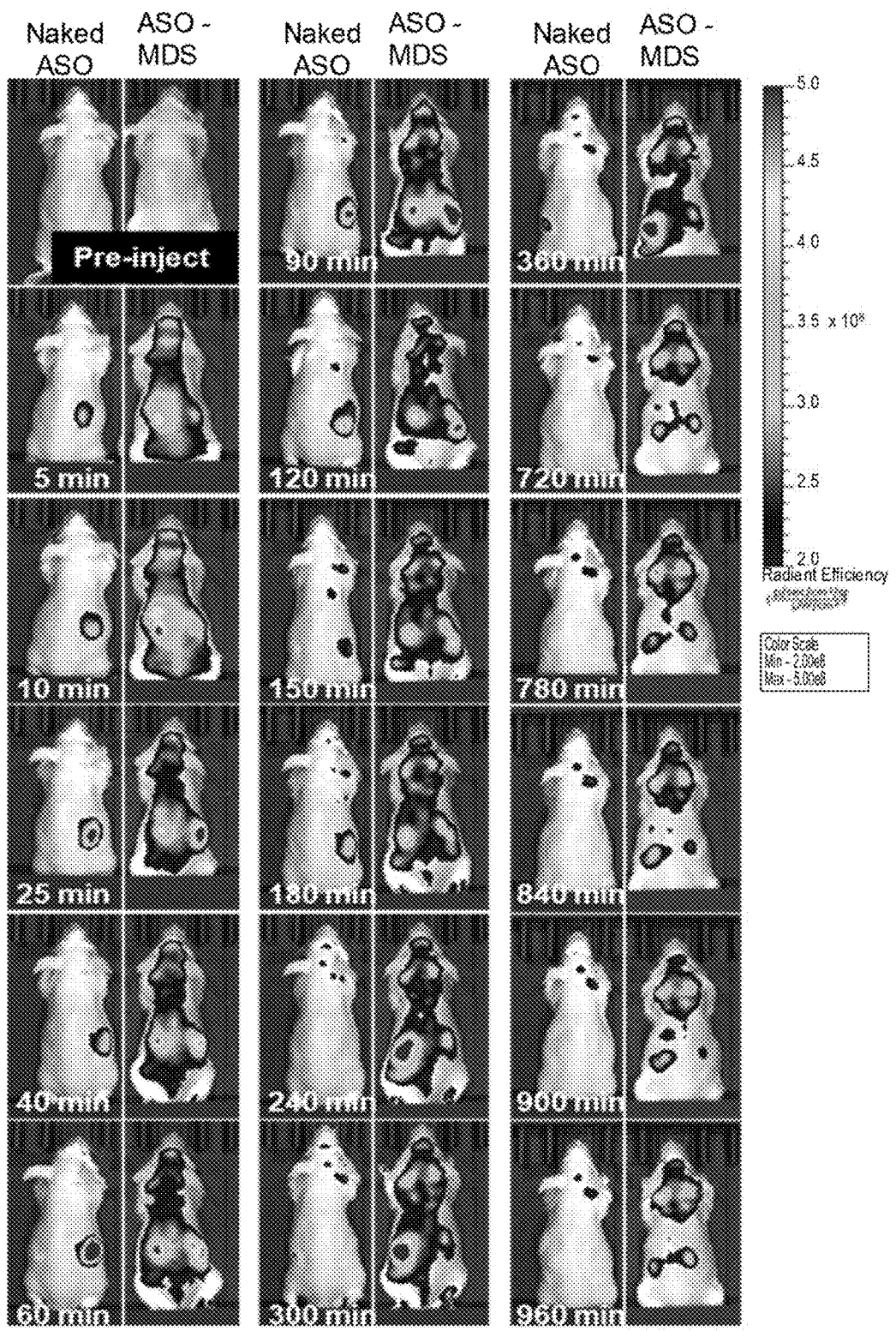
FIG. 15 compares the bio-distribution of Cy5.5 labeled free anti-microRNA and Cy5.5 labeled anti-microRNA loaded into micelles of the present disclosure (ASO-MDS; Anti Sense Oligonucleotide-Micelle Delivery System) following intravenous injection. After administration of both samples to the mice via injection, whole body fluorescence images were captured at time intervals for 16 hr.
Figure 16:
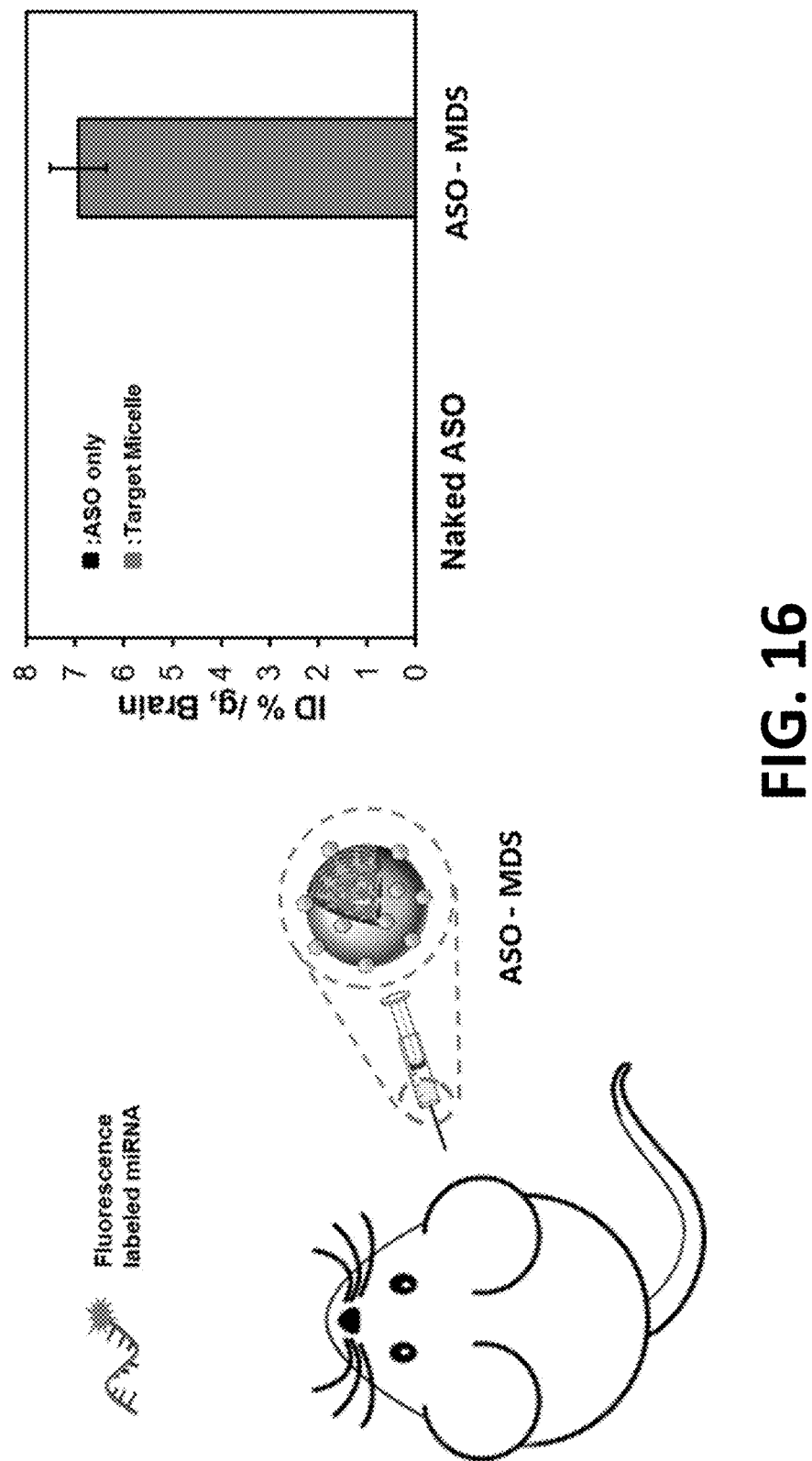
FIG. 16 shows brain accumulation of anti-miRNA loaded micelles of the present disclosure (ASO-MDS) compared to naked anti-miRNA administration (naked ASO). The Cy5.5 labeled anti-miRNA-loaded micelles were intravenously injected and remaining fluorescence intensities were measured after lysis of the brain tissue. The brain targeting micelles showed significant brain accumulation compared to non-targeted micelles.

The remaining fluorescence intensity of mice treated with naked anti-microRNA showed rapid localization into the kidney, and the signal almost disappeared in 4 hr. For anti-microRNA loaded micelles (ASO-MDS), the fluorescence intensity was mainly localized in brain, liver and kidneys. The fluorescence gradually increased in the kidney until 6 hr and decreased over time. These results indicated that naked anti-microRNA rapidly was cleared rapidly (within 4 hr) via urine due to the small size of the molecule. On the other hand, anti-microRNA loaded micelles (ASO-MDS) showed prolonged circulation and accumulated at the brain site until 16 hr, with the remaining anti-microRNA being cleared out via urine. See FIG. 15.

Example 10

In Vitro Phagocytosis Assays (ELISA and Immunocytochemistry)

Primary mixed glial cells ($2\times10^5$ cells) or human primary microglia cells ($2\times10^5$ cells) were plated in 6-well plates overnight. Cells were treated with ASO-MDS with fAβ for 4 h at a final concentration of 1 µM. Levels of human Aβ (1-42) in supernatant were measured with a human Aβ42 ELISA kit (Invitrogen, Cat #KHB3441) according to the manufacturer's instructions.

In addition, phagocytosis of human primary microglia cells was verified by fluorescence microscope. Coverslips were plated with $8\times10^4$ human primary microglia cells per coverslip resting in a well of a 24-well plate overnight. Human primary microglia cells were treated with ASO-MDS and incubated with unlabeled fAβ for 4 h at a final concentration of 1 µM. After 4 h, the cells were washed with cold PBS. For Aβ uptake measurements, primary glial cells were then fixed with 100% methanol for 1 h at −20° C., washed with PBS-T, and incubated at 4° C. with mouse anti-amyloid beta 1-16, or rabbit anti-Iba-1antibody.

Figure 18B:
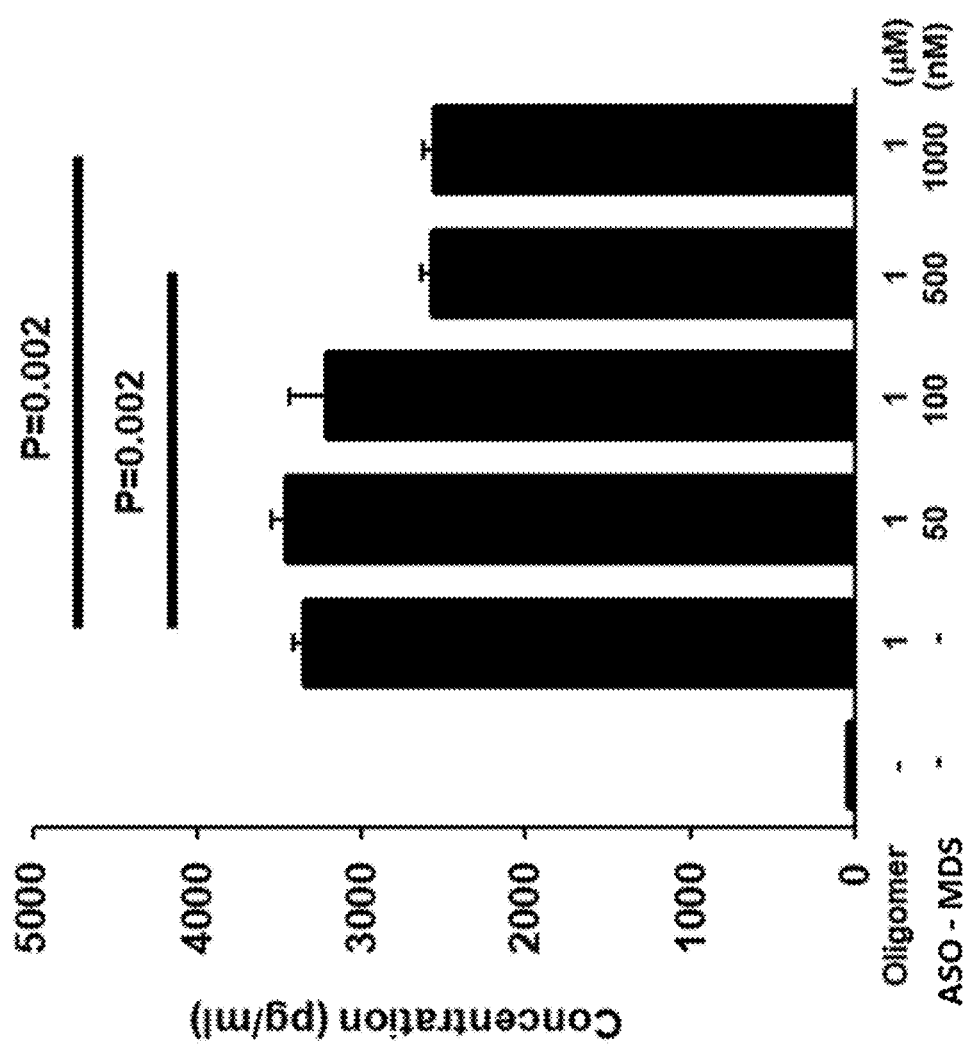
FIG. 18B shows the enhancement of phagocytosis of Aβ in mouse primary microglia cells after ASO-MDS treatment.

To assess the phagocytic effect of ASO-MDS in glial cell, Aβ aggregates were prepared by incubating Aβ monomers (100 µM) at 37° C. for 24 h and then diluting the peptide stock with cell culture medium. Primary mixed glial cells were treated with ASO-MDS, and co-treated with 1 µM fibrillar Aβ (fAβ) for 4 h. Aβ levels in conditioned media were gradually reduced in ASO-MDS transfected cells compared to control transfected cells. See FIG. 18A.

Consistent with the above results, ASO-MDS dose dependently increased the capacity for Aβ uptake by human primary microglia cells. See FIG. 18B.

Figure 18C:
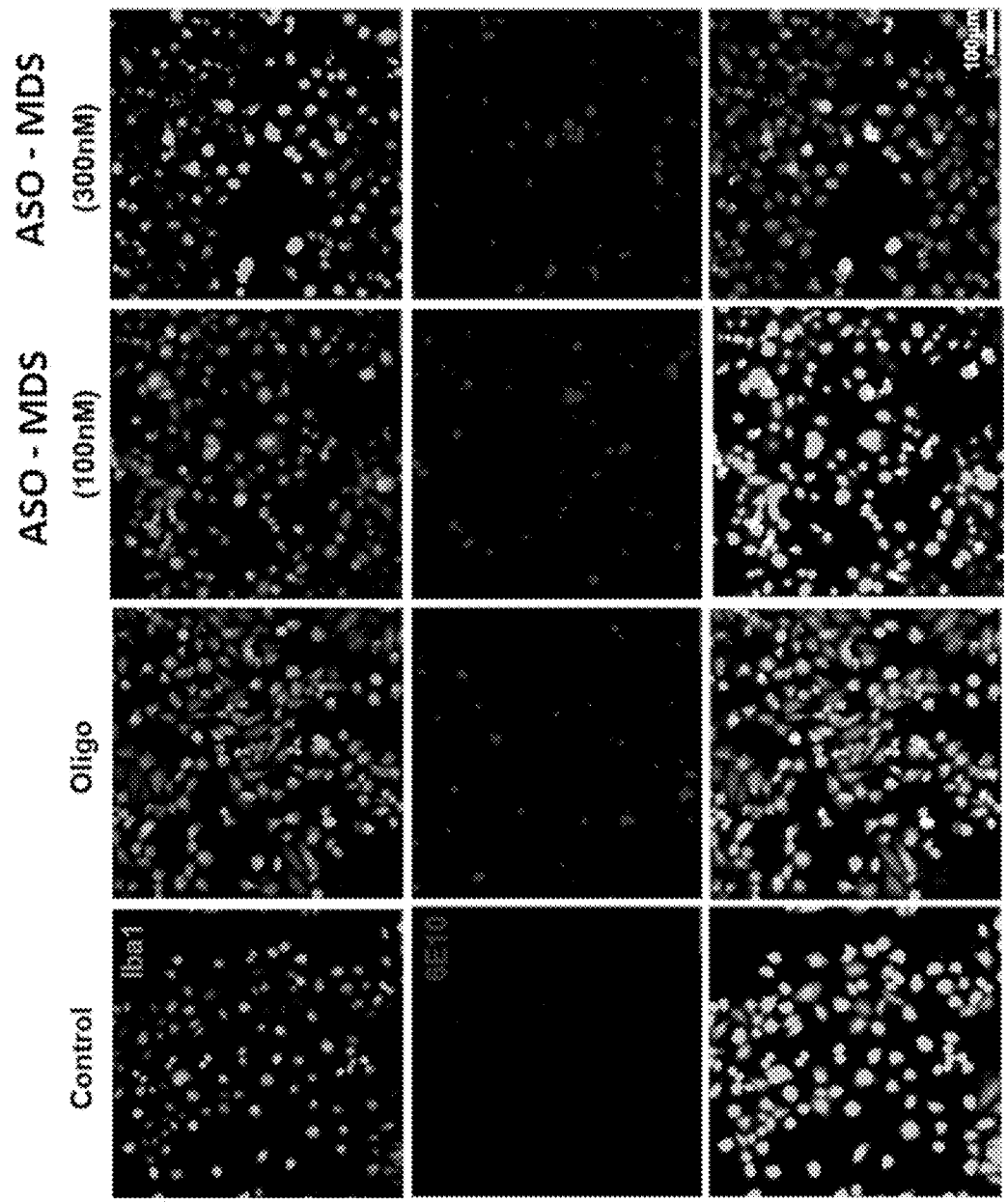
FIG. 18C shows the enhancement of phagocytosis of Aβ in mouse primary microglia cells after ASO-MDS treatment. The images show immune cytometry of Iba1 (microglia) and β-amyloid 1-16 (6E10, to detect Aβ plaque) in control or ASO-MDS treated primary microglia.
Figures 19A, 19B:
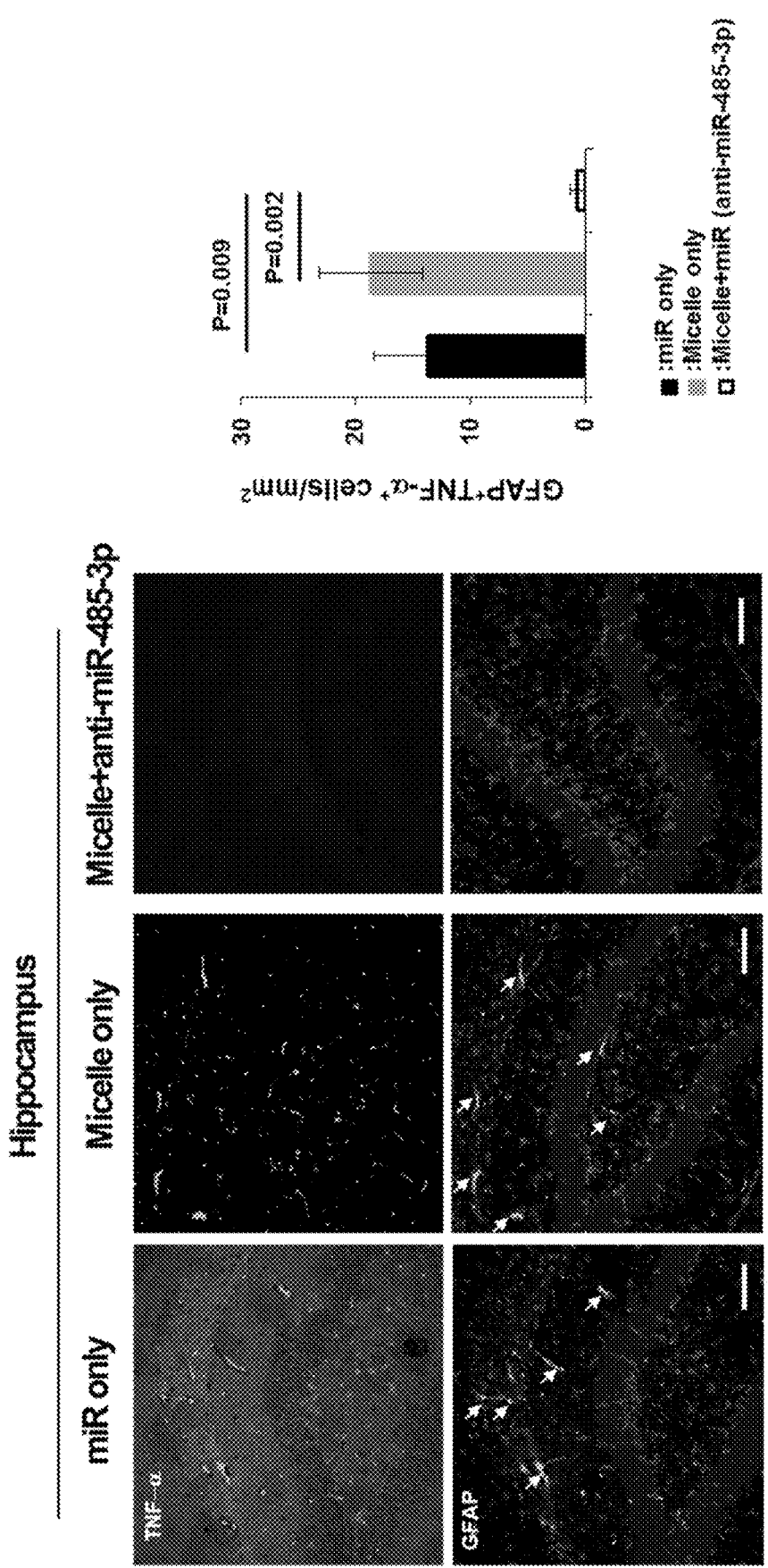
FIG. 19A shows that ASO-MDS delivery in hippocampus of 5×FAD mice reduces neuroinflammation. The images show immunohistochemical staining with anti-TNF-alpha (upper panels) and GFAP (lower panels) in coronal brain sections from Mock (miR only and micelle only (left and middle panels, respectively)—and ASO-MDS-treated 5×FAD mice (right panel). (×20) n=3.
FIG. 19B shows a bar graph of the same data in FIG. 19A. The left bar is miR only, the middle bar is micelle only, and the right bar is micelle+miR.
Figures 20A, 20B:
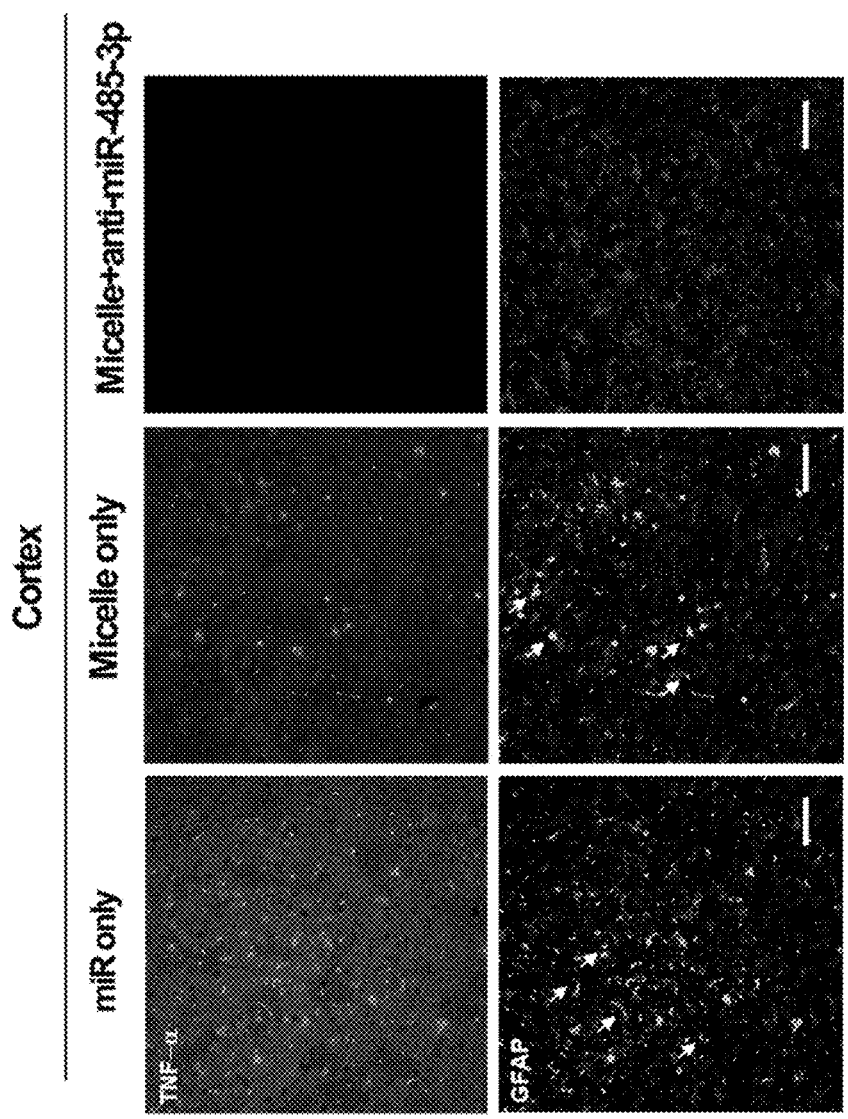
FIG. 20A shows that ASO-MDS delivery in cortex of 5×FAD mice reduces neuroinflammation. The images show immunohistochemical staining with anti-TNF-alpha (upper panels) and GFAP (lower panels) in coronal brain sections from Mock (miR only and micelle only (left and middle panels, respectively)—and ASO-MDS-treated 5×FAD mice (right panel). (×20) n=3.
FIG. 20B shows a bar graph of the same data in FIG. 20A. The left bar is miR only, the middle bar is micelle only, and the right bar is micelle+miR.

These results indicate that ASO-MDS enhances Aβ phagocytosis in glial cells. To explore the role of glial cells further, we performed immunocytometry analysis using Iba1 and 6E10 antibodies to colocalize human microglia cells and Aβ plaque. Immunocytometry showed that the expression of Aβ in glial cells was considerably elevated in ASO-MDS-treated human primary microglia cells. See FIG. 18C.

Example 11

Bio-Distribution of Anti-microRNA Loaded Micelle

Bio-distribution of anti-microRNA was measured using IVIS live animal imaging station. To compare the time dependent anti-microRNA distribution between naked RNA and RNA loaded micelle (ASO-MDS), both samples (10 µg of RNA concentration) were administrated to the mice via intramuscular injection. The fluorescence images of mice were obtained at a desired time using IVIS live animal imaging station and observed until 120 hr.

Figure 27:
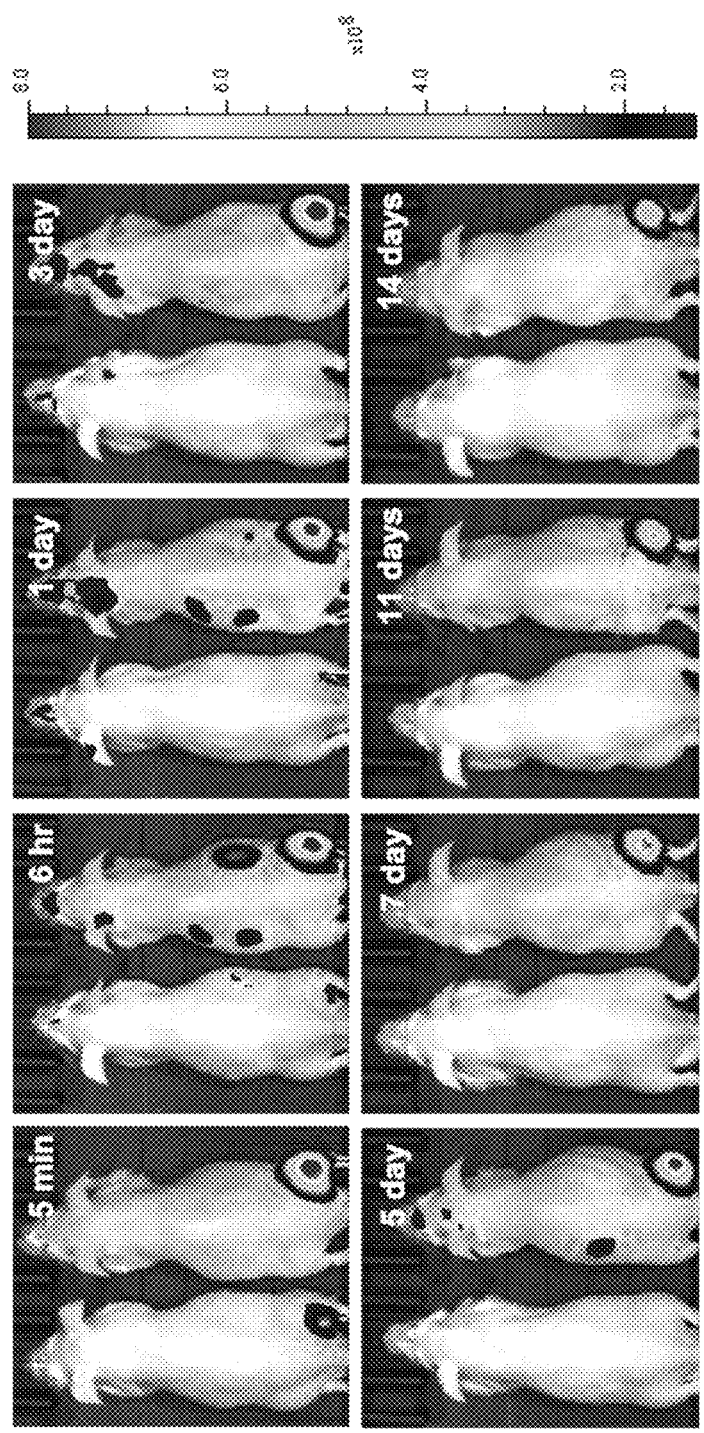
FIG. 27 compares the bio-distribution of Cy5.5 labeled anti-microRNA (naked ASO; left mice) and Cy5.5 labeled anti-microRNA loaded micelle (ASO-MDS; right mice) after intramuscular injection. After injection of both samples to the mice, fluorescence images of whole body were obtained up to 120 hr.

The remaining fluorescence intensity of naked anti-microRNA showed rapid localization into the kidney, and the signal almost disappeared within 6 hr. In case of anti-microRNA loaded micelle (ASO-MDS), the fluorescence intensity was mainly localized in skeletal muscle sites. These results indicated that clearance of naked RNA takes place rapidly within 6 hr via urine due to the small size of the molecule. On the other hand, anti-microRNA loaded micelle showed continuous fluorescence intensity in injection site and partially increased fluorescent behavior at lymph-nod, which indicated a sustained release of anti-microRNA from the anti-microRNA loaded micelle. See FIG. 27

It is to be appreciated that the Detailed Description section, and not the Summary and Abstract sections, is intended to be used to interpret the claims. The Summary and Abstract sections may set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A micelle comprising a plurality of cationic carrier units and an anionic payload, wherein each cationic carrier unit comprises
   (i) a water-soluble biopolymer moiety comprising polyethylene glycol (PEG),
   (ii) a positively charged carrier moiety polylysine comprising which comprises lysine units,
   (iii) an adjuvant moiety comprising 20 to 50 vitamin B3 units, and
   (iv) a targeting moiety comprising a ligand that can be transported by large neutral amino acid transporter 1 (LAT1),
   wherein the polylysine comprises (a) some lysine units covalently linked to the adjuvant moiety ("AM-linked lysine unit") and (b) some lysine units that are positively charged,
   wherein each AM-linked lysine unit is covalently linked to a vitamin B3 unit,
   wherein the charged carrier moieties of the plurality of cationic carrier units and the anionic payload are associated with each other via a covalent bond, a non-covalent bond, or an ionic bond, and
   wherein the water-soluble biopolymer moiety comprising PEG and the positively charged carrier moiety comprising polylysine are attached to each other directly or through a bifunctional linker.

2. The micelle of claim 1, wherein the positive charges of the charged carrier moieties and the negative charges of the anionic payload in the micelle are at a charge ratio of between 1:3 and 3:1.

3. The micelle of claim 2, wherein the positive charges of the charged carrier moieties and the negative charges of the anionic payload in the micelle are at a charge ratio of 1:1.

4. The micelle of claim 1, where the diameter of the micelle is between 1 nm and 100 nm.

5. The micelle of claim 1, wherein the anionic payload comprises a nucleic acid comprising mRNA, miRNA, miRNA sponge, tough decoy miRNA, antimir, small RNA, rRNA, siRNA, shRNA, gDNA, cDNA, pDNA, PNA, BNA, antisense oligonucleotide (ASO), aptamer, cyclic dinucleotide, or any combination thereof.

6. The micelle of claim 5, wherein the nucleic acid comprises at least one nucleoside analog comprising Locked Nucleic Acid (LNA); 2'-O-alkyl-RNA, 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-0Me), 2'-O-methoxyethyl nucleic acid (2'-M0E), or any combination thereof.

7. The micelle of claim 5, wherein the nucleic acid comprises a nucleotide sequence having 5 to 30 nucleotides in length.

8. The micelle of claim 7, wherein the nucleotide sequence is 7, 8, 9, 10, 11, 12, 13, 14, 15, 16, 17, 18, 19, 20, 21, 22, 23, 24, 25, or 26 nucleotides in length.

9. The micelle of claim 5, wherein the backbone of the nucleic acid comprises a phosphodiester linkage, a phosphotriester linkage, a methylphosphonate linkage, a phosphoramidate linkage, a phosphorothioate linkage, or any combination thereof.

10. The micelle of claim 1, wherein the targeting moiety comprises phenylalanine.

11. A pharmaceutical composition comprising the micelle of claim 1 and a pharmaceutically acceptable carrier.

12. The micelle of claim 1, wherein
   (a) the water-soluble biopolymer moiety comprises between about 40 and about 1000 PEGs; and
   (b) the polylysine comprises between 25 and 100 lysines.

13. The micelle of claim 12, wherein
   (a) the water-soluble biopolymer moiety comprises 40, 100, 150, 200, 300, 400, 500, 600, 700, 800, 900 or 1000 PEGs; and
   (b) the polylysine comprises 30, 40, 50, 60, 70, 80, 90, or 100 lysines.

14. The micelle of claim 12, wherein
   (a) the water-soluble biopolymer moiety comprises 100 to 120 PEGs; and
   (b) the polylysine comprises 30 to 40 lysines.

15. The micelle of claim 12, wherein
   (a) the water-soluble biopolymer moiety comprises 120 to 130 PEGs; and
   (b) the polylysine comprises 70 to 90 lysines.

16. The micelle of claim 1, wherein the water-soluble biopolymer moiety comprises 100 to 150 PEGs.

17. The micelle of claim 1, wherein the water-soluble biopolymer moiety comprises monodisperse PEG.

18. The micelle of claim 1, wherein the polylysine comprises 40 lysines.

19. The micelle of claim 1, wherein the polylysine comprises 80 lysines.

20. The micelle of claim 1, wherein the adjuvant moiety comprises 20 to 40 vitamin B3.

21. The micelle of claim 1, wherein the targeting moiety targets the brain.

22. The micelle of claim 16, wherein the targeting moiety allows the micelle to cross the blood brain barrier.

23. The micelle of claim 1, wherein the targeting moiety targets the central nervous system.

* * * * *